US009039659B2

(12) United States Patent
Hanson et al.

(10) Patent No.: US 9,039,659 B2
(45) Date of Patent: *May 26, 2015

(54) CONNECTION AND ALIGNMENT SYSTEMS AND METHODS

(75) Inventors: Ian B. Hanson, Wayne, PA (US); Paul F. Bente, IV, South Pasadena, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/421,564

(22) Filed: Mar. 15, 2012

(65) Prior Publication Data

US 2012/0172803 A1 Jul. 5, 2012

Related U.S. Application Data

(62) Division of application No. 12/650,378, filed on Dec. 30, 2009.

(51) Int. Cl.
*A61M 31/00* (2006.01)
*A61M 5/14* (2006.01)
*A61M 5/142* (2006.01)
*A61M 5/145* (2006.01)
*A61M 5/172* (2006.01)
(Continued)

(52) U.S. Cl.
CPC ......... *A61M 5/1413* (2013.01); *A61M 5/14248* (2013.01); *A61M 5/1456* (2013.01); *A61M 5/1723* (2013.01); *A61M 2005/14252* (2013.01); *A61M 2005/14268* (2013.01); *A61M 2005/1585* (2013.01); *A61M 2039/1072* (2013.01); *A61M 2205/14* (2013.01); *A61M 2205/6054* (2013.01); *A61M 2230/201* (2013.01)

(58) Field of Classification Search
USPC ................. 604/67, 131, 151; 324/304, 207.2, 324/207.21, 207.22
See application file for complete search history.

(56) References Cited

U.S. PATENT DOCUMENTS

| 3,701,345 A | 10/1972 | Heilman et al. |
| 3,884,230 A | 5/1975 | Wulff |
| 3,994,295 A | 11/1976 | Wulff |

(Continued)

FOREIGN PATENT DOCUMENTS

| DE | 3144825 | 5/1983 |
| EP | 0092712 | 11/1983 |

(Continued)

OTHER PUBLICATIONS

Search Report dated Jul. 13, 2011 from related PCT application No. PCT/US2010/060895.

(Continued)

*Primary Examiner* — Quynh-Nhu H Vu
(74) *Attorney, Agent, or Firm* — Foley & Lardner LLP

(57) ABSTRACT

A delivery system for delivering fluidic media to a user having a second housing portion configured to be selectively operatively engaged with and disengaged from a first housing portion, the first housing portion and the second housing portion configured to be slidable relative to each other to operatively engage each other; and a fluid connector supported by one the housing portions in a position to engage a reservoir supported by an other of the housing portions in a case where the first housing portion and the second housing portion are slid relative to each other to operatively engage each other.

20 Claims, 28 Drawing Sheets

(51) Int. Cl.
*A61M 5/158* (2006.01)
*A61M 39/10* (2006.01)

(56) References Cited

U.S. PATENT DOCUMENTS

| | | | |
|---|---|---|---|
| 4,633,232 A | 12/1986 | Nelson et al. | |
| 5,122,123 A | 6/1992 | Vaillancourt | |
| 5,176,662 A | 1/1993 | Bartholomew et al. | |
| 5,236,416 A | 8/1993 | McDaniel et al. | |
| 5,334,188 A | 8/1994 | Inoue et al. | |
| 5,628,309 A | 5/1997 | Brown | |
| 5,662,612 A | 9/1997 | Niehoff | |
| 5,954,697 A | 9/1999 | Srisathapat et al. | |
| 6,283,943 B1 | 9/2001 | Dy et al. | |
| 6,299,131 B1 | 10/2001 | Ryan | |
| 6,423,035 B1 | 7/2002 | Das et al. | |
| 6,461,329 B1 | 10/2002 | Van Antwerp et al. | |
| 6,699,218 B2 | 3/2004 | Flaherty et al. | |
| 6,727,689 B1 * | 4/2004 | Furlong et al. | 324/207.25 |
| 6,740,059 B2 | 5/2004 | Flaherty | |
| 6,749,587 B2 | 6/2004 | Flaherty | |
| 6,830,558 B2 | 12/2004 | Flaherty et al. | |
| 6,945,760 B2 | 9/2005 | Gray et al. | |
| 6,960,192 B1 | 11/2005 | Flaherty et al. | |
| 7,018,360 B2 | 3/2006 | Flaherty et al. | |
| 7,396,353 B2 | 7/2008 | Lorenzen et al. | |
| 7,811,279 B2 | 10/2010 | John | |
| 7,935,104 B2 | 5/2011 | Yodfat et al. | |
| 8,105,279 B2 | 1/2012 | Mernoe et al. | |
| 8,152,771 B2 | 4/2012 | Mogensen et al. | |
| 8,308,679 B2 * | 11/2012 | Hanson et al. | 604/67 |
| 8,435,209 B2 * | 5/2013 | Hanson et al. | 604/67 |
| 2004/0002682 A1 | 1/2004 | Kovelman et al. | |
| 2004/0162521 A1 | 8/2004 | Bengtsson | |
| 2005/0065472 A1 | 3/2005 | Cindrich et al. | |
| 2005/0101932 A1 | 5/2005 | Cote et al. | |
| 2006/0061353 A1 * | 3/2006 | Etherington et al. | 324/207.2 |
| 2006/0079765 A1 | 4/2006 | Neer et al. | |
| 2006/0200020 A1 | 9/2006 | Brister et al. | |
| 2007/0049865 A1 | 3/2007 | Radmer et al. | |
| 2007/0060871 A1 | 3/2007 | Istoc et al. | |
| 2007/0073236 A1 | 3/2007 | Mernoe et al. | |
| 2007/0191702 A1 | 8/2007 | Ofer et al. | |
| 2008/0051697 A1 | 2/2008 | Mounce et al. | |
| 2008/0051711 A1 | 2/2008 | Mounce et al. | |
| 2008/0051714 A1 | 2/2008 | Moberg et al. | |
| 2008/0077081 A1 * | 3/2008 | Mounce et al. | 604/67 |
| 2008/0097321 A1 | 4/2008 | Mounce et al. | |
| 2008/0097328 A1 | 4/2008 | Moberg et al. | |
| 2008/0097381 A1 | 4/2008 | Moberg et al. | |
| 2008/0269687 A1 | 10/2008 | Chong et al. | |
| 2008/0281270 A1 | 11/2008 | Cross et al. | |
| 2008/0319394 A1 | 12/2008 | Yodfat et al. | |
| 2008/0319414 A1 | 12/2008 | Yodfat et al. | |
| 2009/0156990 A1 | 6/2009 | Wenger et al. | |
| 2009/0182301 A1 | 7/2009 | Bassarab et al. | |
| 2009/0259183 A1 | 10/2009 | Chong et al. | |
| 2009/0264825 A1 | 10/2009 | Cote | |
| 2009/0326458 A1 | 12/2009 | Chong et al. | |
| 2010/0070878 A1 | 3/2010 | Amento et al. | |
| 2010/0137790 A1 * | 6/2010 | Yodfat | 604/67 |
| 2010/0152658 A1 | 6/2010 | Hanson et al. | |
| 2010/0274180 A1 | 10/2010 | Donovan et al. | |
| 2011/0166512 A1 | 7/2011 | Both et al. | |
| 2011/0178461 A1 | 7/2011 | Chong et al. | |
| 2011/0213306 A1 * | 9/2011 | Hanson et al. | 604/151 |
| 2012/0130312 A1 | 5/2012 | Mernoe et al. | |
| 2012/0215163 A1 * | 8/2012 | Hanson et al. | 604/67 |
| 2013/0253422 A1 * | 9/2013 | Hanson et al. | 604/67 |

FOREIGN PATENT DOCUMENTS

| | | |
|---|---|---|
| EP | 0317808 | 5/1989 |
| EP | 0 937 475 | 8/1999 |
| EP | 1177802 | 2/2002 |
| EP | 1752172 | 2/2007 |
| EP | 2 077 128 B1 | 12/2010 |
| EP | 2 375 342 | 10/2011 |
| GB | 2 327 151 | 1/1999 |
| JP | 11-339439 | 12/1999 |
| KR | 10-0692005 | 3/2007 |
| KR | 10-20090106755 | 10/2009 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 | 11/2006 |
| WO | WO-2006/122406 | 11/2006 |
| WO | WO-2006/124756 | 11/2006 |
| WO | WO-2008/024810 | 2/2008 |
| WO | WO-2008/024812 | 2/2008 |
| WO | WO-2008/024814 | 2/2008 |
| WO | WO-2008/078318 | 7/2008 |
| WO | WO-2008/092782 | 8/2008 |
| WO | WO-2008/133702 | 11/2008 |
| WO | WO-2009/001346 | 12/2008 |
| WO | WO-2009/016638 | 2/2009 |
| WO | WO-2009/033032 | 3/2009 |
| WO | WO-2009/066288 | 5/2009 |
| WO | WO-2009/093759 A1 | 7/2009 |
| WO | WO-2009/098291 | 8/2009 |
| WO | WO-2009/106517 | 9/2009 |
| WO | WO-2009/125398 A2 | 10/2009 |
| WO | WO-2009/135667 | 11/2009 |
| WO | WO-2010/042814 | 4/2010 |
| WO | WO-2011-082256 | 7/2011 |
| WO | WO-2011/090629 | 7/2011 |
| WO | WO-2011/119768 | 9/2011 |

OTHER PUBLICATIONS

Partial International Search Report from related PCT application No. PCT/US2012/064454, mailed Feb. 4, 2013, 5 pages.
International Search Report and Written Opinion from related PCT application No. PCT/US2011/066501, mailed Dec. 12, 2012, 23 pages.
International Search Report and Written Opinion from related PCT application No. PCT/US2011/066504, mailed Oct. 24, 2012, 29 pages.
International Search Report and Written Opinion from related PCT application No. PCT/US2012/022881, mailed Aug. 28, 2012, 21 pages.
International Search Report and Written Opinion from related PCT application No. PCT/US2012/022883, mailed Aug. 7, 2012, 21 pages.
International Search Report and Written Opinion from related PCT application No. PCT/US2012/055661, mailed Dec. 11, 2012, 11 pages.
U.S. Notice of Allowance from related U.S. Appl. No. 13/235,228, mailed Dec. 20, 2012, 12 pages.
U.S. Non-Final Office Action from related U.S. Appl. No. 12/553,038, mailed Dec. 28, 2012, 10 pages.
US Notice of Allowance dated Jul. 7, 2014, from related U.S. Appl. No. 12/650,287.
US Office Action dated Jun. 24, 2014, from related U.S. Appl. No. 12/649,172.
US Notice of Allowance dated Jul. 24, 2014, from related U.S. Appl. No. 13/015,028.
US Office Action dated Jul. 1, 2014, from related U.S. Appl. No. 12/974,106.
Partial Search Report dated Jun. 7, 2011, from related international application No. PCT/US2010/062414.
International Search Report and Written Opinion dated Mar. 1, 2011, from related international application No. PCT/US2010/060892.
International Search Report and Written Opinion dated Mar. 29, 2013, related international application No. PCT/US2010/060895.
Partial Search Report dated Mar. 23, 2011, from related international application No. PCT/US2010/047590.

(56) References Cited

OTHER PUBLICATIONS

International Search Report and Written Opinion dated Sep. 6, 2011, from related international application No. PCT/US2010/047590.
Partial Search Report dated Jul. 9, 2012, from related international application No. PCT/US2011/066501.
Partial Search Report dated Apr. 16, 2012, from related international application No. PCT/US2011/066504.
Partial Search Report dated May 4, 2012, from related international application No. PCT/US2012/022881.
Partial Search Report dated May 4, 2012, from related international application No. PCT/US2012/022883.
International Search Report and Written Opinion dated Jun. 12, 2013, from related international application No. PCT/US2012/064454.
US Office Action dated Feb. 2, 2012, from related U.S. Appl. No. 12/553,038.
US Office Action dated Jul. 20, 2012, from related U.S. Appl. No. 12/553,038.
US Office Action dated Jun. 20, 2013, from related U.S. Appl. No. 12/553,038.
US Office Action dated Dec. 22, 2011, from related U.S. Appl. No. 12/649,619.
US Office Action dated Aug. 16, 2012, from related U.S. Appl. No. 12/649,619.
US Notice of Allowance dated Sep. 19, 2012, from related U.S. Appl. No. 12/649,619.
US Office Action dated Jun. 18, 2012, from related U.S. Appl. No. 12/650,287.
US Office Action dated Jul. 20, 2012, from related U.S. Appl. No. 12/650,378.
US Office Action dated Mar. 3, 2011, from related U.S. Appl. No. 12/649,172.
US Office Action dated Oct. 7, 2010, from related U.S. Appl. No. 12/649,172.
US Office Action dated Jun. 19, 2012, from related U.S. Appl. No. 12/649,172.
US Office Action dated Aug. 1, 2012, from related U.S. Appl. No. 13/015,028.
US Office Action dated Aug. 2, 2012, from related U.S. Appl. No. 13/015,051.
US Office Action dated Aug. 2, 2012, from related U.S. Appl. No. 12/974,106.
US Office Action dated Aug. 2, 2012, from related U.S. Appl. No. 12/974,117.
US Office Action dated May 22, 2013, from related U.S. Appl. No. 13/103,014.
Japanese Office Action from related Japanese Patent Application No. 2012-528022, issued Mar. 25, 2014, 3 pages.
U.S. Notice of Allowance dated Dec. 19, 2014, from related U.S. Appl. No. 12/650,378.
U.S. Notice of Allowance dated Sep. 22, 2014, from related U.S. Appl. No. 13/015,051.
U.S. Office Action dated Sep. 5, 2014, from related U.S. Appl. No. 12/650,378.
U.S. Office Action dated Sep. 11, 2014, from related U.S. Appl. No. 13/462,752.
International Search Report and Written Opinion from related patent application No. PCT/US2010/062414, Jun. 12, 2011.
IPRP dated Mar. 6, 2012 from related PCT/US2010/047590 application.
U.S. Office Action dated Jan. 16, 2015, from related U.S. Appl. No. 13/462,752.
U.S. Office Action dated Jan. 16, 2015, from related U.S. Appl. No. 13/791,773.

* cited by examiner

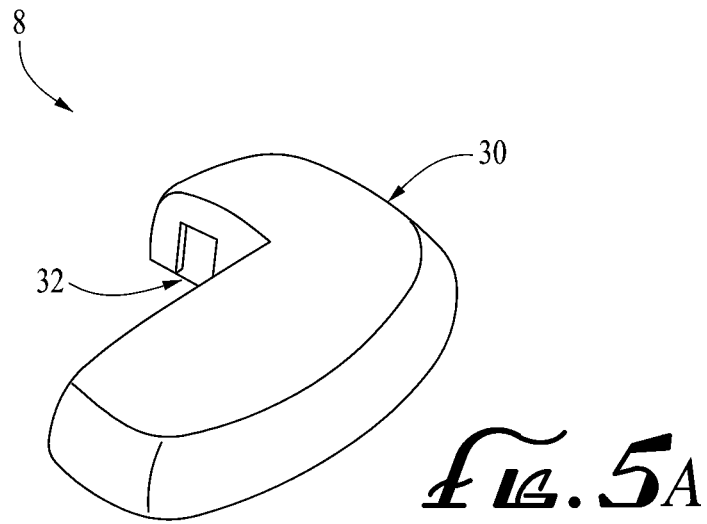
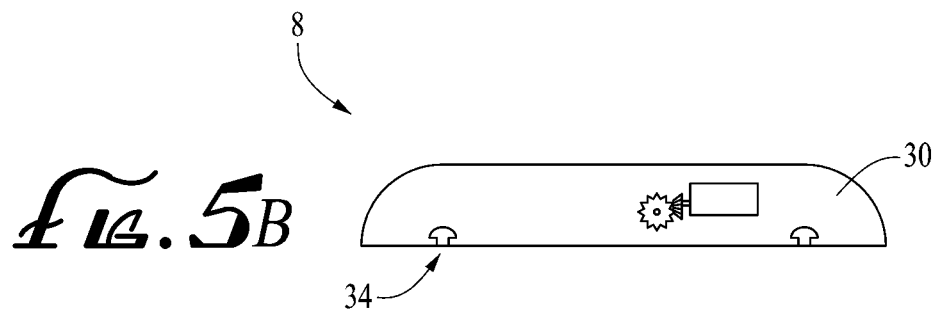
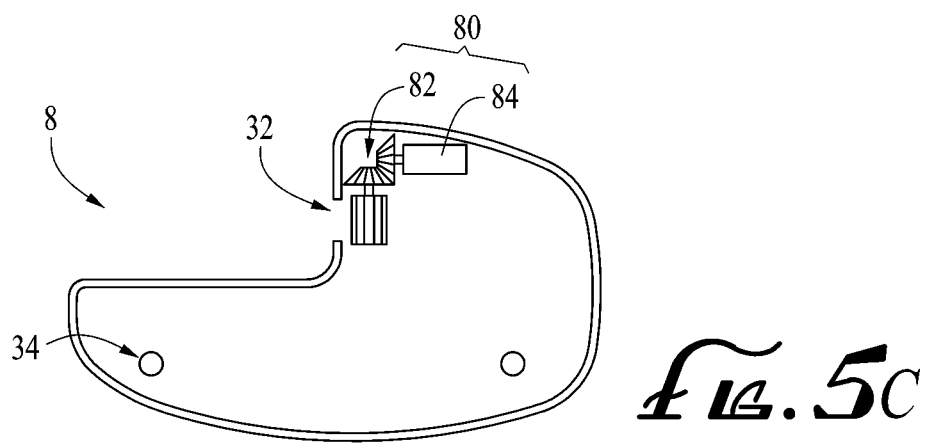

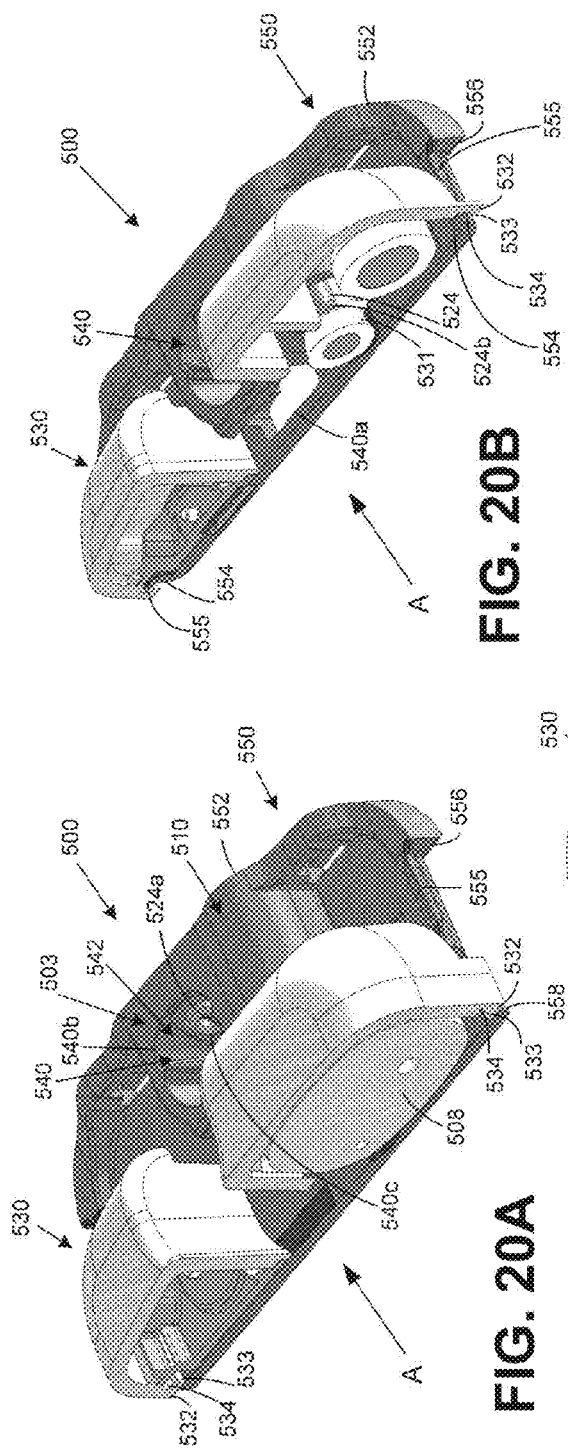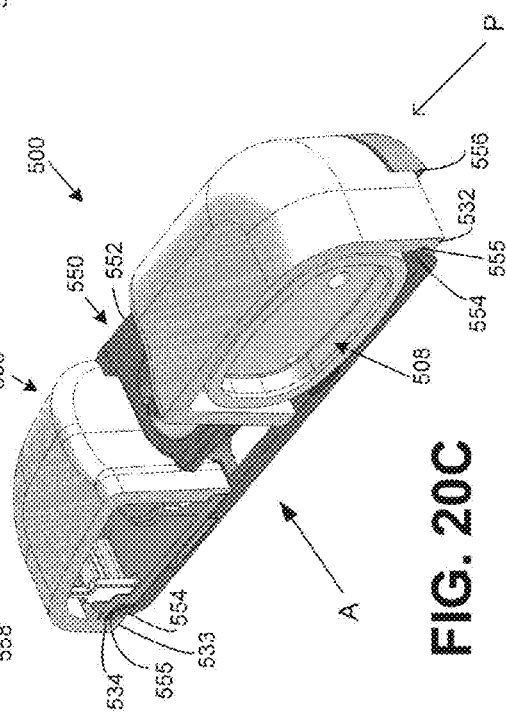

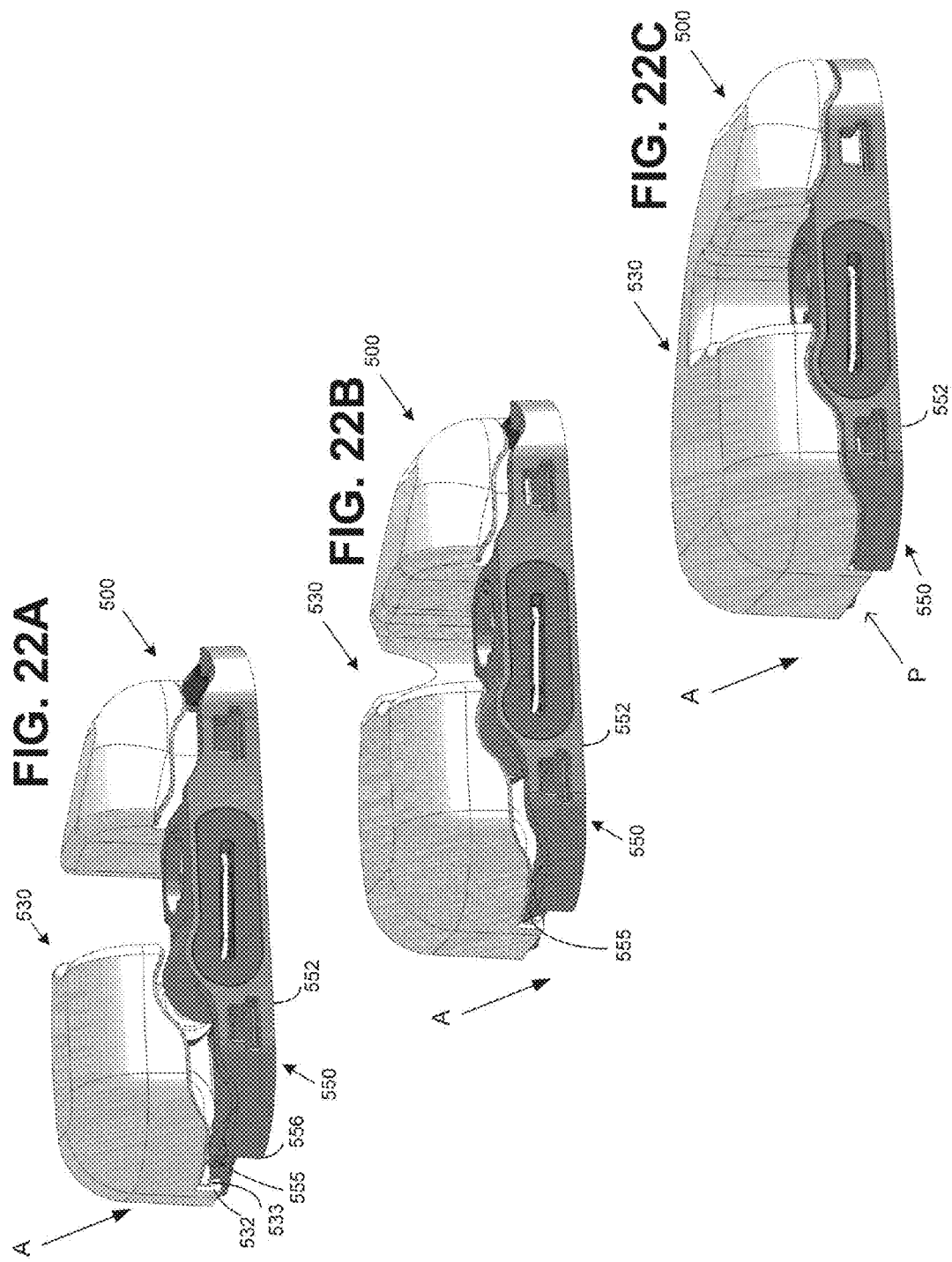

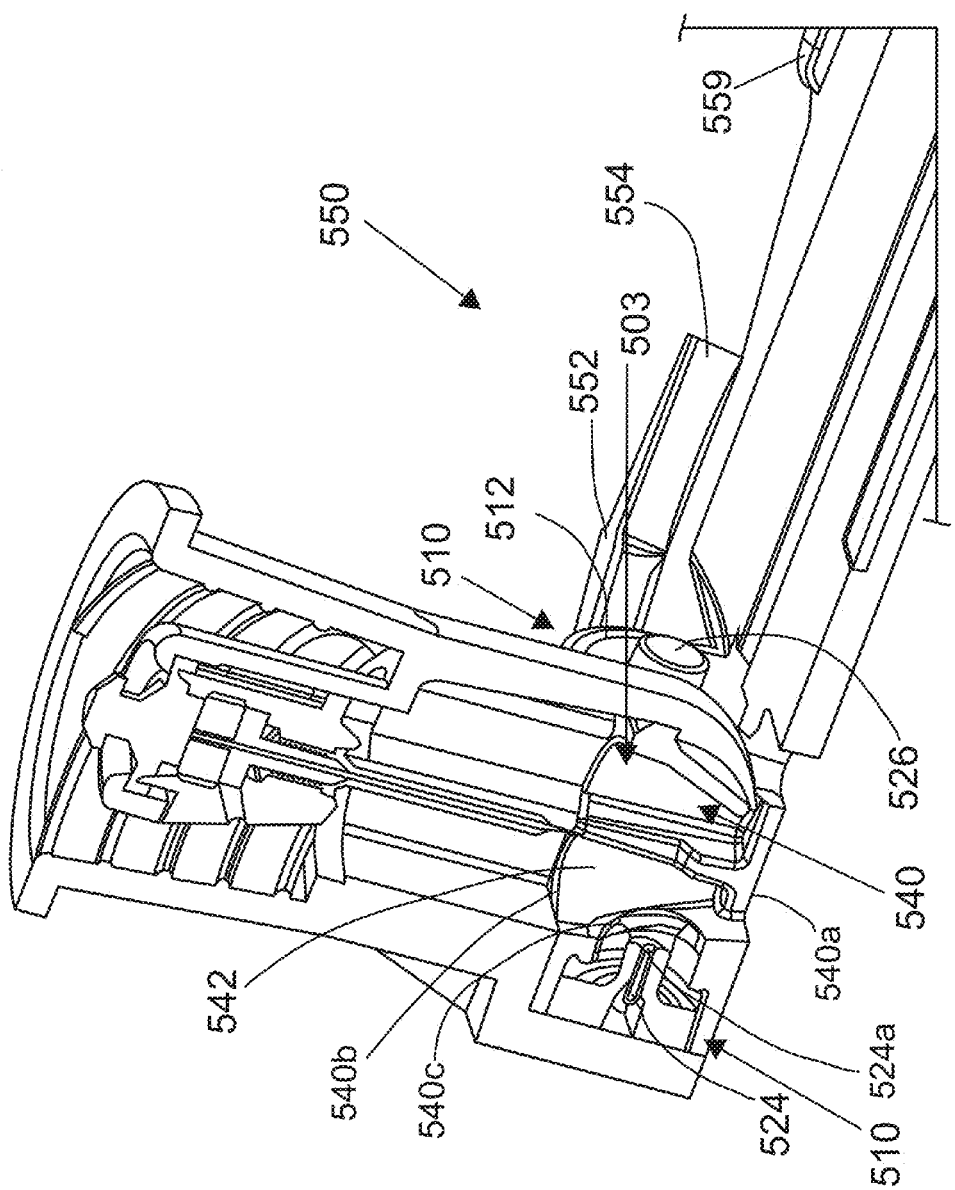

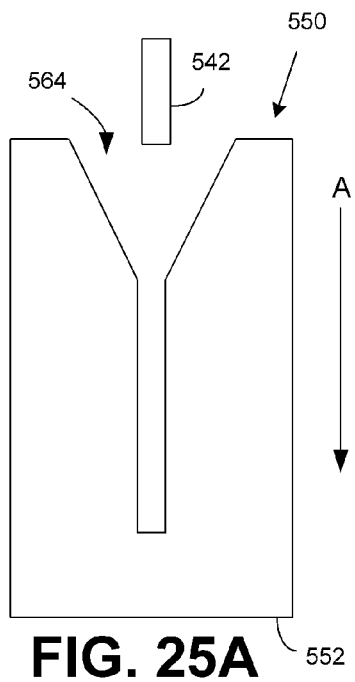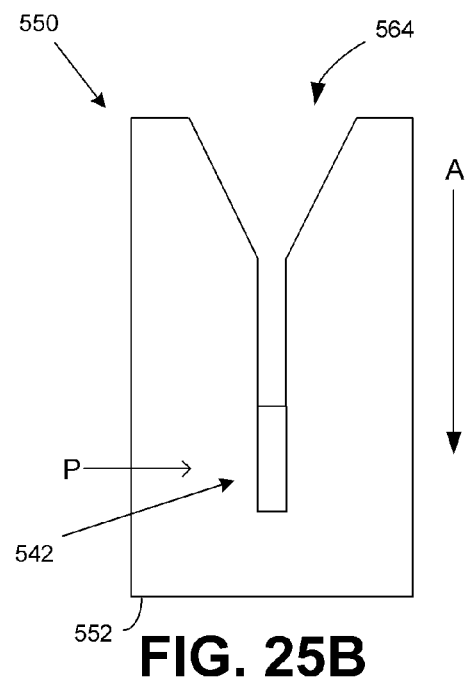
FIG. 25A    FIG. 25B
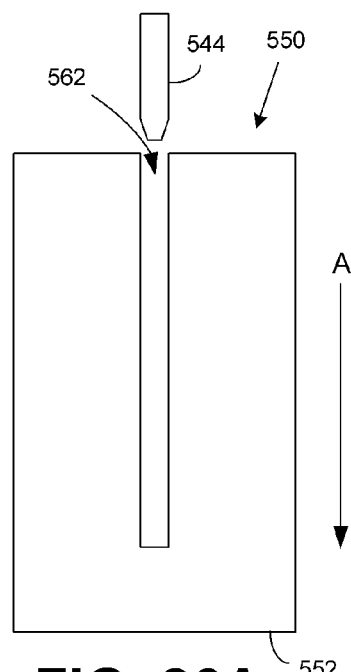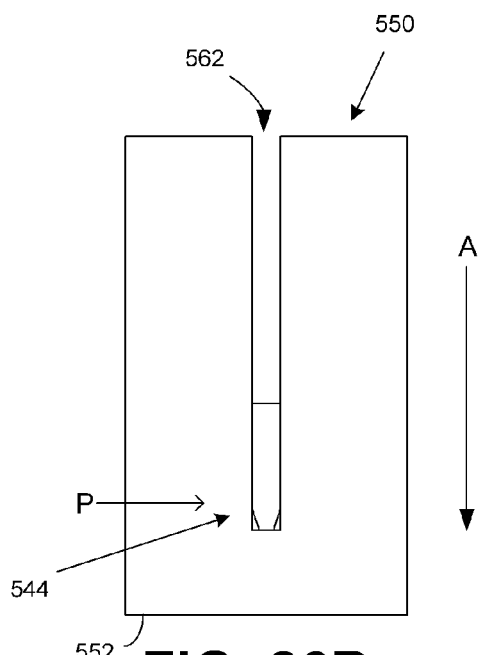
FIG. 26A    FIG. 26B

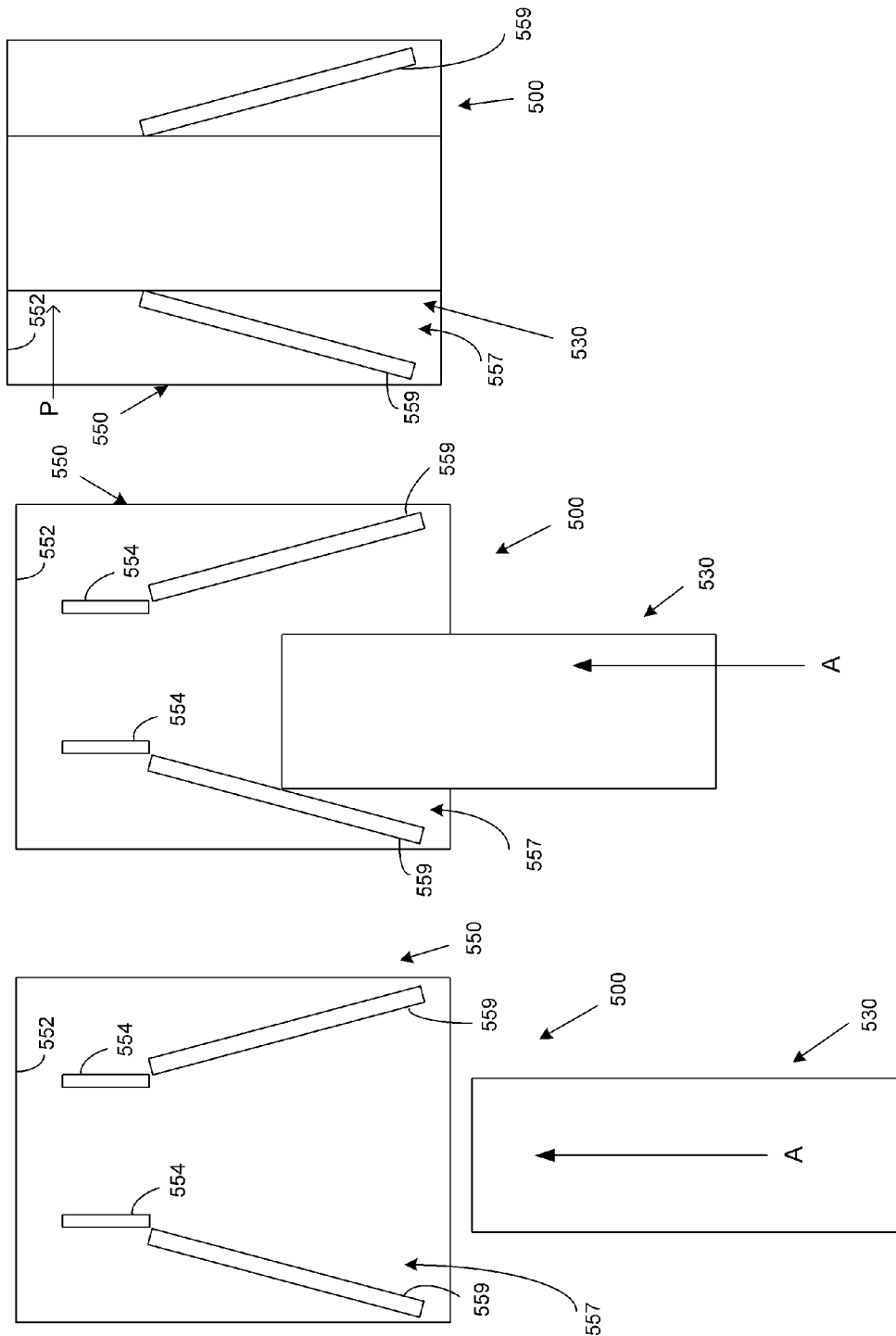

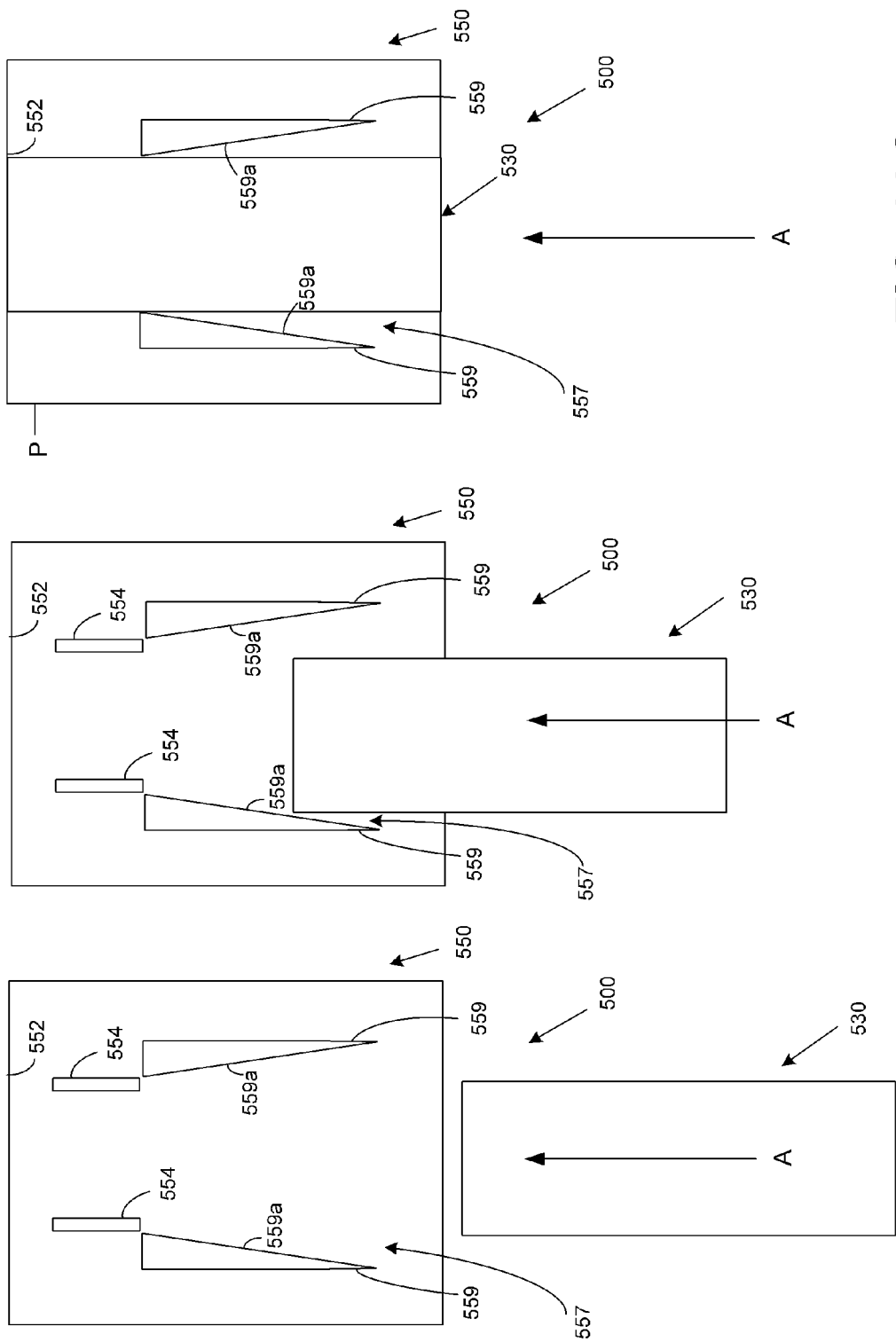

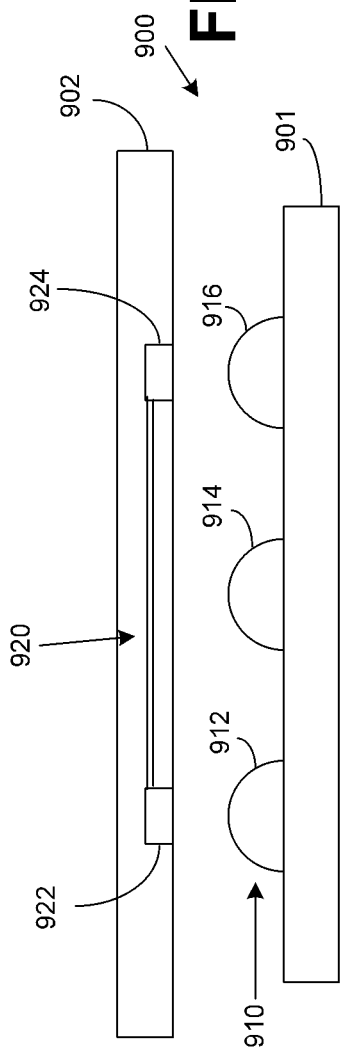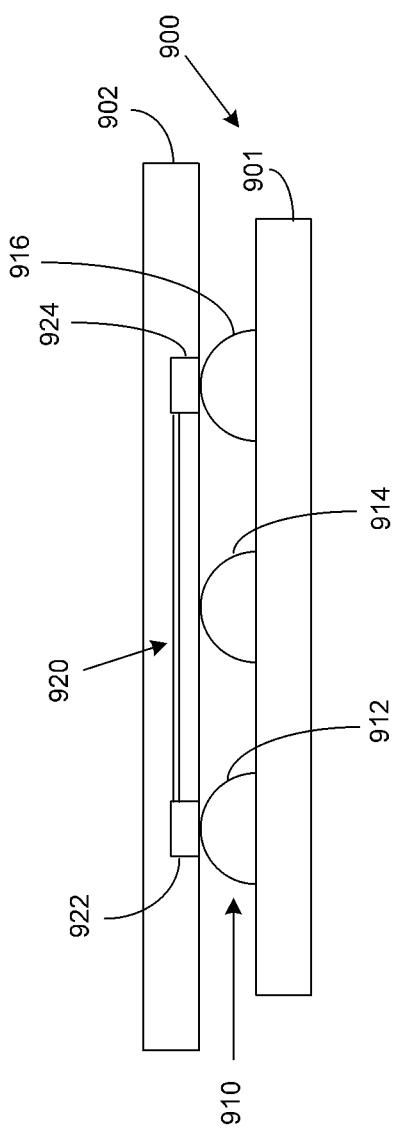

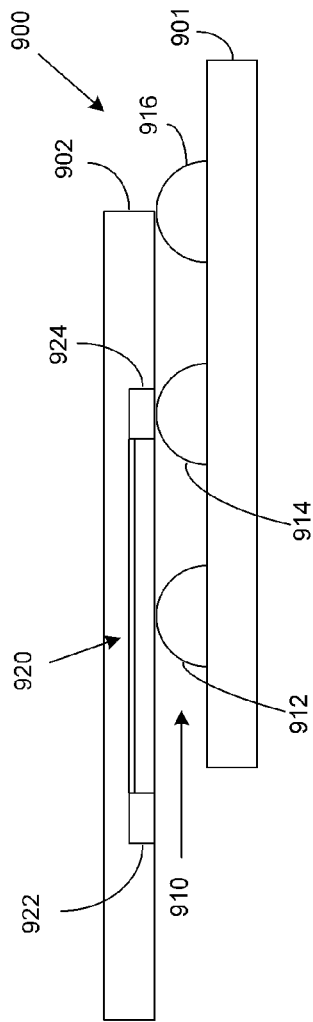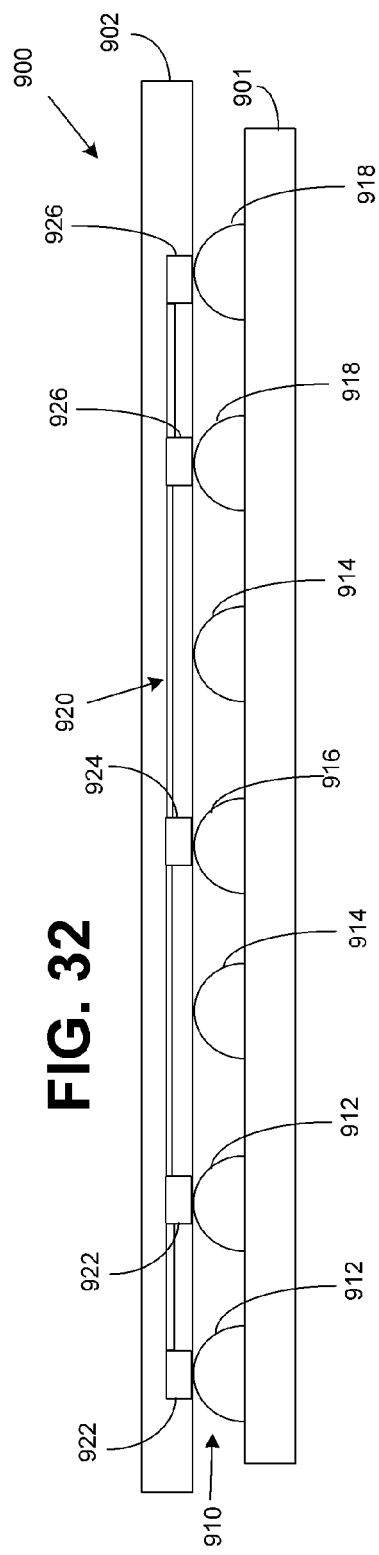

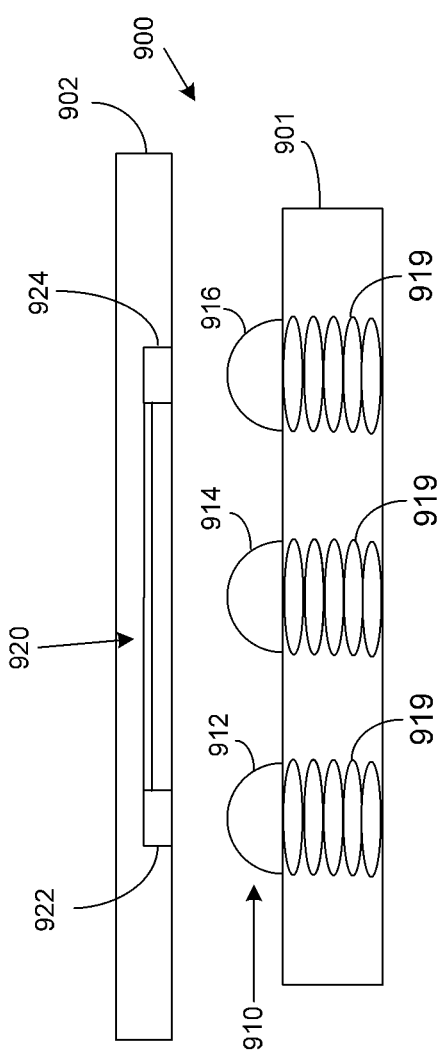
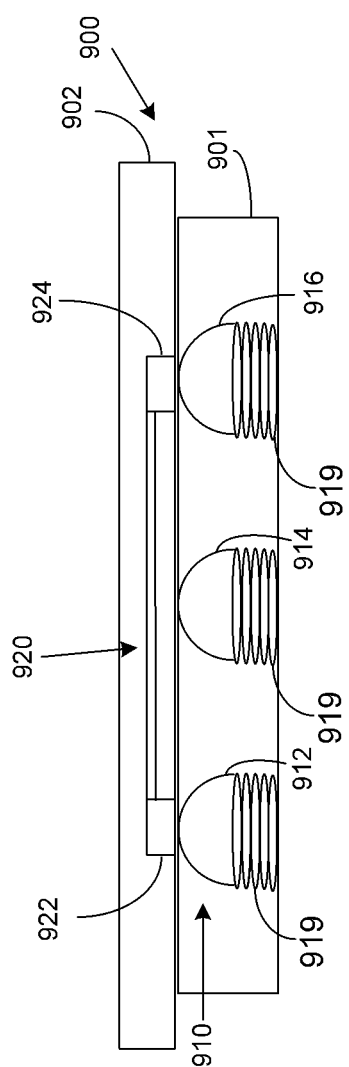

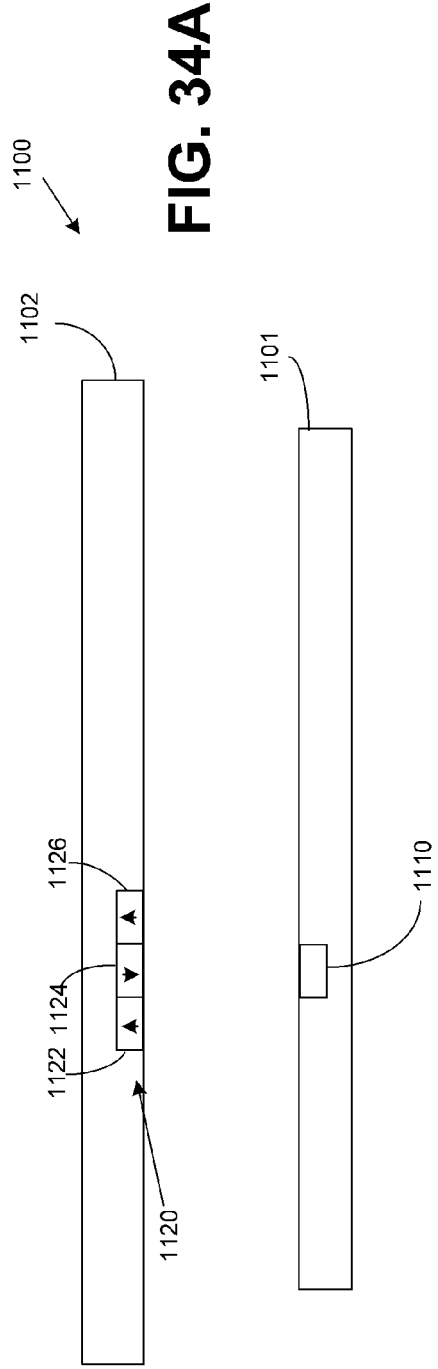
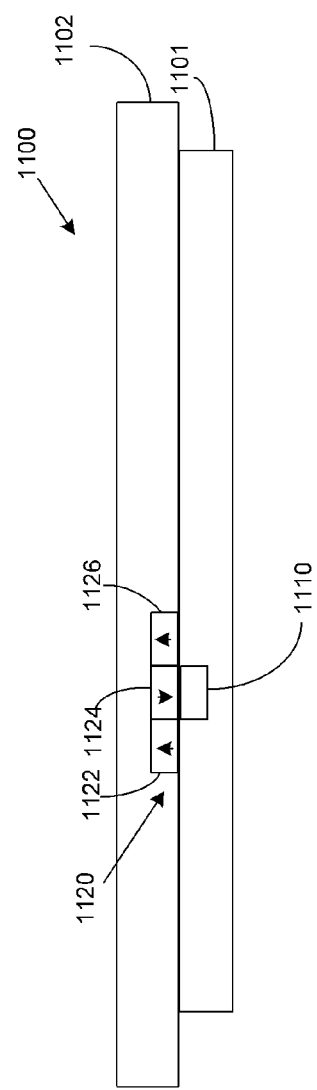

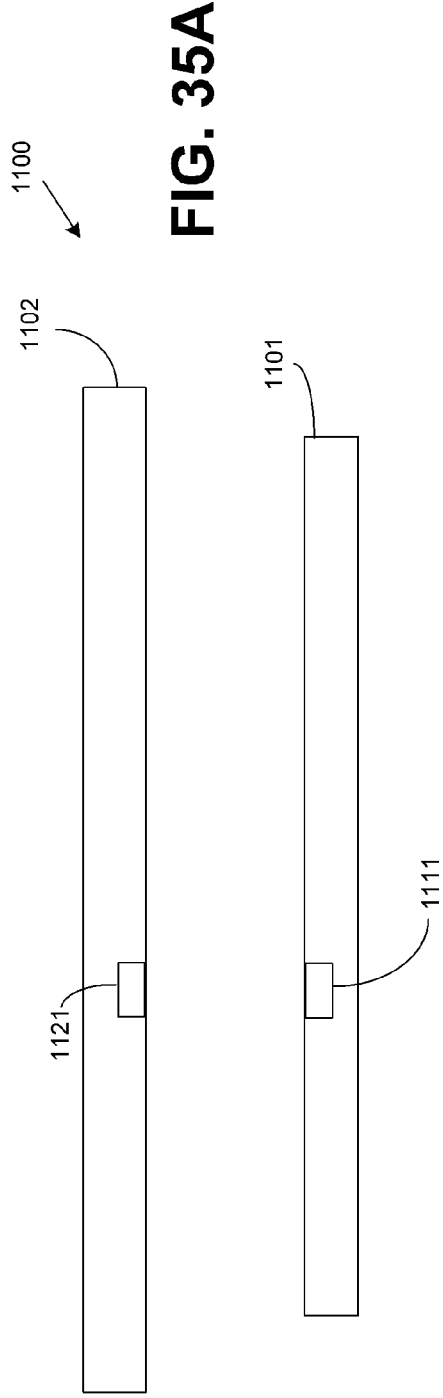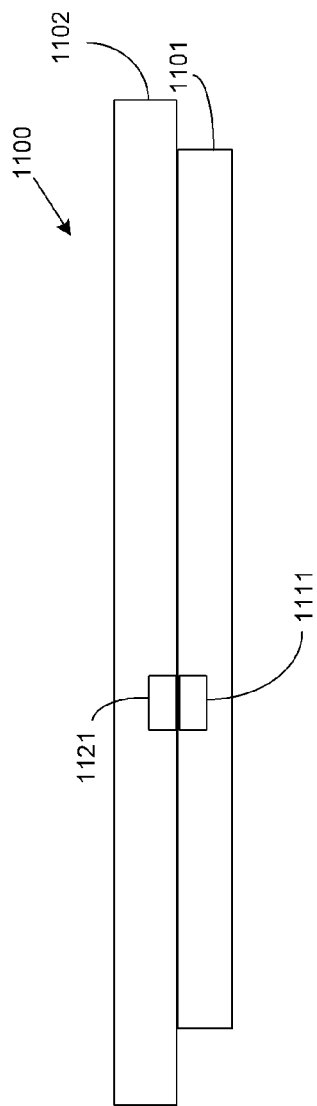

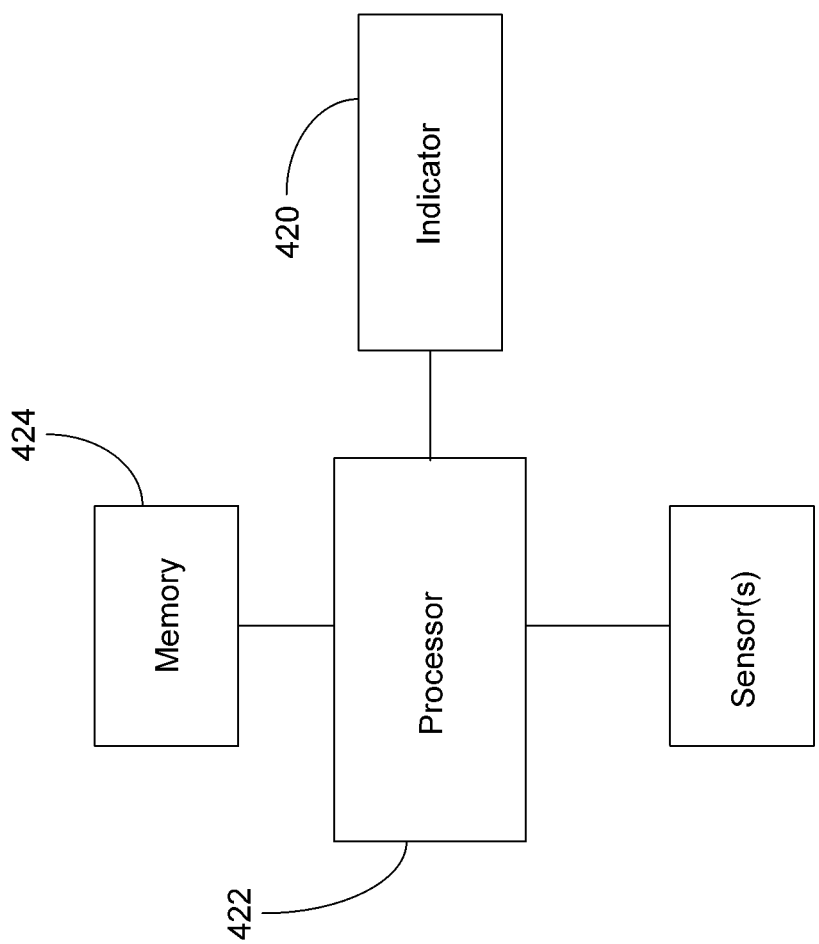

US 9,039,659 B2

CONNECTION AND ALIGNMENT SYSTEMS AND METHODS

CROSS-REFERENCE TO RELATED PATENT APPLICATIONS

This application is a Divisional of U.S. application Ser. No. 12/650,378, filed Dec. 30, 2009, incorporated herein by reference in its entirety.

BACKGROUND OF THE INVENTION

1. Field of the Invention

Embodiments of the present invention generally relate to medical device systems and methods, and, in specific embodiments, such systems and methods that include connection and/or alignment features for connecting and/or aligning components of medical device systems.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A delivery system for delivering fluidic media to a use may include, but is not limited to, a first housing portion, a second housing portion, and a fluid connector. The first housing portion may be adapted to be carried by a user. The second housing portion may be configured to be selectively operatively engaged with and disengaged from the first housing portion. One of the first housing portion and the second housing portion may be for supporting a reservoir having an interior volume for containing fluidic media. The first housing portion and the second housing portion may be configured to be slidable relative to each other to operatively engage each other. The fluid connector may be supported by the other of the first housing portion and the second housing portion in a position to engage the reservoir in a case where the reservoir is supported by the one of the first housing portion and the second housing portion and the first housing portion and the second housing portion are slid relative to each other to operatively engage each other.

In various embodiments, the first housing portion may be configured to be slidable in a first direction relative to the second housing portion at least between a first position and a second position. The first housing portion may be operatively engaged with the second housing portion in case where the first housing portion is in the second position relative to the second housing portion.

In some embodiments, the reservoir may be supported by the first housing portion and the fluid connector is supported by the second housing portion. The fluid connector may be engaged with the reservoir for fluid flow between the fluid connector and the reservoir in a case where the first housing portion is in the second position relative to the second housing portion In some embodiments, the delivery system may further include a connection structure for connecting the first housing portion and the second housing portion as the first housing portion slides relative to the second housing portion from the first position to the second position. In further embodiments, the first housing portion may be slidable in the first direction relative to the second housing portion at least from an unlocked position to at least a locked position.

In further embodiments, the connection structure may comprise a dovetail connection structure. The dovetail connection structure may include a dovetail supported by one of the first housing portion and the second housing portion and a groove on the other of the first housing portion and the second housing portion relative to the one of the first housing portion and the second housing portion supporting the dovetail. The dovetail may be for moving along at least a portion of the groove and engaging a surface defining the groove as the first housing portion slides relative to the second housing portion to the second position.

In further embodiments, the connection structure may include a protrusion supported by one of the first housing portion and the second housing portion and a groove on the other of the first housing portion and the second housing portion relative to the one of the first housing portion and the second housing portion supporting the protrusion. The protrusion may be for moving along at least a portion of the groove and engaging a surface defining the groove as the first housing portion slides relative to the second housing portion to the second position.

In yet further embodiments, the surface defining the groove may be tapered to allow the protrusion to engage the surface of the groove in a friction fit manner as the first housing portion slides relative to the second housing portion to the second position. In yet further embodiments, the protrusion may be tapered to allow the protrusion to engage the surface in a friction fit manner as the first housing portion slides relative to the second housing portion to the second position.

In yet further embodiments, the connection structure may include an abutment defining a cavity on the other of the first housing portion and the second housing portion relative to the one of the first housing portion and the second housing portion supporting the protrusion. The abutment may be for locking the protrusion in the cavity when the first housing portion is in the second position relative to the second housing portion.

In further embodiments, the connection structure may include a tab and an abutment. The tab may be supported by one of the first housing portion and the second housing portion and a recess on the other of the first housing portion and the second housing portion relative to the one of the first housing portion and the second housing portion supporting the tab. The tab may be for moving along at least a portion of the recess as the first housing portion slides relative to the second housing portion to the second position.

The abutment may define a cavity on the other of the first housing portion and the second housing portion relative to the one of the first housing portion and the second housing portion supporting the tab. The abutment may be for locking the tab in the cavity when the first housing portion is in the second position relative to the second housing portion.

In some embodiments, one of the first housing portion and the second housing portion may have a first engagement member. The other of the first housing portion and the second housing portion, relative to the one of the first housing portion and the second housing portion having the first engagement member, may have a second engagement member. The first engagement member and the second engagement member may be configured to engage each other as the first housing portion slides relative to the second housing portion to the second position to lock the first housing portion to the second housing portion In further embodiments, the first engagement member may comprise a plurality of tabs. The second engagement member may comprise at least one of a plurality of apertures and tabs for engaging at least one of the plurality of tabs as the first housing portion slides relative to the second housing portion to the second position to lock the first housing portion to the second housing portion. In further embodiments, the first engagement member and the second engagement member may inhibit separation of the first housing portion from the second housing portion in an axial direction transverse to the first direction in a case where the first engagement member and the second engagement member are engaged with each other.

In some embodiments, the one of the first housing portion and the second housing portion may comprise a pair of ridges extending along a portion of the one of the first housing portion and the second housing portion in the first direction. The pair of ridges may be for guiding the other of the first housing portion and the second housing portion as the first housing portion slides relative to the second housing portion to the second position.

In further embodiments, each of the ridges may extend along a periphery of the one of the first housing portion and second housing portion. In further embodiments, the ridges of the pair of ridges may be parallel to each other. In yet further embodiments, each of the ridges may have an inner surface. The inner surface of each of the ridges may be nonparallel to each other. In further embodiments, the ridges of the pair of ridges may be non-parallel to each other.

In further embodiments, the delivery system may further include a connection structure for connecting the first housing portion and the second housing portion as the first housing portion slides relative to the second housing portion to the second position. The pair of ridges may be for guiding the other of the first housing portion and the second housing portion to allow the connection structure to connect the first housing portion and the second housing portion as the first housing portion slides relative to the second housing portion to the second position.

In some embodiments, one of the first housing portion and the second housing portion may have a stopping surface for contacting a portion of the other of the first housing portion and the second housing portion, relative to the one of the first housing portion and the second housing portion having the stopping surface, to substantially prevent the reservoir supported by the one of the first housing portion and the second housing portion from contacting the other of the first housing portion and the second housing portion relative to the one of the first housing portion and the second housing portion supporting the reservoir.

In further embodiments, the stopping surface may be for contacting a portion of the other of the first housing portion and the second housing portion, relative to the one of the first housing portion and the second housing portion having the stopping surface, to substantially prevent the reservoir from contacting the other of the first housing portion and the second housing portion, relative to the one of the first housing portion and the second housing portion, after the fluid conduit and the reservoir are engaged.

In some embodiments, the delivery system may further include a pair of magnets. The pair of magnets may include a first magnet supported on one of the first housing portion and the second housing portion and a second magnet supported on the other of the first housing portion and the second housing portion relative to the one of the first housing portion and the second housing portion supporting the first magnet. The first magnet and the second magnet may be configured to align the first housing portion and the second housing portion in a case where the first housing portion slides relative to the second housing portion to the second position and is misaligned with the second housing portion.

In further embodiments, each of the magnets may be arranged to repel each other in a case where the first housing portion slides relative to the second housing portion to the second position and is misaligned with the second housing portion. In yet further embodiments, each of the magnets may have common poles.

In some embodiments, one of the first housing portion and the second housing portion may have a latch for engaging the other of the first housing portion and the second housing portion, relative to the one of the first housing portion and the second housing portion having the latch, when the first housing portion is in the second position relative to the second housing portion. In further embodiments, the latch may be configured to be squeezable to at least one of engage and disengage the other of the first housing portion and the second housing portion relative to the one of the first housing portion and the second housing portion having the latch. In further embodiments, the other of the first housing portion and the second housing portion, relative to the one of the first housing portion and the second housing portion having the latch, may have a sensor for sensing the latch.

In further embodiments, one of the first housing portion and the second housing portion may have a bias member for biasing the first housing portion and the second housing portion apart from each other in a case where the first housing portion is slid in the first direction, but is not slid to the second position. The latch may be for engaging the other of the first housing portion and the second housing portion, relative to the one of the first housing portion and the second housing portion having the latch, in a case where the first housing portion is slid in the first direction to the second position.

In some embodiments, one of the first housing portion and the second housing portion may have a bias member for biasing the first housing portion and the second housing portion apart from each other in a case where the first housing portion is slid in the first direction, but is not slid to the second position.

In some embodiments, the fluid connector may comprise a needle for piercing a septum of the reservoir in a case where the reservoir is supported by the one of the first housing portion and the second housing portion and the first housing portion slides relative to the second housing portion to the second position. In some embodiments, the fluid connector may have a first opening in fluid communication with the interior volume of the reservoir in a case where the reservoir is supported by the one of the first housing portion and the second housing portion and the first housing portion and the second housing portion are operatively engaged. The fluid connector may have a second opening in fluid communication with an infusion path extending into skin of a user.

In some embodiments, the fluid connector may be in fluid communication with a subcutaneous path in a user. The fluid connector may be for delivering fluidic media from the interior volume of the reservoir to a user in a case where the fluid connector is engaged with the reservoir and the fluidic media is expelled from the interior volume of the reservoir. In further embodiments, the first housing portion may be engageable with a cannula for insertion into the user to provide the subcutaneous path.

A method of making a medical device may include but is not limited to, any one of or combination of: (i) adapting a first housing portion to be carried by a user; (ii) configuring a second housing portion to be selectively operatively engaged with and disengaged from the first housing portion, one of the first housing portion and the second housing portion for supporting a reservoir having an interior volume for containing fluidic media, the first housing portion and the second housing portion configured to be slidable relative to each other to operatively engage each other; and (iii) supporting a fluid connector by the other of the first housing portion and the second housing portion in a position to engage the reservoir in a case where the reservoir is supported by the one of the first housing portion and the second housing portion and the first housing portion and the second housing portion are slid relative to each other to operatively engage each other.

A medical device for treating a user may include, but is not limited to, a first housing portion, a second housing portion, a plurality of electrical contacts, a shorting mechanism, and circuitry. The first housing portion may be adapted to be carried by a user. The second housing portion may be configured to be selectively operatively engaged with and disengaged from the first housing portion. The plurality of electrical contacts may be provided on at least one of the first housing portion and the second housing portion. The plurality of electrical contacts may include a set of main electrical contacts and at least one other electrical contact.

The shorting mechanism may be provided on the other of the first housing portion and the second housing portion. The shorting mechanism may be for interacting with the set of main electrical contacts. The circuitry may be configured to provide a first signal in a case where the first housing portion and the second housing portion are brought together and the shorting mechanism interacts with the set of main electrical contacts of the plurality of electrical contacts. The circuitry may be further configured to provide a second signal in a case where the first housing portion and the second housing portion are brought together and the shorting mechanism interacts with the at least one other electrical contact of the plurality of electrical contacts.

In some embodiments, the first signal may indicate that the first housing portion and the second housing portion have been connected. In further embodiments, the second signal may indicate that the first housing portion and the second housing portion have not been connected.

In some embodiments, the set of main electrical contacts may interact with the shorting mechanism in a case where the shorting mechanism contacts the set of main electrical contacts. The circuitry may be configured to provide the first signal in a case where the first housing portion and the second housing portion are brought together and the shorting mechanism contacts the set of main electrical contacts of the plurality of electrical contacts. The circuitry may be further configured to provide the second signal in a case where the first housing portion and the second housing portion are brought together and the shorting mechanism contacts the at least one other electrical contact of the plurality of electrical contacts.

In some embodiments, the shorting mechanism may have a plurality of ends. Each of the ends may be for interacting with a respective main electrical contact of the set of main electrical contacts. The circuitry may be configured to provide the first signal in a case where the first housing portion and the second housing portion are brought together and each of the ends of the shorting mechanism interacts with the respective main electrical contact of the set of main electrical contacts. The circuitry may be further configured to provide the second signal in a case where the first housing portion and the second housing portion are brought together and at least one of the ends of the shorting mechanism interacts with the at least one other electrical contact of the plurality of electrical contacts.

In further embodiments, the set of main electrical contacts may include a first main electrical contact and a second main electrical contact. The plurality of ends of the shorting mechanism may include a first end and a second end for interacting with the first main electrical contact and the second main electrical contact.

The circuitry may be configured to provide the first signal in a case where the first housing portion and the second housing portion are brought together and the first end and the second end of the shorting mechanism interacts with the first main electrical contact and the second main electrical contact of the plurality of electrical contacts. The circuitry may be further configured to provide the second signal in a case where the first housing portion and the second housing portion are brought together and at least one of the first end and the second end of the shorting mechanism interacts with the at least one other electrical contact of the plurality of electrical contacts. In yet further embodiments, the shorting mechanism may have a first end and a second end for interacting only with the first main electrical contact and the second main electrical contact respectively.

In some embodiments, at least one of the at least one other electrical contact may be arranged between the set of main electrical contacts. In some embodiments, the circuitry may be further configured to provide a third signal in a case where the first housing portion and the second housing portion are brought together and the shorting mechanism does not interact with the set of main electrical contacts of the plurality of electrical contacts. In further embodiments, the third signal may indicate that the first housing portion and the second housing portion have not been connected. In further embodiments, the second signal and the third signal may be a same type of signal.

In some embodiments, at least some of the set of main electrical contacts may be arranged to be outermost electrical contacts of the plurality of electrical contacts. In some embodiments, all of the at least one other electrical contact may be arranged in between the set of main electrical contacts.

In some embodiments, the shorting mechanism may be configured to establish an electrical connection between the set of main electrical contacts in a case where the shorting mechanism interacts with the set of main electrical contacts. In further embodiments, the shorting mechanism may comprise an electrical conductor. In some embodiments, the set of main electrical contacts may be configured to be biased toward a first position and urgeable to a second position from the first position. The set of main electrical contacts may be configured to be moved to the second position when the first housing portion is engaged with the second housing portion.

In further embodiments, the device may include a bias member for biasing the set of main electrical contacts toward the first position. In yet further embodiments, the bias member may comprise a spring. In yet further embodiments, the bias member may comprise individual bias members. Each of the individual bias members may be for biasing one of the set of main electrical contacts toward the first position.

In some embodiments, the plurality of the electrical contacts may be configured to be biased toward a first position and urgeable to a second position from the first position. The plurality of electrical contacts may be moved to the second position when the first housing portion is engaged with the second housing portion.

In some embodiments, the shorting mechanism may be configured to be biased toward a first position and urgeable to a second position from the first position. The shorting mechanism may be configured to be moved to the second position when the first housing portion is engaged with the second housing portion. In some embodiments, one of the first housing portion and the second housing portion may be for supporting a reservoir having an interior volume for containing fluidic media. In some embodiments, each of the main electrical contacts of the set of main electrical contacts may comprise a conductive pad.

In some embodiments, the plurality of electrical contacts may be provided in the second housing portion. The second housing portion may have a power source for providing power to electronics in the second housing portion. At least some of the plurality of electrical contacts may be configured to be engageable with an electrical source for charging the power source in the second housing portion.

In some embodiments, the plurality of electrical contacts may be provided in the second housing portion. The second housing portion may have programmable circuitry. At least some of the plurality of electrical contacts may be configured to be engageable with an input device for programming the programmable circuitry in the second housing portion. In some embodiments, the plurality of electrical contacts may be provided in the second housing portion. The circuitry may be configured to determine a type of the second housing portion based on one of the plurality of electrical contacts and the shorting mechanism of the first housing portion. In various embodiments, the shorting mechanism may comprise a known resistance.

A method of making a medical device may include, but is not limited to, any one of or combination of: (i) adapting a first housing portion to be carried by a user; (ii) configuring a second housing portion to be selectively operatively engaged with and disengaged from the first housing portion; (iii) providing a plurality of electrical contacts on at least one of the first housing portion and the second housing portion, the plurality of electrical contacts including a set of main electrical contacts and at least one other electrical contact; (iv) providing a shorting mechanism on the other of the first housing portion and the second housing portion, the shorting mechanism for interacting with the set of main electrical contacts; (v) configuring circuitry to provide a first signal in a case where the first housing portion and the second housing portion are brought together and the shorting mechanism interacts with the set of main electrical contacts of the plurality of electrical contacts; and (vi) configuring the circuitry to provide a second signal in a case where the first housing portion and the second housing portion are brought together and the shorting mechanism interacts with the at least one other electrical contact of the plurality of electrical contacts.

A medical device for treating a user may include, but is not limited to, a first housing portion, a second housing portion, a magnetic source, sensor, and circuitry. The first housing portion may be adapted to be carried by a user. The second housing portion may be configured to be selectively operatively engaged with and disengaged from the first housing portion. The magnetic source may have at least one of a certain magnetic field and a certain magnetic strength provided on at least one of the first housing portion and the second housing portion.

The sensor may be for detecting at least one of the certain magnetic field and the certain magnetic strength provided on the other of the first housing portion and the second housing portion. The circuitry may be configured to provide a first signal in a case where the first housing portion and the second housing portion are brought together and the sensor detects at least one of the certain magnetic field and the certain magnetic strength of the magnetic source. The circuitry may be further configured to provide a second signal in a case where the first housing portion and the second housing portion are brought together and the sensor detects at least one of a magnetic field different from the certain magnetic field and a magnetic strength different from the certain magnetic strength of the magnetic source.

In some embodiments, the sensor may be configured to provide a signal for activating control circuitry in a case where the sensor detects a gauss level exceeding a first pre-defined threshold value. In further embodiments, the sensor may comprise a magnetic threshold switch. In further embodiments, the device may further include a second magnetic threshold switch configured to provide a signal for deactivating at least one of the control circuitry and the sensor in a case where the sensor detects a gauss level exceeding a second pre-defined threshold value. The second pre-defined threshold value may be greater than the first pre-defined threshold value.

In some embodiments, the magnetic source may have a certain magnetic field direction. The sensor may be for detecting the certain magnetic field direction. The circuitry may be configured to provide the first signal in a case where the first housing portion and the second housing portion are brought together and the sensor detects the certain magnetic field direction. In further embodiments, the circuitry may be further configured to provide the second signal in a case where the first housing portion and the second housing portion are brought together and the sensor detects a magnetic field direction different from the certain magnetic field direction. In various embodiments, the certain magnetic field may include a direction. The sensor may be configured for detecting the direction.

A method of making a medical device may include, but is not limited to, any one of or combination of: (i) adapting a first housing portion to be carried by a user; (ii) configuring a second housing portion to be selectively operatively engaged with and disengaged from the first housing portion; (iii) providing a magnetic source having at least one of a certain magnetic field and a certain magnetic strength on at least one of the first housing portion and the second housing portion; (iv) providing a sensor for detecting at least one of the certain magnetic field and the certain magnetic strength on the other of the first housing portion and the second housing portion; (v) configuring circuitry to provide a first signal in a case where the first housing portion and the second housing portion are brought together and the sensor detects at least one of the certain magnetic field and the certain magnetic strength of the magnetic source; and (vi) configuring the circuitry to provide a second signal in a case where the first housing portion and the second housing portion are brought together and the sensor detects at least one of a magnetic field different from the certain magnetic field and a magnetic strength different from the certain magnetic strength of the magnetic source.

BRIEF DESCRIPTION OF THE DRAWINGS

FIG. 5A illustrates a durable portion of a delivery device in accordance with an embodiment of the present invention;

FIG. 5B illustrates a section view of a durable portion of a delivery device in accordance with an embodiment of the present invention;

FIG. 5C illustrates a section view of a durable portion of a delivery device in accordance with an embodiment of the present invention;

FIGS. 20A-20C illustrate a cutaway view of a portion of medical device system in accordance with an embodiment of the present invention;

FIGS. 22A-22C illustrate a portion of medical device system in accordance with an embodiment of the present invention;

FIG. 24 illustrates a portion of a medical device system in accordance with an embodiment of the present invention;

FIGS. 25A and 25B illustrate a portion of a medical device system in accordance with an embodiment of the present invention;

FIGS. 26A and 26B illustrate a portion of a medical device system in accordance with an embodiment of the present invention;

FIGS. 27A-27C illustrate a medical device system in accordance with an embodiment of the present invention;

FIGS. 28A-28C illustrate a medical device system in accordance with an embodiment of the present invention;

FIGS. 31A-31C illustrate a general representation of a medical device system in accordance with an embodiment of the present invention;

FIG. 32 illustrates a general representation of a medical device system in accordance with an embodiment of the present invention;

FIGS. 33A and 33B illustrate a general representation of a medical device system in accordance with an embodiment of the present invention;

FIGS. 34A and 34B illustrate a general representation of a medical device system in accordance with an embodiment of the present invention;

FIGS. 35A and 35B illustrate a general representation of a medical device system in accordance with an embodiment of the present invention; and FIG. 36 illustrates a block diagram of an electrical configuration of a medical device system in accordance with an embodiment of the present invention.

DETAILED DESCRIPTION OF THE PREFERRED EMBODIMENTS

Figure 1:
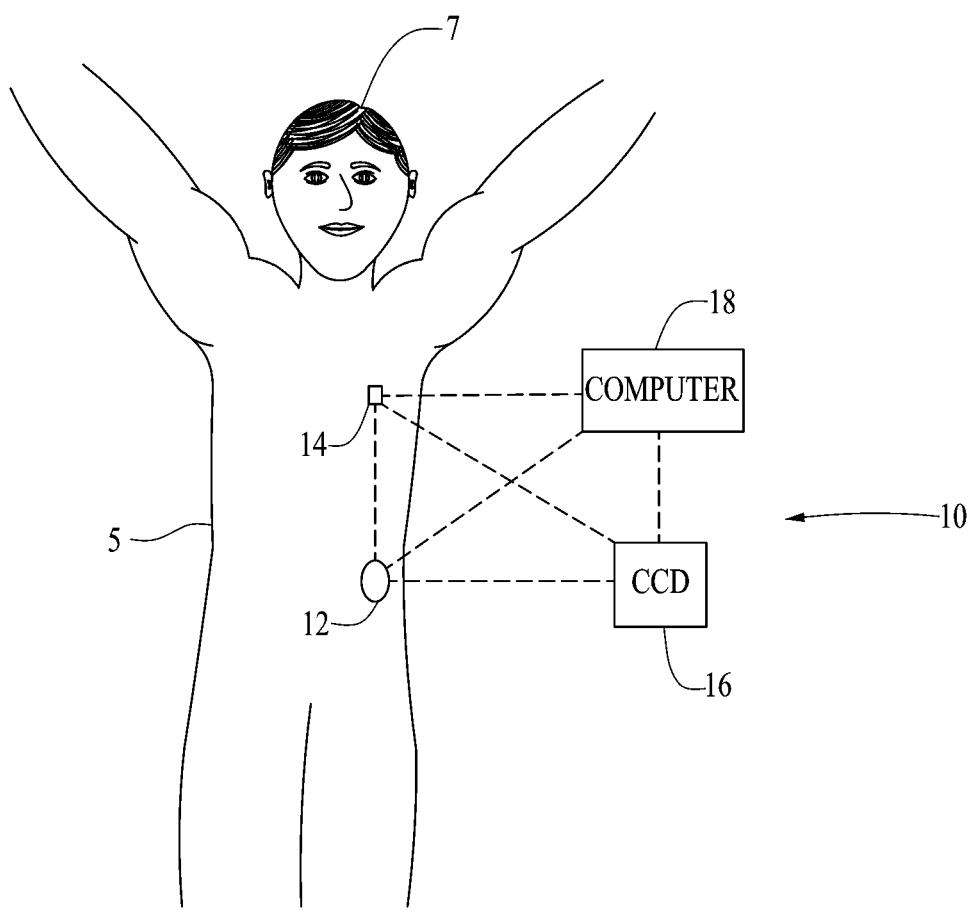
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples. It should be noted user-patient as used throughout the disclosure may include patient-user, patient, or user (e.g., a patient, a medical professional, or other treating the patient).

The system 10, the delivery device 12, the sensing device 14, the CCD 16, and computer 18 may be similar to those described in the following U.S. Patent Applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxi) U.S. patent application Ser. No. 10/180,732, filed Jun. 26, 2002, "Communication Station And Software For Interfacing With An Infusion Pump, Analyte Monitor, Analyte Meter, And/or the like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional App. Ser. No. 61/044,269, filed Apr. 11, 2008, "Reservoir Plunger Head Systems And Methods"; (xxxvii) U.S. Patent App. Ser. No. 61/044,292, filed Apr. 11, 2008, "Reservoir Barrier Layer Systems And Methods"; (xxxviii) U.S. Patent Provisional App. Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S. patent application Ser. No. 12/360,813, filed Jan. 27, 2009, "Multi-Position Infusion Set Device And Process." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S.

patent application Ser. No. 09/360,342, filed Jul. 22, 1999, entitled "Substrate Sensor"; and (viii) U.S. Provisional Patent App. Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
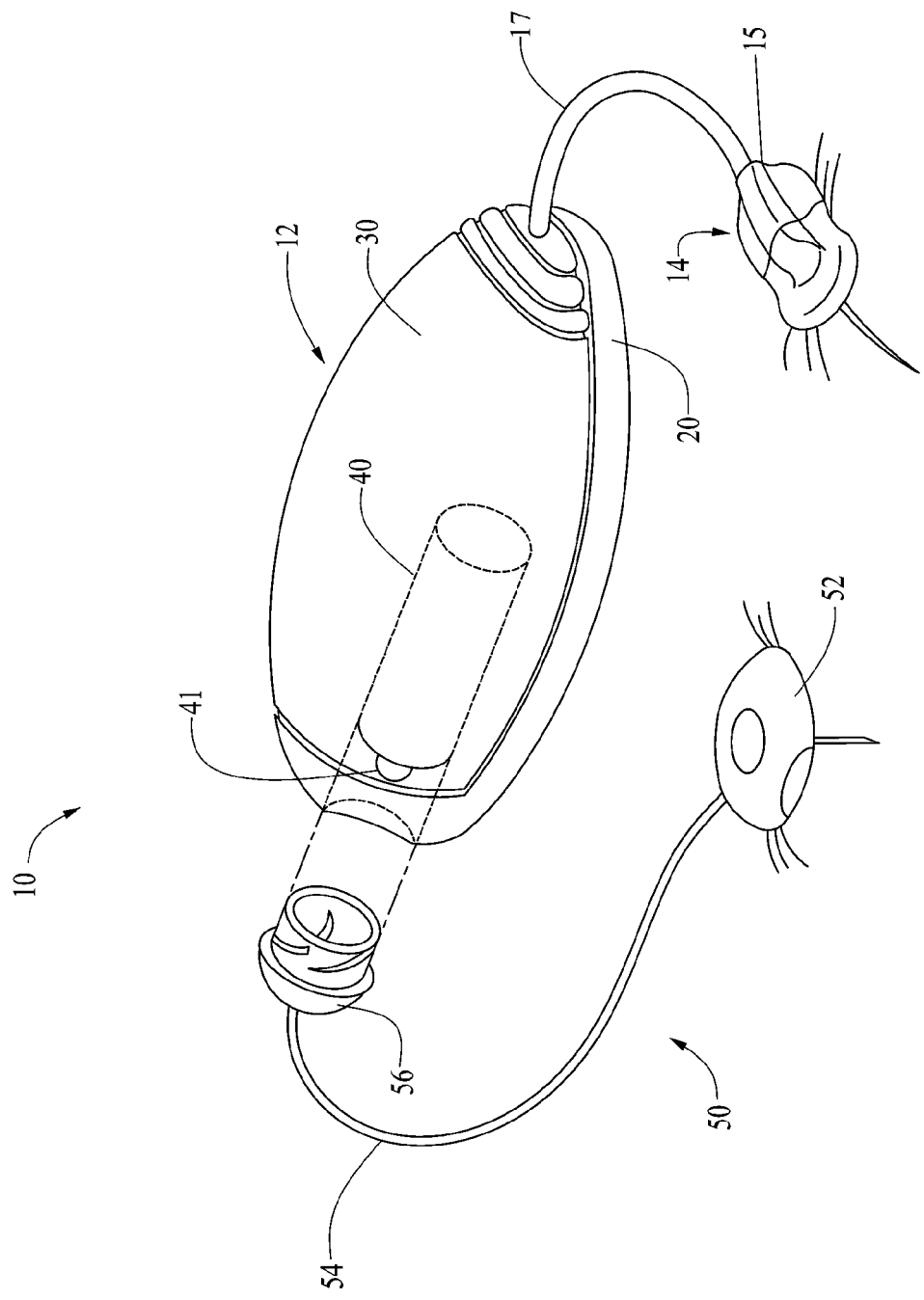
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, in a friction fit connection, in a slidable connection, and/or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2) that may include a motor and a drive device linkage portion. The drive device may be configured to apply a force to fluidic media within the reservoir system 40 to force fluidic media out of the reservoir system 40 and into an infusion path, such as the infusion path 50, for delivery to a user-patient. For example, in some embodiments, an electrically-driven motor 84 (refer to FIGS. 5B and 5C) may be mounted within the durable housing 30 with appropriate linkage for operatively coupling the motor 84 to a plunger arm (refer to FIGS. 6A-6C) connected to a plunger head (refer to FIGS. 6A-6C) arranged within the reservoir system 40. The electrically-driven motor may be configured to drive the plunger head in a direction to force fluidic media out of the port 41 of the reservoir system 40 and to the user-patient.

Also, in some embodiments, the motor 84 may be controllable to reverse direction to move the plunger arm 60 and the plunger head to cause fluid to be drawn into the reservoir system 40 from a patient. The motor 84 may be arranged within the durable housing 30 and the reservoir system 40 may be correspondingly arranged on the disposable housing 20, such that the operable engagement of the motor 84 with the plunger head, through the appropriate linkage, occurs automatically upon the user-patient connecting the durable housing 30 with the disposable housing 20 of the delivery device 12. Further examples of linkage and control structures may be found in, but are not limited to, U.S. patent application Ser. No. 09/813,660, filed Mar. 21, 2001, entitled "Control Tabs for Infusion Devices and Methods of Using the Same"; U.S. Patent Pub. No. 2006/0264894 (Ser. No. 11/211,095), filed Aug. 23, 2005, entitled "Infusion Device and Method with Disposable Portion"; U.S. patent application Ser. No. 11/210,467, filed Aug. 23, 2005, entitled "Infusion Device and Method With Drive In Separable Durable Housing Portion"; U.S. patent application Ser. No. 11/211,150, filed Aug. 23, 2005, entitled "Pump Assembly and Method For Infusion Device"; U.S. patent application Ser. No. 11/210,455, filed Aug. 23, 2005, entitled "Reservoir Support And Method For Infusion Device"; and U.S. Pat. No. 6,485,465, filed Mar. 27, 2001, entitled "Methods, Apparatuses, and Uses for Infusion Pump Fluid Pressure and Force Detection," all of which are incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
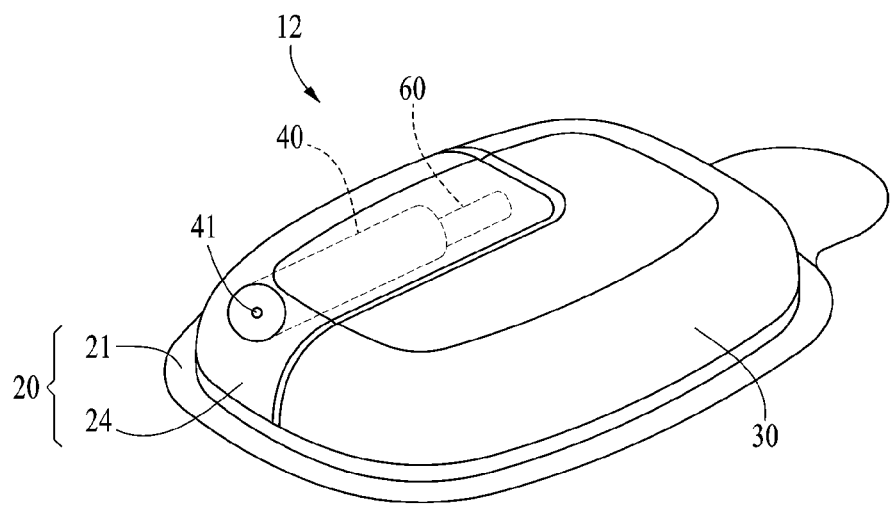
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
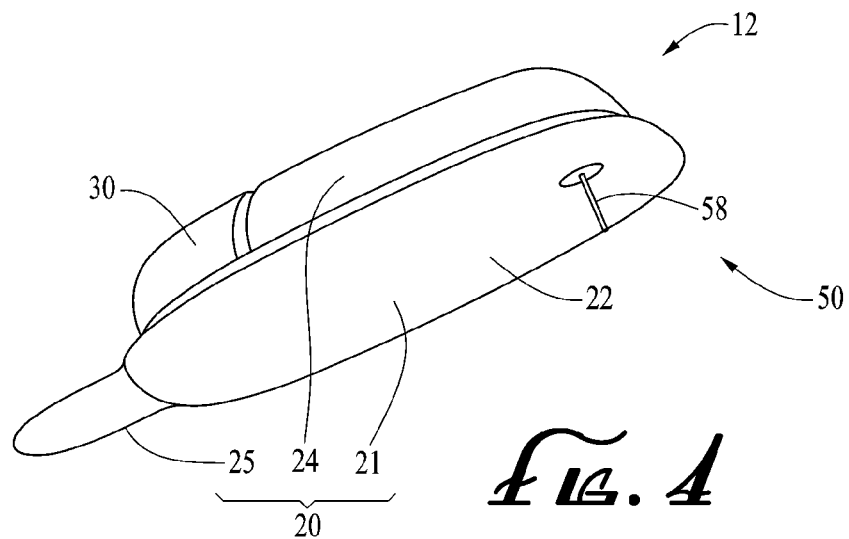
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place with one end of the cannula located within the body of the user-patient and the other end of the cannula in fluid flow connection with fluidic media within the reservoir system 40. Accordingly, fluidic media may be conveyed from the reservoir system 40 to the body of the user-patient.

FIG. 5A illustrates a durable portion 8 of the delivery device 12 (e.g., FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (e.g., FIG. 3).

Figure 6A:
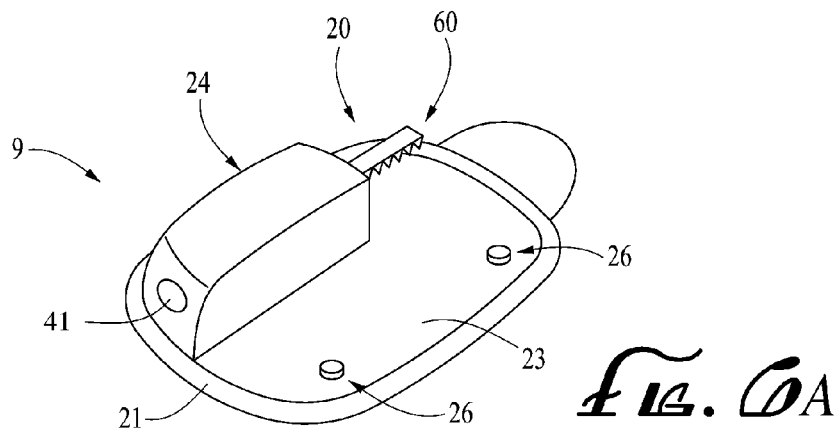
FIG. 6A illustrates a disposable portion of a delivery device in accordance with an embodiment of the present invention.
Figure 6B:
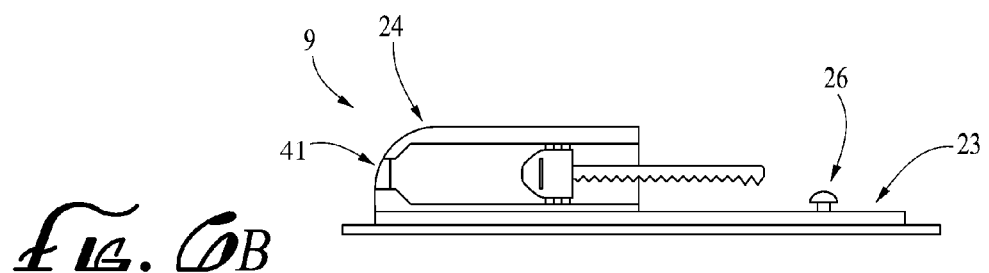
FIG. 6B illustrates a section view of a disposable portion of a delivery device in accordance with an embodiment of the present invention.
Figure 6C:
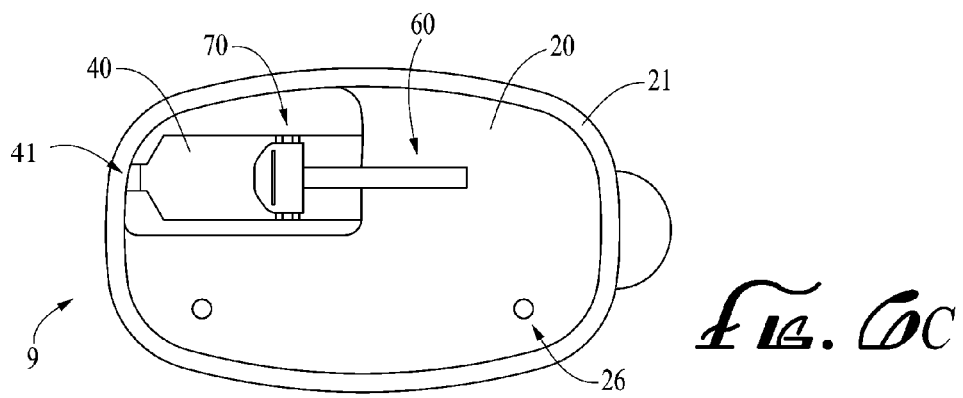
FIG. 6C illustrates a section view of a disposable portion of a delivery device in accordance with an embodiment of the present invention.

FIG. 6A illustrates a disposable portion 9 of the delivery device 12 (e.g., FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. The plunger head 70 may be made of Bromobutyl rubber, silicone rubber, or any other suitable material and/or any derivative thereof. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (e.g., FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (e.g., FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82. Accordingly, the plunger arm 60 may be moved to cause the plunger head 70 to move within the reservoir system 40. When the interior volume of the reservoir system 40 is sufficiently filled with fluidic media and an infusion path is provided from the reservoir system 40 to the body of the user-patient, the plunger head 70 may be moved within the reservoir system 40 to force fluidic media from the reservoir system 40 to the user-patient via the infusion path.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (e.g., FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; (iv) an amount of contents in the reservoir system 40; or the like. In some embodiments, the delivery device 12 may include the reservoir status circuitry, and the reservoir status circuitry may be configured to read data from the reservoir circuitry when the reservoir system 40 is inserted into the disposable portion 9.

In various embodiments, the reservoir status circuitry may be further configured to store data to the reservoir circuitry after at least some of the contents of the reservoir system 40 have been transferred out of the reservoir system 40 to update information in the reservoir circuitry. Such information may be related to, but is not limited to, an amount of fluidic media remaining in the reservoir system 40, an amount of fluidic media already delivered, plunger head 60 location, pressure within the reservoir system, or the like.

In some embodiments, the reservoir status circuitry may be configured to store data to the reservoir circuitry to update information in the reservoir circuitry related to an amount of contents remaining in the reservoir system 40 when the reservoir system 40 is inserted into the disposable portion 9. In some embodiments, the delivery device 12 may include the reservoir status circuitry and the reservoir system 40 may include the reservoir circuitry, and the reservoir status circuitry may selectively inhibit use of the delivery device 12 or may selectively provide a warning signal based on information read by the reservoir status circuitry from the reservoir circuitry.

FIGS. 7-19 illustrate various examples of connection structures for connecting a first housing portion and a second housing portion of a medical device system according to various embodiments of the present invention. The medical device systems of FIGS. 7-19 may include features similar to the medical device systems discussed throughout the disclosure or employed as an embodiment of the medical devices (e.g., delivery device 12 in FIGS. 1-6C) discussed throughout the disclosure. Although the medical device systems may include features similar or used with the embodiments of FIGS. 1-6C, it should be understood that the medical device systems may also include some or all of the same features and operate in a manner similar to that shown and described in the embodiments of FIGS. 20-36. In addition, some or all of the features shown in FIGS. 1-6C and 20-36 may be combined in various ways and included in the embodiments shown in FIGS. 7-19. Likewise, it should be understood that any of the features of the embodiments of FIGS. 7-19 may be combined or otherwise incorporated into any of the other embodiments of FIGS. 7-19 as well as any other embodiment herein discussed.

Figure 7:
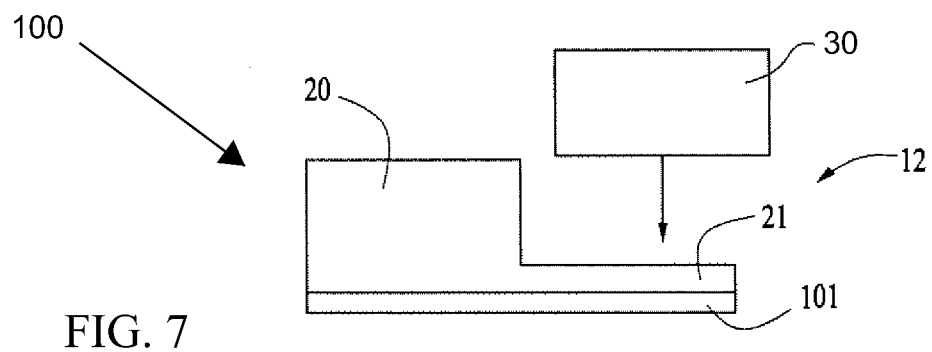
FIG. 7 shows a schematic side view of an arrangement of a durable housing portion and a disposable housing portion of a delivery system in accordance with an embodiment of the present invention.

In various embodiments, a medical device system 100 having a disposable housing portion (e.g., 20 in FIG. 3) may be provided with a base portion 21 that may be secured to skin of a patient-user by, for example, but not limited to, an adhesive material, such as that described herein, provided on a bottom surface of the base portion 21. That arrangement is generally represented in side view in FIG. 7. In such an arrangement, an adhesive material 101 may be provided on a bottom surface (i.e., skin-facing surface) of the base 21 of the disposable housing portion 20. With reference to FIGS. 2, 3, and 7, a durable housing portion 30 may be configured to be arranged on the base 21 of the disposable housing portion 20 to engage and connect to the base 21 and the disposable housing portion 20. In such an arrangement, the base 21 may be disposed between the durable housing portion 30 and the skin of the patient-user such that only the base 21 of the disposable housing portion 20 remains in contact with the skin of the patient-user.

Figure 8:
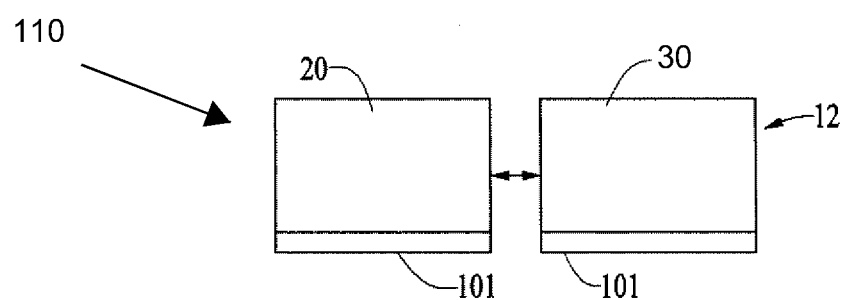
FIG. 8 shows a schematic side view of an arrangement of a durable housing portion and a disposable housing portion of a delivery system in accordance with an embodiment of the present invention.

However, in other embodiments, a durable housing portion 30 and a disposable housing portion 20 of a medical device system 110 may be configured to engage each other in a side-by-side arrangement, for example, as represented in FIG. 8. In the side-by-side arrangement in FIG. 8, either one or both of the durable housing portion 30 and the disposable housing portion 20 may be provided with a base having an adhesive material 101 (with or without a peelable cover layer 23 as shown in FIG. 3).

Figure 9:
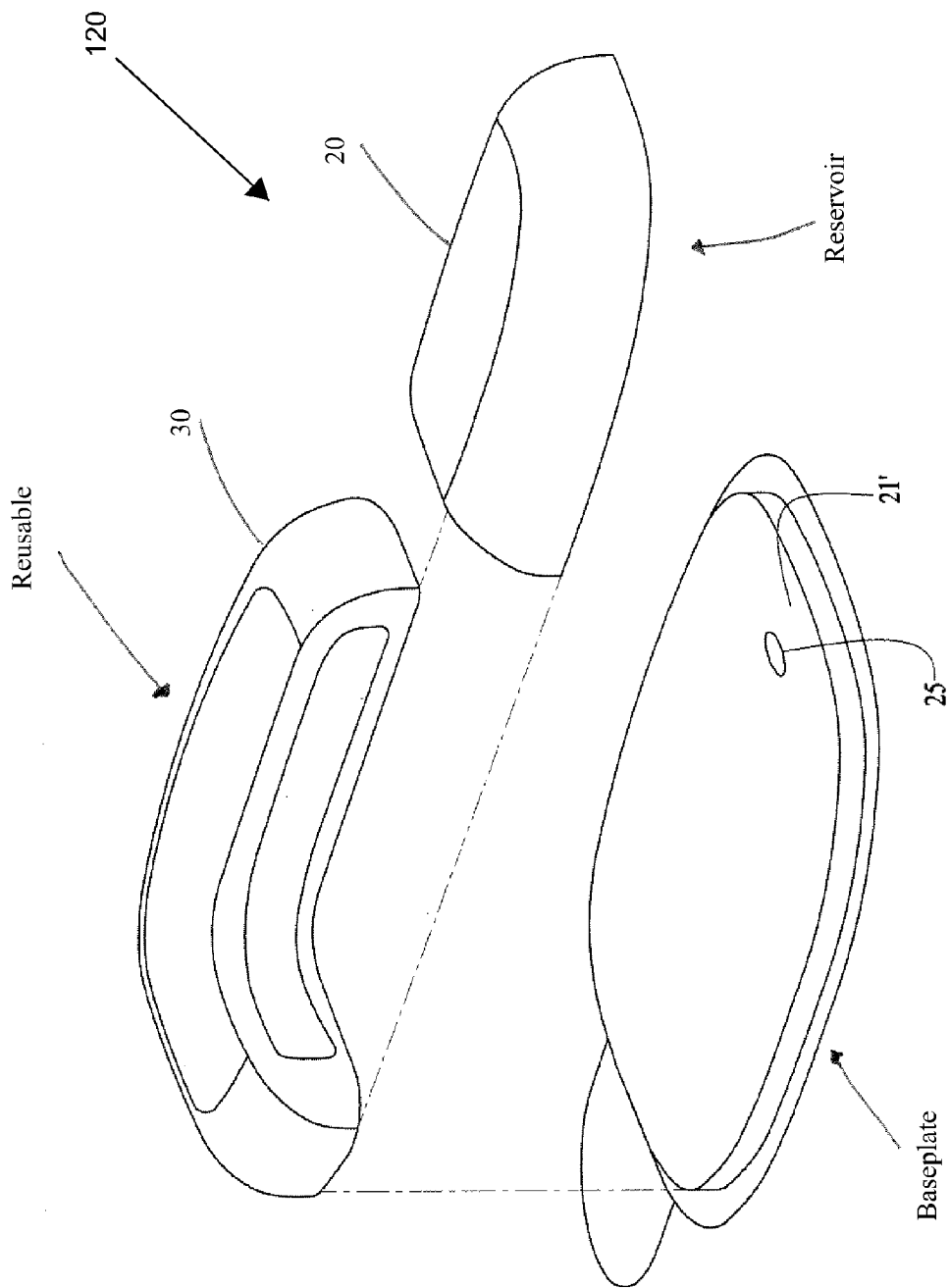
FIG. 9 shows a partially exploded view of a delivery system in accordance with an embodiment of the present invention.

In yet further embodiments, for example, as represented in FIG. 9, one or both of a durable housing portion 30 and a disposable housing portion 20 of a medical device system 120 may be attachable and detachable from a separate base member 21'. A suitable connecting structure, such as that described above, may be employed for connecting any combination or all of the durable housing portion 30, the disposable housing portion 20, and the base member 21'. The separate base member 21' may include a generally flat, plate-like structure made of any suitably rigid material including, but not limited to, plastic, metal, ceramic, composite material, or the like. The base member 21' may have a surface (i.e., upper-facing surface in FIG. 9) to which the disposable housing portion 20 and the durable housing portion 30 may be attached or otherwise operatively engaged. The base member 21' may have a second surface (i.e., lower-facing surface in FIG. 9) to which an adhesive material and a peelable cover film may be applied, as described herein, to allow the base member 21' to be secured to a skin of a patient-user.

In some embodiments, the base member 21' may include a needle inserter device 25, as described herein. In such embodiments, the base member 21' may be secured to skin of a patient-user. Then, the needle inserter 25 may be activated to insert a hollow needle or cannula into the skin of the patient-user. Then, after the hollow needle or cannula is inserted, the durable housing portion 30 and the disposable housing portion 20 may be attached to the base member 21' to connect the reservoir system 40 (e.g., FIGS. 1-6C) in fluid flow communication with the hollow needle or cannula.

In some embodiments, the durable housing portion 30 and the disposable housing portion 20 may be connected together, for example, in the manner described above, before attaching those housing portions to the base member 21'. In further embodiments, one of the durable housing portion 30 and the disposable housing portion 20 may be attached to the base member 21' before the durable housing portion 30 and the disposable housing portion 20 are connected together. In such further embodiments, the needle inserter device may be activated to insert a hollow needle or cannula into the skin of the patient-user after the disposable housing portion 20 is attached to the base member 21' either before or after the durable housing portion 30 and the disposable housing portion 20 are connected together.

In some embodiments, the base member 21' may have an opening 25 that aligns with a needle inserter device (or aligns with a further opening). In such embodiments, the base member 21' may be secured to the skin of the patient-user. Then the disposable housing portion 20 may be attached to the base member 21' before or after the durable housing portion 30 and the disposable housing portion 20 are connected together. Once the disposable housing portion 20 is attached to the base member 21', the needle inserter device may be activated to insert a hollow needle or cannula into skin of a patient-user either before or after the durable and disposable housing portions are connected together. Other needle/cannula insertion tools, as described throughout the disclosure, may be used (or modified for use) to insert a needle and/or cannula, such as, but not limited to, those previously described.

Figure 10:
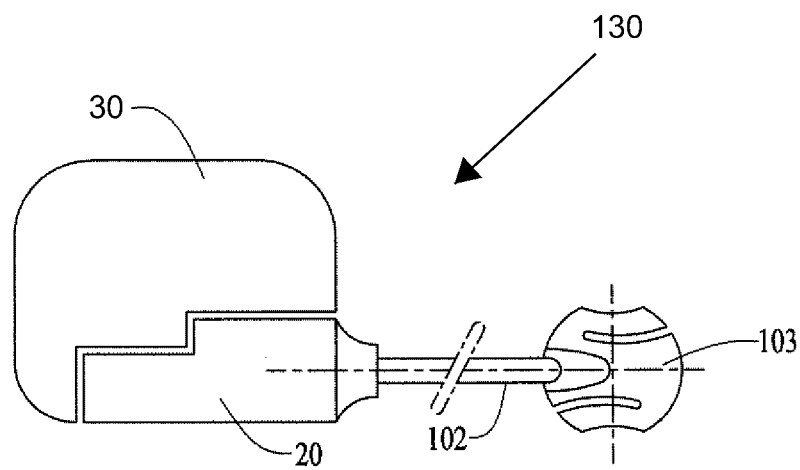
FIG. 10 shows a schematic top view of an arrangement of a durable housing portion and a disposable housing portion of a delivery system in accordance with an embodiment of the present invention.

In some embodiments, an injection site module 103 may be provided external to a disposable housing portion 20 of a medical device system 130, but connected to the disposable housing portion 20 through a conduit 102, as shown in FIG. 10. The external injection site module 103 may include a needle or cannula injector device structure and an operator or opening (e.g., opening 25 in FIG. 9) through which such an injector device or the like may be activated. Alternatively or in addition, the external injection site module 103 may include an infusion set such as, but not limited to an infusion set as described or referenced in U.S. patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and incorporated herein by reference in its entirety.

The conduit 102 that connects the injection site module 103 with the disposable housing portion 20 may be any suitable tubing structure having a fluid flow passage, such as, but not limited to, a flexible tube made of plastic, silicone, polymers, or the like. An adhesive material, such as the adhesive material previously described, may be provided on the tubing structure (or between the tubing structure and the skin of the patient-user) to secure the tubing to the skin of the patient-user. An adhesive material, such as the adhesive material previously described, may be provided on the injection site module 103 (or between the injection site module 103 and the skin of the patient-user) to secure the injection site module 103 to the skin of the patient-user. By locating the injection site module 103 external to the disposable housing portion 20, the disposable housing portion 20 and the durable housing portion 30 may be clipped to clothing, belt, suspender, or other article of apparel or may be held in a pocket of an article of apparel or carried in a purse, or the like of the patient-user.

In some embodiments, the conduit 102 may be fixed at one end to the disposable housing portion 20 in fluid-flow communication with the reservoir system 40 (e.g., FIGS. 1-6C) within the disposable housing portion 20. The conduit 102 may be fixed at a second end to the external injection site module 103 for connection in fluid-flow communication with a hollow needle or cannula, as previously described.

In further embodiments, one or both of the ends of the conduit 102 may include suitable connection structures that allow the ends of the conduit 102 to be selectively connected in fluid-flow communication with and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and a durable housing portion 30 may be disconnected from the injection site module 103, for example, by disconnecting one of the ends of the conduit 102 from the injection module 103 or the disposable housing portion 20, while leaving the injection site module 103 in place. Thus, the patient-user may not need to withdraw the needle or cannula and, later, insert a needle or cannula to resume operation. In this manner, the patient-user may readily disconnect and remove the disposable housing portion 20 and durable housing portion 30, for example, to allow the patient-user to shower, bathe, swim, or conduct other activities, yet also allow the patient-user to readily re-connect the disposable housing portion 20 to the injection site module 103, for example, upon completion of such activities. Examples of connectors can be found in U.S. patent application Ser. No. 10/328,393, filed Dec. 22, 2003, and entitled "Reservoir Connector"; and U.S. Pat. No. 5,545,152 issued Aug. 13, 1996, and entitled "Quick-Connect Coupling For A Medication Infusion System," both of which are incorporated herein by reference in their entirety. In other alternatives, different connectors such as Luer locks, or other suitable fluid-communication connectors may be used.

Figure 11:
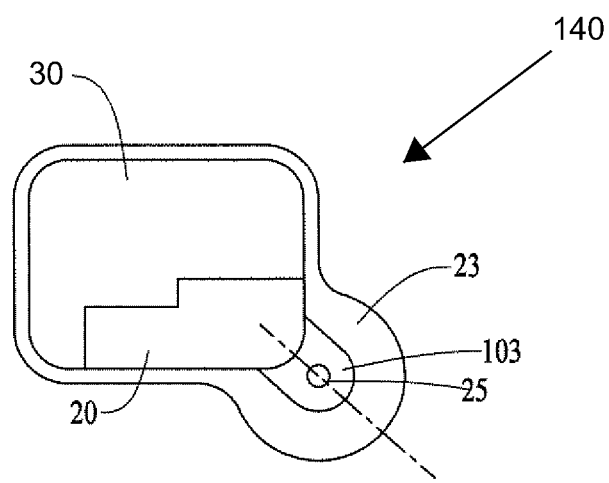
FIG. 11 shows a schematic top view of an arrangement of a durable housing portion and a disposable housing portion of a delivery system in accordance with an embodiment of the present invention.

In some embodiments, an injection site module 103 may be directly connected with a disposable housing portion 20 of a medical device system 140, as shown in FIG. 11. In such embodiments, one or more suitable fluid flow passages are provided through the disposable housing portion 20 and into the injection site module 103 for fluid-flow communication between the reservoir system 40 (e.g., FIGS. 1-6C) in the disposable housing portion 20 and a hollow needle or cannula, as previously described. In addition, in such embodiments, the injection site module 103 and the disposable housing portion 20 may include mating connection structures to allow the injection site module 103 and the disposable housing portion 20 to be selectively connected and disconnected from each other.

Figure 12:
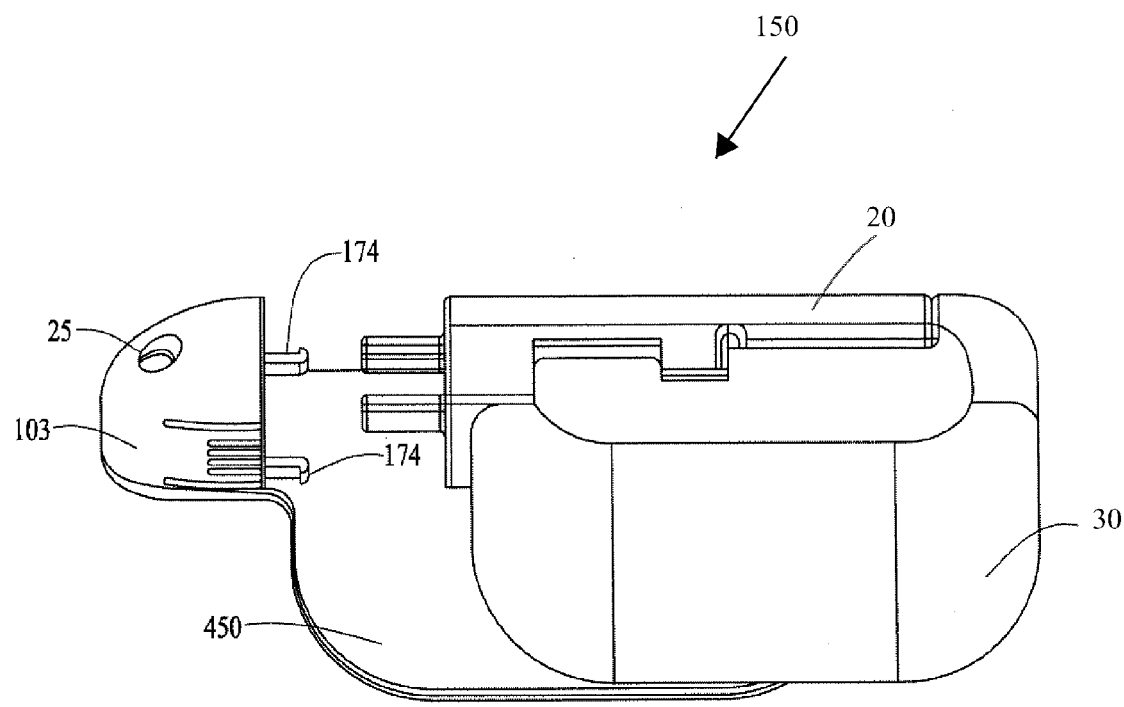
FIGS. 12 and 13 each show a perspective view of a connection arrangement for a disposable housing portion and an injection site module in accordance with an embodiment of the present invention.
Figure 13:
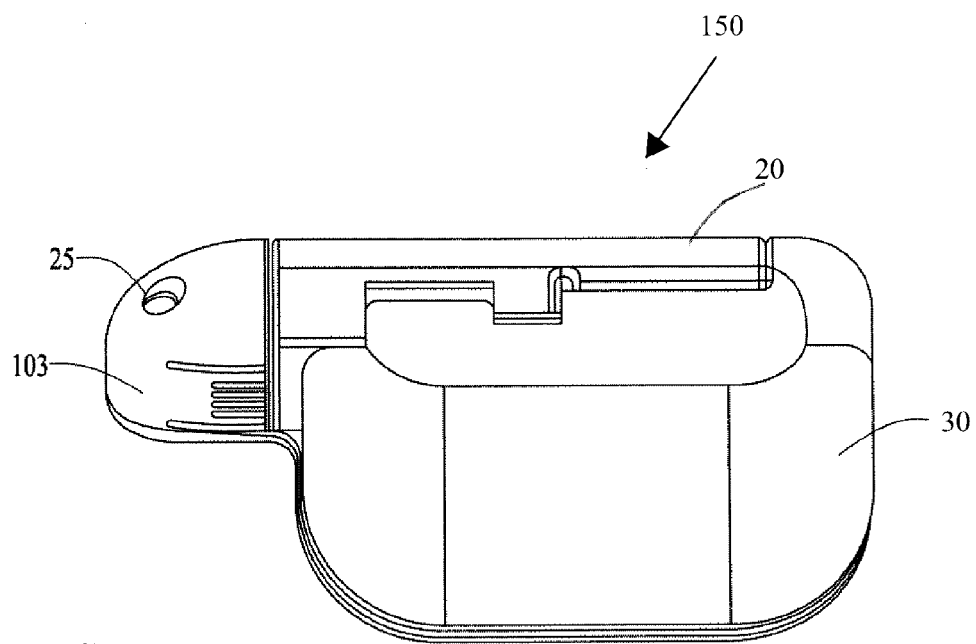
Figure 14:
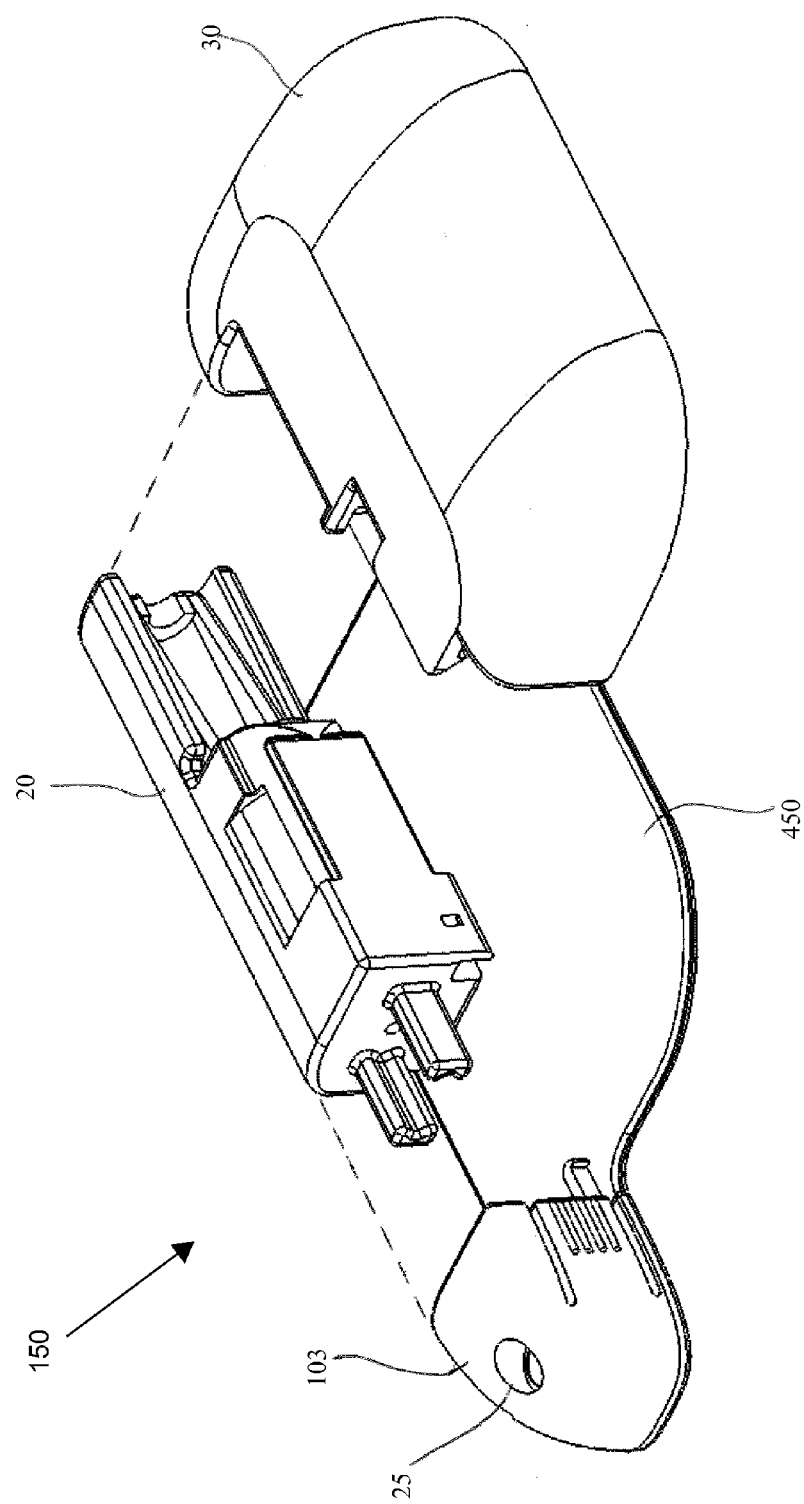
FIGS. 14 and 15 each show a perspective view of a connection arrangement for a disposable housing portion and an injection site module in accordance with an embodiment of the present invention.

Various examples of mating arrangements for directly connecting an injection site module 103 to a disposable housing portion 20 are described with reference to FIGS. 12-19. FIGS. 12-14 show an example arrangement of a medical device system 150 in which an injection site module 103 may include at least one (e.g., two in FIG. 12) protruding engagement pawl(s) 174 that are configured to be received in a corresponding number of receptacle(s) on the disposable housing portion 20. The pawl(s) 174 and the receptacle(s) may, for example, be similar to the pawls 74 and receptacles 76 described in U.S. Patent Application No. 60/839,741, titled INFUSION PUMPS AND METHODS AND DELIVERY DEVICES AND METHODS WITH SAME, filed Aug. 23, 2006, which is herein incorporated by reference in its entirety. In other embodiments, the pawl(s) 174 may be located on the disposable housing portion 20, while the corresponding receptacle(s) may be located on the injection site module 103. In yet other embodiments, each of the disposable housing portion 20 and the injection site module 103 may include one or more pawl(s) 174 and one or more receptacle(s).

The pawl(s) 174 and receptacle(s) may be configured to allow a patient-user to manually slide the pawl(s) 174 into the receptacle(s) as the disposable housing portion 20 and the injection site module 103 are brought together. By sliding the pawl(s) 174 in the corresponding receptacle(s), the injection site module 103 may be secured to the disposable housing portion 20. The pawl(s) 174 may include a shaped portion or head to provide a snap-fit with the receptacle(s) when the pawl(s) 174 are fully received within the receptacle(s). The pawl(s) 174 may be configured with sufficient flexibility to allow the patient-user to separate the disposable housing portion 20 from the injection site module 103 by applying a sufficient force to pull those two parts away from each other and unsnap the pawl(s) 174 from the receptacle(s). In the embodiments of FIGS. 12-14, the injection site module 103 may be attached to or may include a base 450 that may be secured to skin of a patient-user during operation in lieu of the extended base 21 of the disposable housing portion 20 described above. The base 450 may include an adhesive material as described herein with respect to the base 21 (or any other base described herein) of the disposable housing portion 20.

As shown in FIG. 14, the embodiments of FIGS. 12-14 may be formed in three general parts, including the disposable housing portion 20, the durable housing portion 30, and the injection site module 103 on the base 450. The durable housing portion 30 and the disposable housing portion 20 may be secured together (e.g., FIG. 12), and the combined, connected disposable and durable housing portions may be secured to the injection site module 103 and the base 450. In some embodiments, the base 450 may be secured to the skin of the patient-user, before the combined, connected disposable and durable housing portions are secured to the injection site module 103 and the base 450. In further embodiments, the combined, connected disposable and durable housing portions may be secured to the injection site module 103 and the base 450, before the base 450 is secured to the skin of the patient-user.

Figure 15:
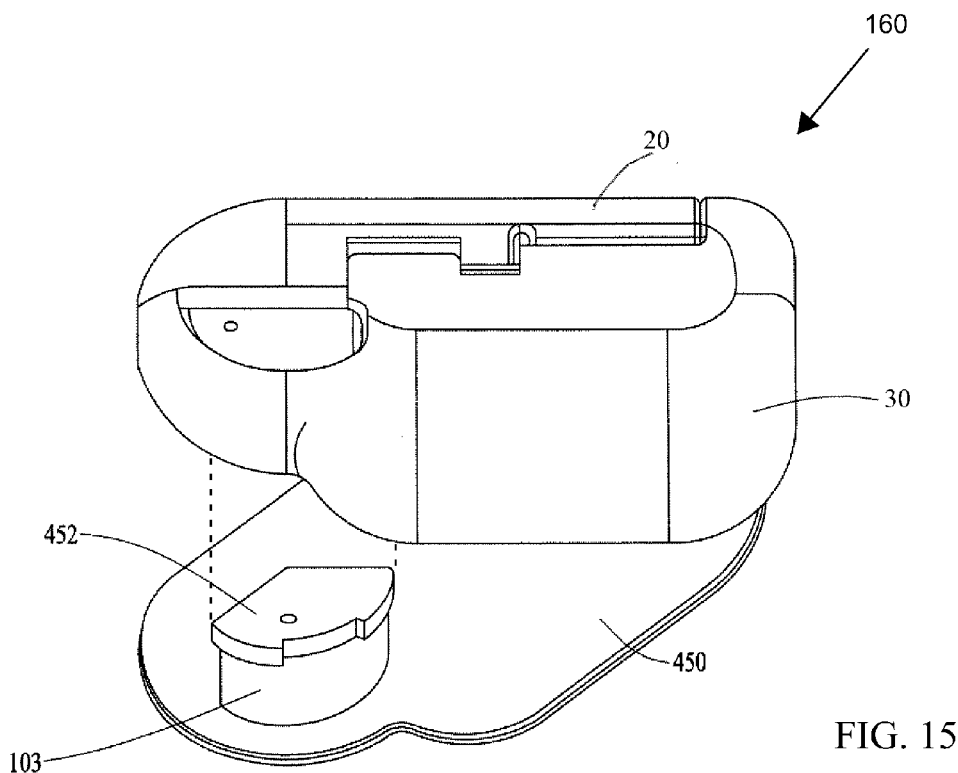

An example of a connection structure of a medical device system 160 is described with reference to FIGS. 15 and 16, wherein the injection site module 103 may include a shaped head 452 configured to be received within a correspondingly shaped opening or receptacle in the disposable housing portion 20. The shaped head 452 may be configured with a shape that allows the head 452 to be received in the receptacle in a case where the disposable housing portion 20 is aligned relative to the injection site module 103 in a first alignment position, as shown in FIG. 15.

Figure 16:
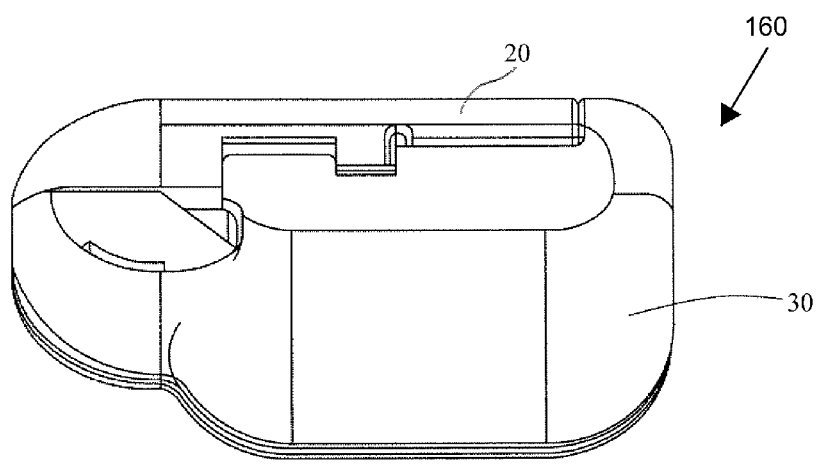
FIGS. 16-19 each show a perspective view of a connection arrangement for a disposable housing portion and an injection site module in accordance with an embodiment of the present invention.

The shaped head 452 may be further configured to allow the disposable housing portion 20 to be rotated relative to the injection site module 103 while the head 452 is received within the receptacle to a second alignment position, as shown in FIG. 16. The receptacle in the disposable housing portion 20 may be shaped to allow the head 452 to be freely received or removed from the receptacle when the disposable housing portion 20 is in the first alignment position (e.g., FIG. 15), yet abut the head 452 and inhibit separation of the head 452 from the receptacle in a case where the disposable housing portion 20 is in the second alignment position (e.g., FIG. 16). Accordingly, separation of the disposable housing portion 20 from the injection site module 103 may be inhibited in a case where the disposable housing 20 is in the second alignment position.

An example of a connection structure of a medical device system 170 is described with reference to FIGS. 17-19, wherein the medical device system 170 may incorporate three parts, the durable housing portion 30, the disposable housing portion 20, and a base 456. A shaped receptacle 454 on the base 456 may be configured to receive a correspondingly shaped connector member in the disposable housing portion 20. The injection site module 103 may be formed integral with the disposable housing portion 20. The shaped receptacle 454 may be configured with a shape that allows the connector member in the injection site module 103 to be engaged with the receptacle 454 in a case where the disposable housing portion 20 is aligned relative to the base 456 and receptacle 454 in a first alignment position, as shown in FIG. 17.

Returning to FIGS. 7-19, the shaped receptacle 454 may be further configured to allow the disposable housing portion 20 to be rotated relative to the base 456 and receptacle 454 in a case where the receptacle 454 is engaged within the connector member to a second alignment position, as shown in FIG. 18. Returning to FIGS. 7-19, the receptacle 454 and the connector member in the disposable housing portion 20 may be shaped to allow the connector member to freely engage the receptacle 454 in a case where the disposable housing portion 20 is in the first alignment position (e.g., FIG. 17), yet lock with the receptacle 454 and inhibit separation of the connector member from the receptacle in a case where the disposable housing portion 20 is in the second alignment position (e.g., FIG. 18). Accordingly, separation of the disposable housing portion 20 from the injection site module 103 may be inhibited in a case where the disposable housing 20 is in the second alignment position.

The receptacle 454 and connection member may include any suitable known rotary connection structure(s) for connecting two structures together upon engagement and relative rotation of the two structures in one direction, yet allow the two structures to be disengaged and separated from an engaged arrangement by relative rotation of the two structures in a second direction opposite the first direction. A motion inhibiting structure, such as a locking tab, pawl, or the like, may be provided to inhibit relative motion between the disposable housing portion 20 and the base 456, once those parts have been connected, as previously described.

Figure 17:
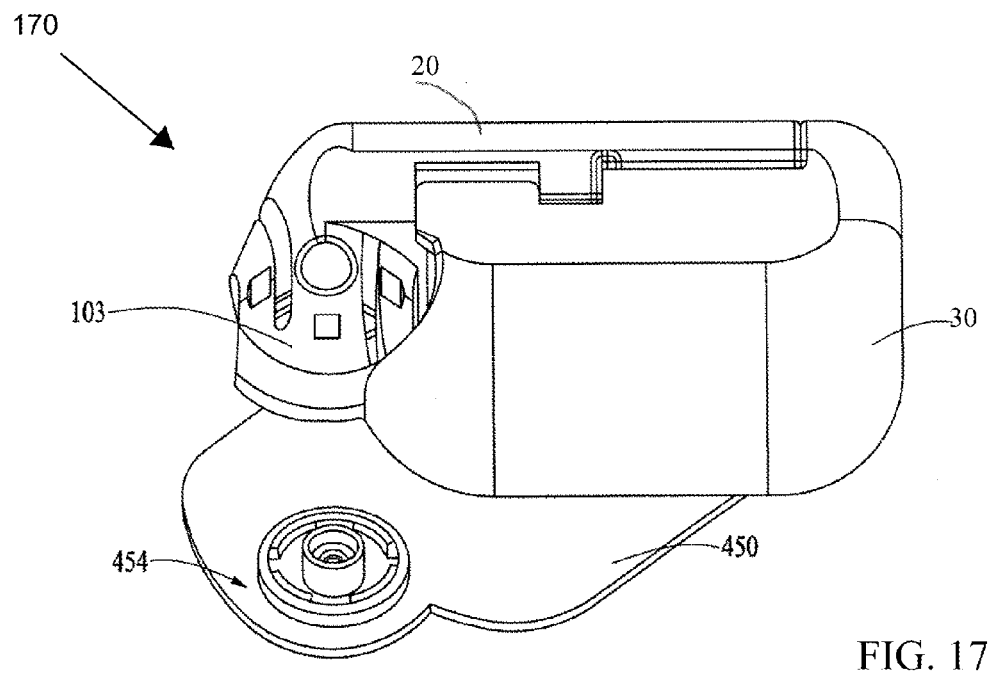
Figure 18:
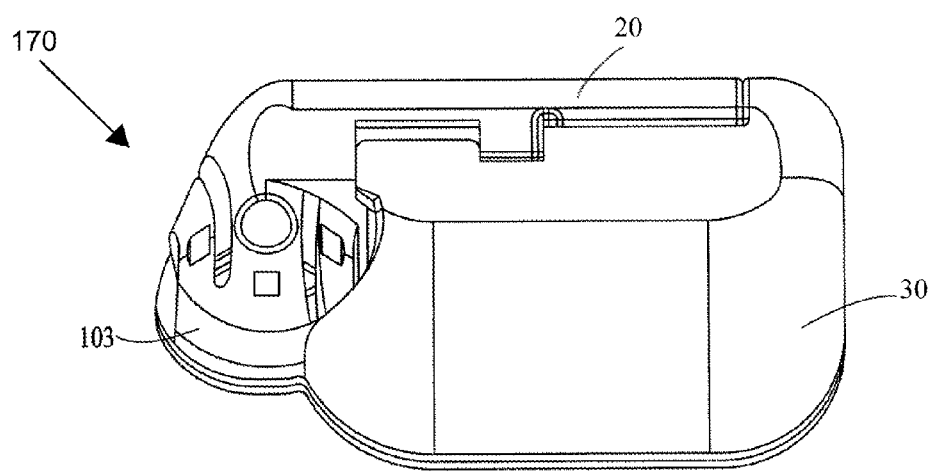
Figure 19:
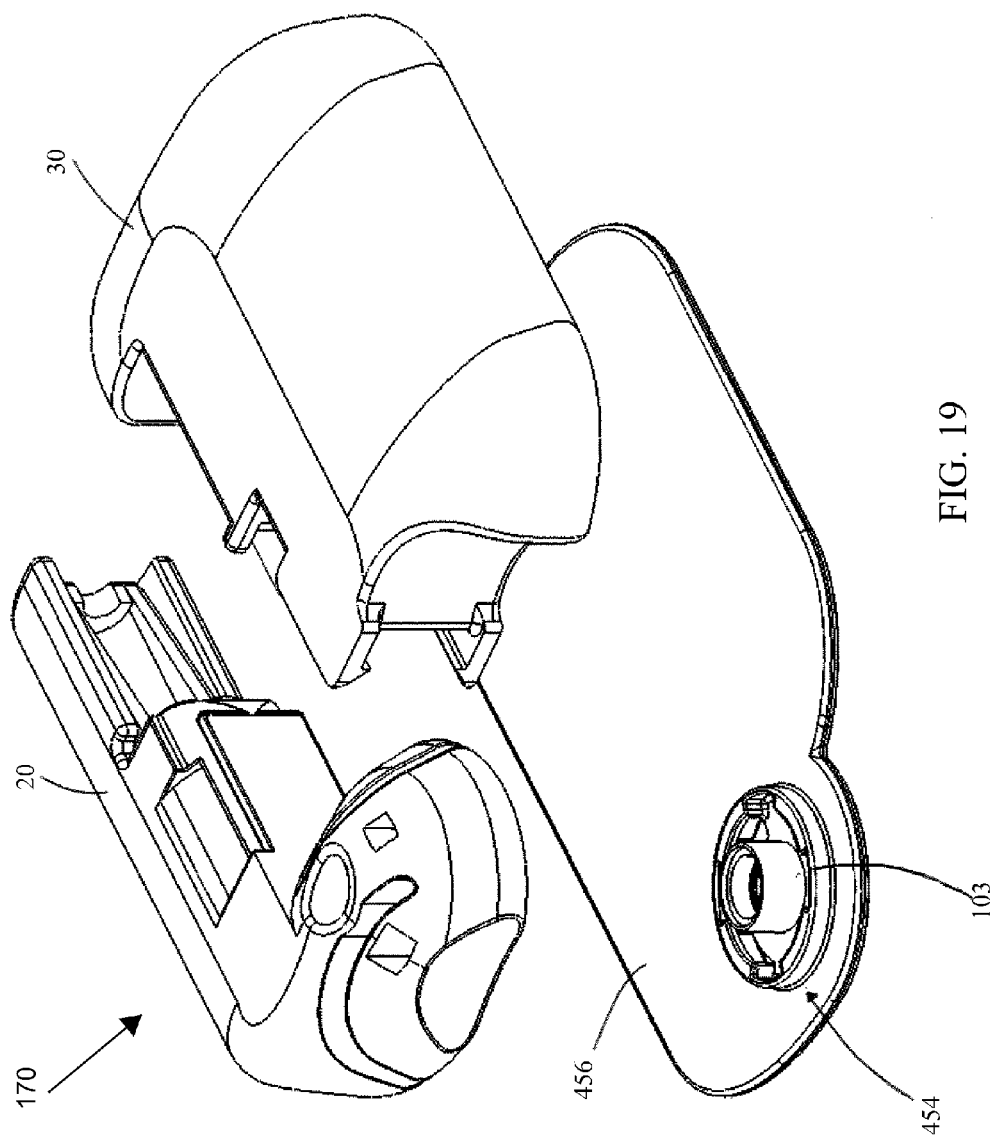

As shown in FIG. 19, the embodiments of FIGS. 17-19 may be formed in three general parts, including the disposable housing portion 20, the durable housing portion 30, and the injection site module 103 on the base 456. The durable housing portion 30 and the disposable housing portion 20 may be secured together (e.g., FIG. 17), and the combined, connected disposable and durable housing portions may be secured to the base 456. In one embodiment, the base 456 may be secured to skin of a patient-user before the combined, connected disposable and durable housing portions are secured to the base 456. In further embodiments, the combined, connected disposable and durable housing portions may be secured to the base 456 before the base 456 is secured to the skin of the patient-user.

With reference to FIGS. 7-19, various aspects of the multiple embodiments described above may be employed independently or in combinations thereof. Significant advantages can be obtained from various embodiments and combinations described herein, wherein an at-site delivery system may be made of two parts, including a disposable portion and a non-disposable portion. The disposable portion may contain all materials that are in direct contact with the infusion medium, such as reservoir body, reservoir piston, septum systems, and/or injection needle. The non-disposable portion could contain substantially the materials that are not in contact with the medication including the drive system, pressure or force sensing system (and/or other sensing systems), battery, electronics, display, and/or non-disposable housing.

The pump could be designed such that the disposable portion (with an unused new, user-filled, prefilled, refurbished, remanufactured or re-filled reservoir system 40 (e.g., FIGS. 1-6C)) is inserted into the non-disposable portion. By simplifying the manner in which the disposable portion of the delivery device can be replaced and by simplifying the manner in which the delivery device can be re-activated after replacing a disposable portion, a greater number of patient-users will be able to use and benefit from such delivery devices.

In addition, while embodiments described above include an injection site located on the disposable housing portion 20 or in an external injection site module 103, other embodiments may employ an injection site located in the durable housing portion 30. The injection site may be connected through suitable fluid-flow passages to the reservoir system 40 in the disposable housing portion 20 when the durable housing portion 30 and disposable housing portion 20 are engaged.

In addition, while embodiments are described above in the context of delivery devices for delivering an infusion medium from a reservoir to a patient-user, other embodiments may be operated to withdraw fluidic media from a patient-user (or other source) and transfer the fluidic media to the reservoir. Such other embodiments may be operated by operating the drive device to selectively move the piston plunger away from the septum-end of the reservoir (to increase the fluid-retaining volume of the reservoir) to create a negative pressure sufficient to draw fluid from the patient-user (or other source) to which the hollow needle or cannula is secured.

In addition, in any of the above-described embodiments, one or both of the disposable housing portion 20 and the durable housing portion 30 (and/or a separate base portion 21', 450, 456, or a separate injection site module 103) may include a sensor (not shown), such as a force sensor, or the like, or other suitable sensing device for sensing the proper placement or engagement of one or more of the components. In such embodiments, further electronics may control the operation of the drive device to inhibit operation of the drive device and/or the needle injector, unless the sensor senses the proper operable engagement of one or more of the components and/or the skin of the patient-user (or other suitable location).

Alternatively or in addition, one or both of the disposable housing portion 20 and the durable housing portion 30 may include a sensing device (not shown) for sensing the proper operable engagement of the disposable housing portion 20 and the durable housing portion 30 together (and/or with a separate base portion or a separate injection site module). In such an embodiment, further electronics may control the operation of the drive device to inhibit operation of the drive device and/or the needle injector, unless the sensing device senses the proper operable engagement of the disposable housing portion 20 and the durable housing portion 30 together (and/or with a separate base portion or a separate injection site module).

While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23 to allow the delivery device to be secured, removed and re-secured to the skin of the patient-user one or more times.

In such embodiments, a first cover film layer located at the end of the stack of alternating layers of adhesive material and cover film may be removed to expose a first layer of adhesive material. With the first layer of adhesive material exposed, a medical device system (e.g., 100, 110, 120, 130, 140, 150, 160, 170) (or component thereof) may be adhered to skin of a patient-user, as previously described. After a suitable period of usage, the medical device system (or component having the adhesive) may be removed from the skin of the patient-user, for example, for servicing, re-filling, replacement of one or more components, or the like. After removal of the medical device system (or component) from the skin of the patient-user, a second cover film layer on the medical device system (or component) may be removed to expose a second layer of adhesive material. With the second layer of adhesive material exposed, the medical device system (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while various embodiments described above may include one or more adhesive layers, each having a peelable cover layer, other embodiments may employ a single adhesive layer having (or plural adhesive layers, each having) a pattern of plural peelable cover layer portions. Accordingly, a patient-user may peel off one portion of the cover layer for adhering a medical device system (e.g., 100, 110, 120, 130, 140, 150, 160, 170) to the patient-user as described above, while leaving the rest of the pattern of peelable cover layer portions on the adhesive. In such an embodiment, after completion of a first period of operation of the medical device system and removal of the medical device system from the patient-user, a second portion of the peelable cover layer may be removed from the adhesive layer and the medical device system may be adhered to the same patient-user or, in certain contents, to a different patient-user for a second period of operation.

In various embodiments, while various medical device system (e.g., 100, 110, 120, 130, 140, 150, 160, 170) embodiments described above may include base portions (e.g., 21, 21', 450, 456) that are configured to be secured to skin of a patient-user (or other suitable surface of operation) and that extend along a length and/or width of the medical device system structure, other embodiments may employ base portions configured to be secured to the skin of the patient-user (or other surface) and extend less than a full length or width dimension of the medical device system structure to minimize surface area in contact with the patient-user (or other surface). Such embodiments may increase comfort of the patient-user during operation of the medical device system. Base portions having shapes and sizes different from those shown in the accompanying drawings may be employed for additional improvements with regard to the comfort of the patient-user and/or minimizing the surface area in contact with the patient-user. Furthermore, as noted above, the base portion may be composed of a flexible material that at least partially conforms to the curvature and movement of a body of the patient-user.

In any of the above-described embodiments in which an adhesive material is used to secure one or more medical device system (e.g., 100, 110, 120, 130, 140, 150, 160, 170) components to skin of a patient-user (or other suitable surface), multiple types of adhesive materials (or multiple strengths of adhesives) may be employed, such that a stronger adhesive may be provided in certain areas (e.g., around the needle injection site), while a weaker adhesive may be provided in other areas. Examples of various adhesive systems may be found in, but are not limited to, U.S. application Ser. No. 12/027,963, filed Feb. 7, 2008, entitled "Adhesive Patch Systems and Methods," herein incorporated by reference in its entirety.

Further examples of connection and/or alignment structures are described with reference to FIGS. 20A-30B, wherein a medical device system 500 may incorporate two parts: a first housing portion 530 and a second housing portion 550. Other embodiments may include medical device systems with more than two parts.

The medical device system 500 may be similar to or employed as an embodiment of the medical device systems discussed throughout the disclosure (e.g., FIGS. 1-6C). Although the medical device system 500 may include features similar or used with the embodiments of FIGS. 1-6C, it should be understood that the medical device system 500 may also include some or all of the same features and operate in a manner similar to that shown and described in the embodiments of FIGS. 7-19 and 31A-36. In addition, some or all of the features shown in FIGS. 1-19 and 31A-36 may be combined in various ways and included in the embodiments shown in FIGS. 20A-30B. Likewise, it should be understood that any of the features of the embodiments of FIGS. 20A-30B may be combined or otherwise incorporated into any of the other embodiments of FIGS. 20A-30B as well as any other embodiment herein discussed.

In various embodiments, the first housing portion 530 may be similar to the durable portion 30 (e.g., FIGS. 1-19) and may include (i.e., be integrated with) or be connected with the disposable portion 20 (e.g., FIGS. 1-19). As previously discussed with respect to FIGS. 1-6C, the durable housing portion 530 may include various components, such as, but not limited to, a drive device 80, drive motor 84, drive device linkage portion 82, and/or the like. The disposable housing portion 20, which may be integrated or connected with the first housing portion 530 may include various components, such as, but not limited to, a reservoir system 40.

Returning to FIGS. 20A-30B, in various embodiments, the second housing portion 530 may be similar to any of the bases (e.g., 21, 21', 450, 456 in FIGS. 1-19) that may be securable to skin of a patient-user during operation of the medical device system 500. The second housing portion 550 may include (i.e., be integrated with) or be connected with an injection site section 503, which may be similar to the injection module 103 (e.g., FIGS. 7-19) previously described. Other examples of injection site sections are described in, but are not limited to, U.S. patent application Ser. No. 12/553,008, filed Sep. 2, 2009, entitled "Insertion Device Systems and Methods," herein incorporated by reference in their entirety.

The first housing portion 530 may be for securing to the second housing portion 503 and/or the injection site section 503 of the second housing portion 550. In some embodiments, the second housing portion 550 may be secured to the skin of the patient-user before the first housing portion 530 is secured to the injection site section 503 and the second housing portion 550. In further embodiments, the first housing portion 530 may be secured to the second housing portion 550 and/or the injection site section 503 of the second housing portion 550 before the second housing portion 550 is secured to the skin of the patient-user.

The second housing portion 550 may include or be connected with a receptacle structure 510 for receiving fluidic media from a reservoir (e.g., reservoir system 40 in FIGS. 1-6C). Various examples of receptacle structures as well as connection structures for connecting two or more housing portions are described in, but are not limited to, U.S. patent application Ser. No. 12/553,008, filed Sep. 2, 2009, entitled "Insertion Device Systems and Methods," herein incorporated by reference in their entirety. In some embodiments, the receptacle structure 510 may be part of the second housing portion 550 adjacent a section of the second housing portion 550 containing the injection site section 503. In other embodiments, the receptacle structure 510 may include a housing connected or integrated with the second housing portion 550. In such embodiments, the receptacle structure 510 may be separate and apart from the injection site section 503 or adjacent the injection site section 503. In some embodiments, the injection site section 503 may be located on a different housing and connected, for example, with the receptacle structure via a tubing or other fluid conduit.

The second housing portion 550 may include a fluid conduit 524. The fluid conduit 524 may be (or in fluid communication with), but is not limited to, a needle, cannula, a piercing member, and/or the like. The fluid conduit 524 may provide a fluid passage from the receptacle structure 510 to the injection site section 503. The fluid conduit 524 may be supported by a supporting structure located within the receptacle structure 510. In some embodiments, the supporting structure may be a wall integral with the receptacle structure 510. In other embodiments, the supporting structure may be any suitable structure that is generally fixed relative to the receptacle structure 510 and is able to support the fluid conduit 524 in a generally fixed relation to the receptacle structure 510.

Figure 23:
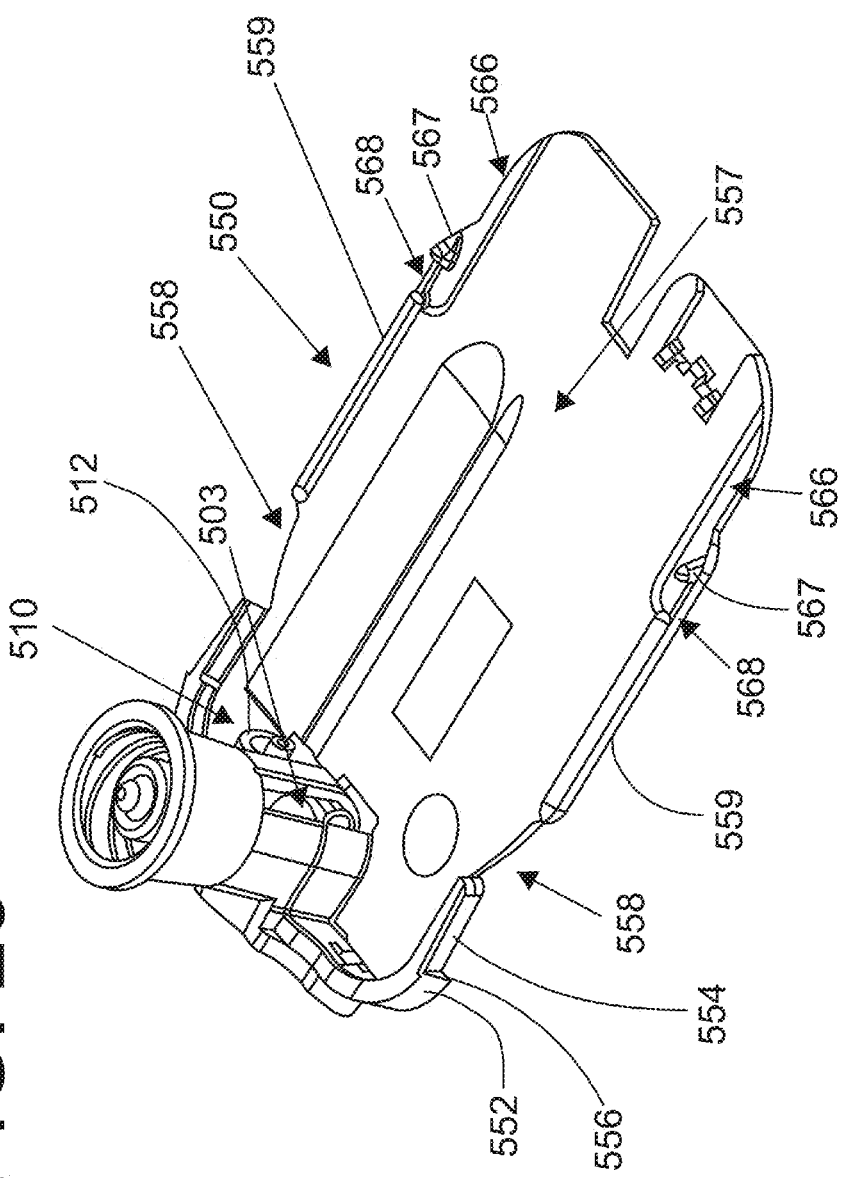
FIG. 23 illustrates a portion of a medical device system in accordance with an embodiment of the present invention.

The fluid conduit 524 may be arranged in any suitable manner to convey fluid, for example, from a reservoir to/from the patient-user. In FIGS. 23 and 24, the fluid conduit 524 is arranged to bend around a portion of the injection site section 503. As such, in various embodiments, the fluid conduit 524 may be provided on the second housing portion 550 in any suitable manner, including as a straight fluid conduit, a curved fluid conduit, or the like.

Returning to FIGS. 20A-24, the fluid conduit 524 may be made of any suitably rigid material, including, but not limited to metal, plastic, ceramic, composite materials, glass, or the like, and may have a hollow channel extending in a lengthwise dimension of the fluid conduit 524. The hollow channel in the fluid conduit 524 may be open at a location 524a along the lengthwise dimension of the fluid conduit 524, such as, but not limited to, a first end of the fluid conduit 524. The hollow channel in the fluid conduit 524 may be open at another location 524b along the lengthwise dimension of the fluid conduit 524, such as, but not limited to, a second end of the fluid conduit 524 opposite the first end of the fluid conduit 524. In some embodiments, the opening 524b of the fluid conduit 524 may be connected in fluid flow communication the injection site section 503.

In some embodiments, one or more of the openings in the fluid conduit 524 may be provided with a septum 526 that may be pierceable, for example, by a sharp end (e.g., 524b) of the fluid conduit 524. In such embodiments, the sharp end may be directed toward a surface of the septum 526 such that the septum 526 may be urged by the first housing portion 530 having a reservoir against the sharp end as the first housing portion 530 is connected to the second housing portion 550. The septum 526 may be made of any suitable material that may be pierceable by a needle (or the like), such as, but not limited to, a natural or synthetic rubber material, silicon, or the like. In some embodiments, the septum 526 may be made of a self-sealing material capable of sealing itself after a fluid conduit (and/or the like) has pierced the septum 526 and was subsequently withdrawn from the septum 526.

In some embodiments, a septum may be provided with the reservoir. The septum may be similar to the septum 526. The septum may be pierceable by a sharp end (e.g., 524b) of the fluid conduit 524. In such embodiments, the sharp end may be directed toward a surface to allow the sharp end to pierce the septum as the first housing portion 530 is connected to the second housing portion 550.

The injection site section 503 may include a channel 540 extending through the second housing portion 550. The channel 540 may have an open end 540a on a bottom surface of the second housing portion 550 (i.e., a surface for contacting skin of the user-patient). The channel 540 may have another open end 540b at an upper surface of the injection site section 503 (i.e., a surface opposite the surface for contacting the skin of the user-patient). The channel 540 may have an opening 540c for allowing the fluid conduit 524, for example via opening 524b, to be in fluid flow communication with the channel 540.

The channel 540 may include a channel section 542 having a suitable shape and size to receive an insert structure, a needle, and/or a cannula, such as those described in U.S. patent application Ser. No. 12/553,008, filed Sep. 2, 2009, entitled "Insertion Device Systems and Methods"; U.S. patent application Ser. No. 11/645,435, filed Dec. 26, 2006, titled "Infusion Medium Delivery system, Device And Method With Needle Inserter And Needle Inserter Device And Method"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety.

Other examples of various insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," U.S. Pat. Pub. No. US 2007/0142776, entitled "Insertion Device for an Insertion Set and Method of Using the Same," all of which are herein incorporated by reference in their entirety.

The first housing portion 530 may support a reservoir housing 508, which may be similar to or include reservoir system 40 (e.g., FIGS. 1-6C) or the like as previously described. The reservoir housing 508 of the first housing portion 530 may include a connection portion 531, which is some embodiments may be a port portion of the reservoir housing 508. The connection portion 531 of the reservoir housing 508 may have a suitable shape and size to fit at least partially within an opening 512 of the receptacle structure 510 in the second housing portion 550 when the second housing portion 550 and the first housing portion 530 are connected together.

Figure 21A:
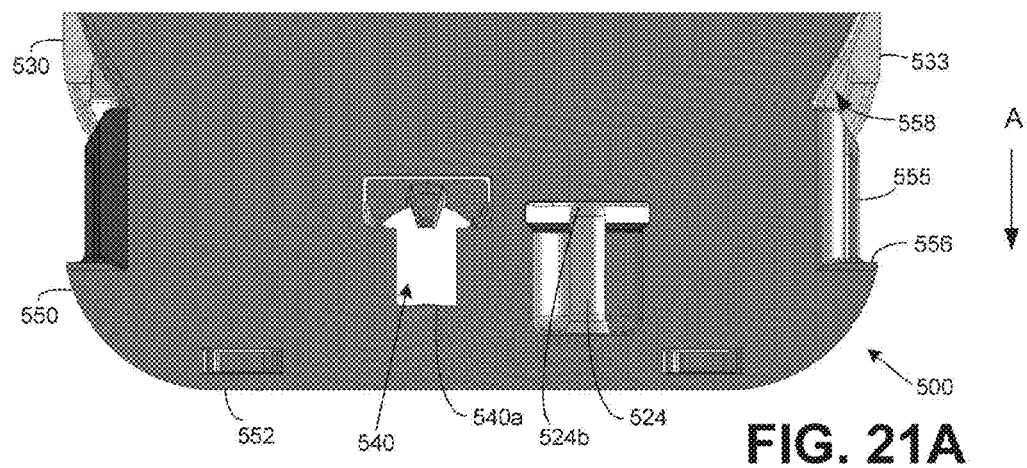
FIGS. 21A-21C illustrate a bottom down view of a portion of a medical device system in accordance with an embodiment of the present invention.
Figure 21B:
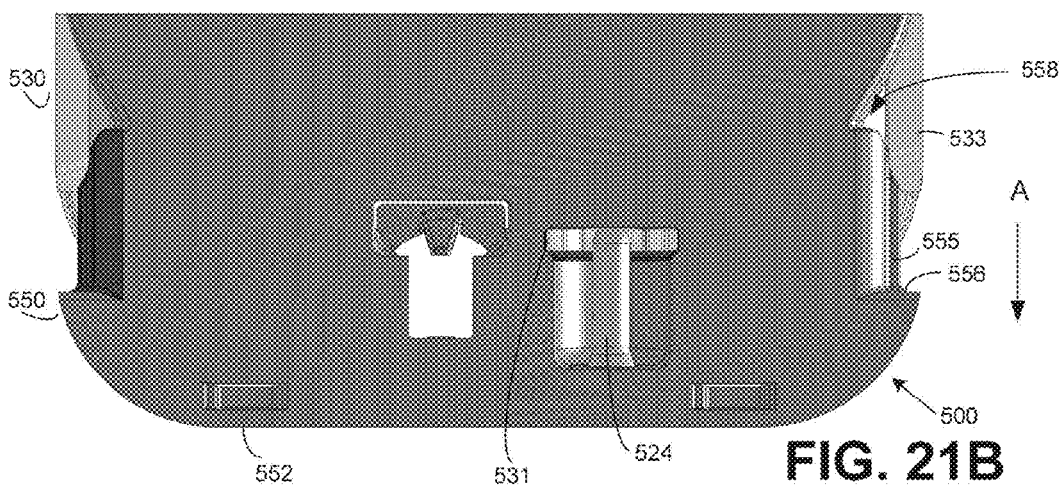
Figure 21C:
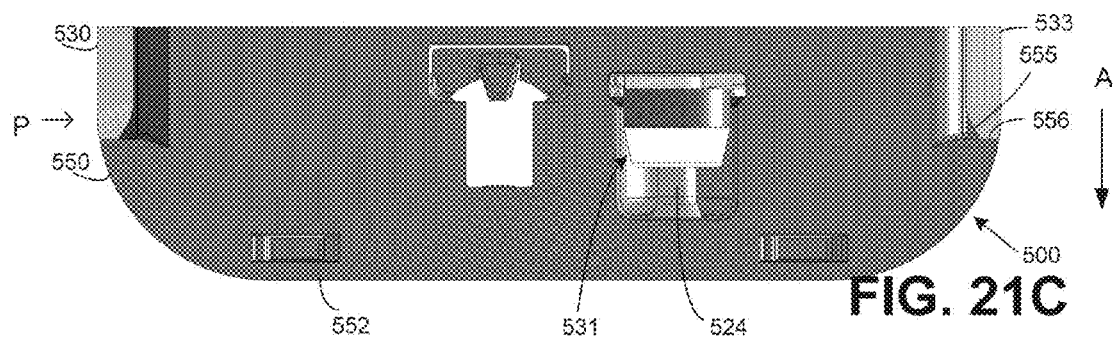

In the drawings of FIGS. 20A, 21A, and 22A, the second housing portion 550 and the first housing portion 530 are shown in a partially separated, disconnected relation, wherein the connection portion 531 of the reservoir housing 508 is outside of the opening 512 of the receptacle structure 510. By moving or sliding the first housing portion 530 in a first direction A relative to the second housing portion 550 to bring the first housing portion 530 and the second housing portion 550 together, the connection portion 531 of the reservoir housing 508 can be inserted into the opening 512 of the receptacle structure 510 of the second housing portion as shown in FIG. 21B. Continued relative movement of the second housing portion 550 and the first housing portion 530 together may cause the fluid conduit 524 to extend into the reservoir housing 508 as shown in FIG. 21C. in some embodiments, the continued relative movement of the second housing portion 550 and the first housing portion 530 together may cause a sharp end (e.g., 524b) of the fluid conduit 524 to pass through one or more septa in the receptacle structure 510 and/or the reservoir housing 508.

Returning to FIGS. 20-24, thus when the second housing portion 550 and the first housing portion 530 are brought together (e.g., FIGS. 20C, 21C, 22C) such that the first housing portion 530 is moved to a position P, at least a portion of the connection portion 531 may extend inside of the receptacle structure 510 with the fluid conduit 524 extending into the interior volume of the reservoir housing 508. Accordingly, the fluid conduit 524 may form a fluid flow path between the interior volume of the reservoir housing 508 and the injection site section 503 or other structure at the opening 524b of the fluid conduit 524. In addition or alternatively, the second housing portion 550 may be slidable in the first direction A relative to the first housing portion 530 to bring the two components together.

The receptacle structure 510 and the connection portion 531 may be provided with mating connectors that provide, for example, a snap or friction connection upon the second housing portion 550 and the first housing portion 530 being connected. In some embodiments, the mating connectors may include a protrusion (not shown) on one or the other of the receptacle structure 510 and the connection portion 531. The other of the receptacle structure 510 and the connection portion 531 may include a groove or indentation (not shown) arranged to engage each other in a snap-fitting manner upon the connection portion 531 being extended into the receptacle structure 510 a suitable distance.

In various embodiments, the second housing portion 550 and the first housing portion 530 may be configured to be attachable to and detachable from each other, and in specific embodiments to be slidable relative to each other to operatively engage and disengage each other. That is, the first housing portion 530 may be slidable in the first direction A relative to the second housing portion 550 to connect the two components (e.g., the first housing portion 530 is in the position P). Similarly, the first housing portion 530 may be slidable in a second direction, opposite the first direction A, relative to the second housing portion 550 to disconnect the two components.

In further embodiments, sliding the first housing portion 530 in the first direction A may allow the reservoir housing 508 of the first housing portion 530 to operatively engage the fluid conduit 524 of the second housing portion 550. Thus in some embodiments, a sliding motion, for example in the first direction A, for connecting the first housing portion 530 to the second housing portion 550 may be the same sliding motion for connecting the reservoir housing 508 of the first housing portion 530 to the fluid conduit 524 of the second housing portion 550. Accordingly, some embodiments may allow for the first housing portion 530 and the second housing 550 to be connected and the fluid conduit 524 and the reservoir housing 508 to be connected in a single movement. Such embodiments may facilitate engagement of the reservoir housing 508 by the fluid conduit 524.

With reference to FIGS. 20A-24, in some embodiments, the second housing portion 550 may include at least one arm 554, rail, or other raised surface that may be used to facilitate connecting (or removal of) the first housing portion 530 and the second housing portion 550 in a sliding motion. In further embodiments, the arm 554 may include a tab 555 fixedly attached or otherwise extending in a cantilevered manner from the arm 554. The arm 554 and the tab 555 may be used to align the second housing portion 550 and the first housing portion 530 while connecting the two components, as will be further described. Furthermore, the arm 554 and the tab 555 may be used to lock the first housing portion 530 to the second housing portion 550, for example, to inhibit separation of the first housing portion 530 from the second housing portion 550 in an axial direction transverse to the first direction A. Thus, the arm 554 and the tab 555 may prevent the first housing portion 530 from falling off or being pulled off the second housing portion 550.

The first housing portion 530 may include at least one groove, cutout, depression, spacing, aperture, and/or the like to facilitate connection between the second housing portion 550 and the second housing portion 550. For example, the first housing portion 530 may include an inner depression 534 for accepting a tab (e.g., tab 555) or other extended member disposed on the second housing portion 550.

In some embodiments, to connect the second housing portion 550 and the first housing portion 530 together, a tab 534 on the first housing portion 530 may be placed in a depression 558 in the second housing portion 550 as shown in FIGS. 20A, 21A, and 22A. The depression 558 may be sized liberally, for example larger than a size of the tab 534, so that the tab 534 may be easily positioned within the depression 558.

The tab 534 may be fixedly attached or otherwise extending from the arm 532 of the first housing portion 530.

Once the tab 534 and the arm 534 are in the depression 538, the first housing portion 530 may be slid relative to the second housing portion 550 in the first direction A. By doing so, the tab 555 on the arm 554 on the second housing portion 550 may slide into the inner depression 534 of the first housing portion 530. Continued relative movement of the second housing portion 550 and the first housing portion 530 may allow the tab 555 to slide along the inner depression 534 and the adjacent tab 534 of the first housing portion 530 as shown in FIGS. 20B, 21B, and 22B. As such, the reservoir supported by the first housing portion 530 may be slid or otherwise moved toward the fluid conduit 524 of the second housing portion 550 to allow the fluid conduit 524 to engage the interior volume of the reservoir housing 508 as shown in FIGS. 20C, 21C, and 22C.

Thus, in some embodiments, the second housing portion 550 and the first housing portion 530 may be operatively engaged and the reservoir housing 508 and the fluid conduit 524 may be operatively engaged in one motion. In other words, a motion (e.g., sliding motion in the first direction A) for engaging the first housing portion 530 to the second housing portion 550 may the same motion as a motion for engaging the fluid conduit 524 to the reservoir. In further embodiments, engagement of the tab 555 of the second housing portion 550 and the tab 533 of the first housing portion 530 may inhibit separation of the second housing portion 550 and the first housing portion 530 in an axial direction transverse to the first direction A.

In addition or alternatively, the second housing portion 550 may be provided with an arm having a tab and/or depression for receiving an arm and/or tab of the first housing portion 530 as previously described. Accordingly, when the first housing portion 530 and the second housing portion 550 are slid relative to each other, for example, in the first direction A, the first housing portion 530 and the second housing portion 550 may be operatively engaged in a manner as previously described.

In further embodiments, the second housing portion 550 may be provided with a stop surface 556 to prevent further movement of the first housing portion 530 relative to the second housing portion 550, for example, after the fluid conduit 524 has sufficiently engaged the interior volume of the reservoir housing 508 (e.g., the first housing portion is moved to position P). For instance, a portion of the first housing portion 530 may contact the stop surface 556 after the first housing portion 530 has been sufficiently advanced to substantially prevent the first housing portion 530 from further advancement. Such embodiments, may allow for additional protection of the reservoir housing 508 and/or the fluid conduit 524 from damage due to excessive force, speed, and/or the like in connecting the second housing portion 550 and the first housing portion 530. In other embodiments, a stop surface may be provided on the first housing portion 530 in addition or in alternative to the stop surface 556 of the second housing portion 550.

In some embodiments, the arm 532 and/or other portion of the first housing portion 530 may include a cutout, depression, or surface (not shown) that may aid a user-patient in gripping the first housing portion 530 during the connection process. In some embodiments, a portion of the second housing portion 550 may include a cutout, depression, or surface (not shown) that may aid a user-patient in gripping the second housing portion 550 during the connection process.

With reference to FIGS. 25A-26B, in some embodiments, a dovetail connection structure (not shown) may be provided for connecting the first housing portion 530 and the second housing portion 550. For example, one of the first housing portion 530 and the second housing portion 550 may have a groove 562 for receiving a protruding surface or dovetail 542 on the other of the first housing portion 530 and the second housing portion 550. A portion of the dovetail 542 may be placed in the groove 562 or slid into the groove 562. Further movement (e.g., in a sliding motion) of the dovetail 542 in the first direction along the groove 562 may connect the first housing portion 530 and the second housing portion 550 in a manner previously described. In some embodiments, the groove 562 and/or the dovetail 542 may be tapered to facilitate placement of the dovetail 542 in the groove 562.

In some embodiments, the groove 562 or the dovetail 542 may be tapered to secure the dovetail 542 in the groove 562, for example, in a friction fit as the dovetail 542 is advanced along the groove 562 in the first direction A. For example, as shown in FIGS. 25A and 25B, a width dimension of a groove 564 may be largest opposite the front end 552 of the second housing portion 550 and may taper to a narrow width dimension in a direction of the first direction A. Accordingly, such embodiments may allow for facilitating placement of the dovetail 542 in the groove 564, aligning of the first housing portion 530 as the dovetail 542 is guided by a surface defining the groove 564, and/or securing the dovetail 542 against the surface defining the groove 564 in a friction fit manner. In addition or alternatively, a groove 564 may be provided in the first housing portion 530 and a dovetail 542 may be provided on the second housing portion 550 in a manner previously described.

As another example shown in FIGS. 26A and 26B, a dovetail 544 may be tapered such that a front end of the dovetail 544 is narrower than a rear portion of the dovetail 544. Accordingly such embodiments, may allow for facilitating placement of the dovetail 544 in the groove 562, aligning of the first housing portion 530 as the dovetail 544 is guided by a surface defining the groove 562, and/or securing the dovetail 544 against the surface defining the groove 562 in a friction fit manner. In addition or alternatively, a groove 562 may be provided in the first housing portion 530 and a dovetail 544 may be provided on the second housing portion 550 in a manner previously described.

Returning to FIGS. 20A-24, in some embodiments, the arm 554 and/or the tab 555 may be angled relative to the second housing portion 550 to provide further alignment while connecting the first housing portion 530 to the second housing portion 550. For example, the arm 554 and/or the tab 55 may be angled outwardly (relative to the front end 552 of the second housing portion 550) to facilitate engagement with the arm 532, tab 534, and/or inner depression 533 of the first housing portion 530. As such, the arm 532 of the first housing portion 530 need only be placed in the depression 558 and advanced in the first direction A to allow the tab 534 and/or the inner depression 533 to meet the angled arm 554 and/or tab 555 at which point the angled arm 554 and/or tab 555 may guide the arm 532 of the first housing portion 530 with continued movement of the first housing portion 530. In such embodiments, the arm 532, the tab 534, and/or the entire first housing portion 530 may be made of a sufficiently flexible material, such as plastic, a composite material, and/or the like, to allow some flexing as the portion of the first housing portion 530 moves along the angled arm 554 and/or tab 555.

In some embodiments, such as the embodiments shown in FIGS. 23 and 24, one more rails 559, ridges, or other raised surfaces may be provided on the second housing portion 550 to guide the first housing portion 530 along the second housing portion 550. The rails 559 may be parallel or nonparallel to each other. The rails 559 may define an opening 557 through which the first housing portion 530 may be slid. In some embodiments, the rails 559 may be on a periphery (either a portion or an entirety thereof) of the second housing portion 550, and in some embodiments, the rails 559 may be arranged at any suitable location (e.g., internal or away from the periphery) along the second housing portion 550 (and/or first housing portion 530), such as those described, for example, in FIGS. 27A-27C.

In further embodiments, the rails 559 may be arranged to facilitate alignment and/or connection of the second housing portion 550 and the first housing portion 530. For example, opposing rails 559 may be arranged on the second housing portion 550 to be nonparallel to each other, as shown in, for example, FIGS. 27A-27C. The rails 559 may be angled inwardly (toward the front end 552 of the second housing portion 550) to provide a liberally sized opening 557 having a width dimension larger than a width dimension of the first housing portion 530 (or at least larger than a width dimension of a front portion of the first housing portion 530) so that the first housing portion 530 may be positioned easily within the opening 557. Accordingly, the first housing portion 530 may be advanced in the first direction A toward the front end 552 of the second housing portion 550. In a case where, the first housing portion 530 is being advanced toward the front end 552 and is slightly misaligned, a portion of the first housing portion 530 may contact (e.g., FIG. 27B) at least one of the rails 559 at which point the contacted rail 559 may guide the first housing portion 530 toward an aligned position with continued movement of the first housing portion 530 in the first direction A.

In other embodiments, the rails 559 may be parallel to each other with each of the rails 559 having a surface 559a that is nonparallel to a surface 559a of the other rail 559. As shown in FIGS. 28A-28C, the surface 559a of each of the rails 559 may face each other. Accordingly, the first housing portion 530 may be advanced in the first direction A toward the front end 552 of the second housing portion 550. In a case where, the first housing portion 530 is being advanced toward the front end 552 and is slightly misaligned, a portion of the first housing portion 530 may contact (e.g., FIG. 28B) at least one of surfaces 559a of the rails 559 at which point the contacted surface 559a may guide the first housing portion 530 toward an aligned position with continued movement of the first housing portion 530 in the first direction A.

Thus, various embodiments that include one or rails 559 may allow for some lateral misalignment at a beginning of the sliding motion (e.g., as the first housing portion 530 is moved in the first direction A). Such embodiments additionally may allow for forcing or guiding the first housing portion 530 into proper alignment with the second housing portion 550 as the sliding motion proceeds in the first direction A.

With reference to FIGS. 27A-27C and 28A-28C, in further embodiments, once the first housing portion 530 is placed in the aligned position by the rails 559, the first housing portion 530 and the second housing 550 may engage each other in a manner previously described with respect to FIGS. 20A-26B. For example, the arm 554 and tab 555 of the second housing portion 550 may engage the arm 532 of the first housing portion 530 as the first housing portion 530 is slid in the first direction A. As another example, a dovetail (e.g., 542) of the first housing portion 530 may engage a surface defining a groove (e.g., 562) of the second housing portion 550.

Returning to FIG. 23, in some embodiments, the second housing portion 550 may have a recess 566 for receiving a tab or protrusion (not shown) of the first housing portion 530. The tab may be flexible or supported on a portion of the first housing portion 530 that is flexible. In FIG. 23, the recess 566 is provided on a rear portion of the second housing portion 550, but in other embodiments, the recess 566 may be provided at any suitable location. During the sliding connection of the first housing portion 530 and the second housing portion 550 as previously described, the tab may be received by the recess 566 and guided by a surface defining the recess 566.

A protrusion 567 may be arranged on the second housing portion 550 to direct or flex the tab inwardly (or outwardly) as the first housing portion 530 moves (e.g., slides) in the first direction A. That is, the protrusion 567 may be arranged to direct or flex the tab in a direction transverse to the first direction A. Continued movement of the first housing portion 530 in the first direction A beyond the protrusion 567 may allow the tab to flex outwardly (or inwardly) into a cavity 568 or an abutment defining the cavity 568 of the second housing portion 550.

The dimensions of the first housing portion and the second housing portion 550 and arrangement of the recess 566, cavity 568, and tab may be selected such that the tab enters the cavity 568 upon the first housing portion 530 being moved to the position P. As discussed, moving the first housing portion 530 to the position P may allow, for example, the fluid conduit 524 to engage with (i.e., be in fluid communication with) the interior volume of the reservoir housing 508.

The tab may remain in the cavity 568 until the patient-user pushes the tab inwardly (or outwardly) to move the tab to allow the tab to move beyond the protrusion 567. Accordingly, the first housing portion 530 may be moved in a second direction opposite the first direction A, for example, to disengage the first housing portion 530 and the second housing portion 550. In additional or alternatively, the first housing portion 530 may have a recess for receiving a tab of the second housing portion 550 in a slidable manner with a protrusion and a cavity for retaining the tab in a manner previously described. In some embodiments, the tab and the recess 566 may be the dovetail (e.g., 542) and the groove (e.g., 562) as described, for example, with respect to FIGS. 25A-26B.

With reference to FIGS. 20A-28C, in further embodiments, at least one magnet (not shown) may be provided on one or both of the second housing portion 550 and the first housing portion 530 along with an magnetically attractive material (not shown), such as, but not limited to, metal, a magnet having an opposing pole, or the like, on the other of the second housing portion 550 and the first housing portion 530. Each of the magnet(s) and the magnetically attractive material may be arranged at a location to interact with each other upon the second housing portion 550 and the first housing portion 530 being connected properly or otherwise brought into a pre-defined, sufficiently aligned position and/or in a pre-defined, sufficiently close proximity. The pre-defined aligned position and/or proximity, for example, may correspond to a properly aligned and mutually proximate position for connection of the first housing portion 530 and the second housing portion 550 for operation.

The magnets and the magnetically attractive material may be provided at one or more locations to interact with each other upon the first housing portion 530 being moved to the position P relative to the second housing portion 550. For instance, in a case where the first housing portion 530 is moved to the position P, the magnet on one of the housing portions may interact with the magnet (or attractive material) on the other of the housing portions, for example, to connect and/or align the housing portions. Examples of magnetic connection and alignments structures and other alignment and connection structures will be described later and are also described in, but are not limited to, U.S. patent application Ser. No. 11/759,725, filed Jun. 7, 2007, entitled "Infusion Medium Delivery Device and Method with Drive Device for Driving Plunger in Reservoir," herein incorporated by reference in its entirety.

Figure 29A:
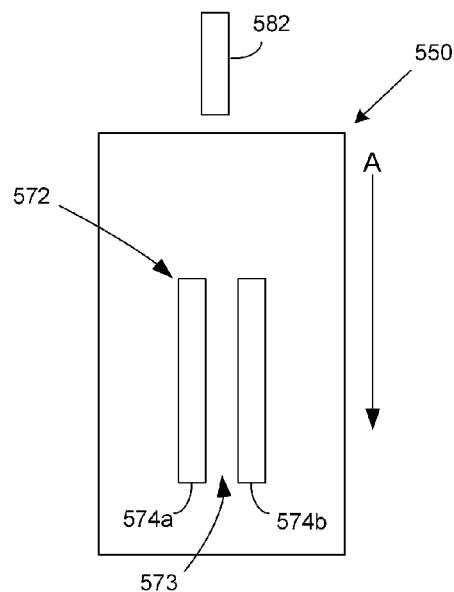
FIGS. 29A and 29B illustrate a portion of a medical device system in accordance with an embodiment of the present invention.
Figure 29B:
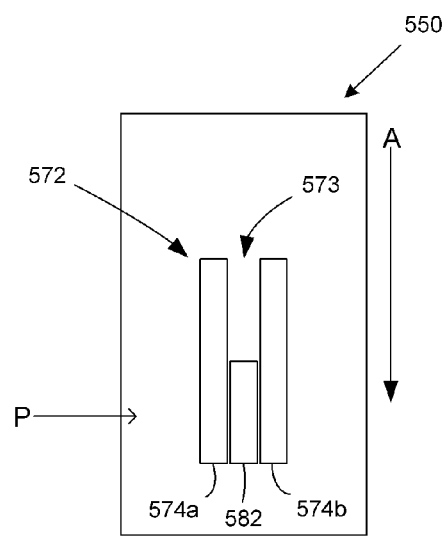

In some embodiments, such as the embodiments shown in FIGS. 29A and 29B, the first housing portion 530 and the second housing portion 550 may include magnets configured to align, for example laterally, the first housing portion 530 and the second housing portion 550 in a case where the first housing portion 530 and the second housing portion are being connected and are misaligned. For instance, the magnets may be arranged to oppose each other in a case where the first housing portion 530 and the second housing portion 550 are misaligned. For example, the magnets may each have surfaces having similar pole directions. For instance, a magnet 582 supported by the first housing portion (not shown in FIGS. 29A and 29B) may have be opposed to one or more magnets 572 supported on the second housing portion 550. For example, the magnet 582 may have a surface have a first polarity (e.g., North), and the one or more magnets 572 may each have a surface having a polarity (e.g., North) similar to the first polarity of the magnet 582.

In some embodiments, the one or more magnets 572 may comprise a first magnet 574a and a second magnet 574b. A spacing 573 may be provided between the first magnet 574a and the second magnet 574b. In such embodiments, the first housing portion and the second housing portion 550 may be connected, for example, in a slidable manner as previously described. The magnet 582 may be guided along the one or more magnets 572 as the first housing portion is moved in the first direction A. For example, the magnet 582 may move between the first magnet 574a and the second magnet 574b over the spacing 573. In such embodiments, lateral misalignment of the first housing portion and the magnet 582 may be inhibited by the opposing one or more magnets 572.

Figure 30A:
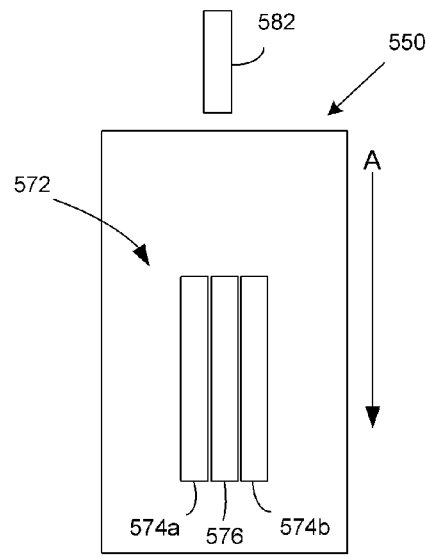
FIGS. 30A and 30B illustrate a portion of a medical device system in accordance with an embodiment of the present invention.
Figure 30B:
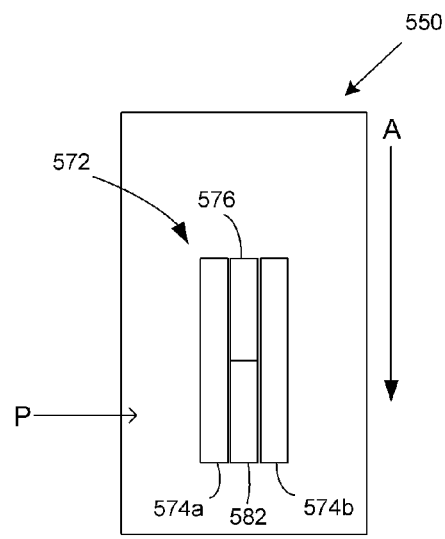

In further embodiments, such as that shown in FIGS. 30A and 30B, the one or more magnets 572 supported on the second housing portion 550 may include a third magnet 576 that is attracted to the magnet 582 supported by the first housing portion (not shown in FIGS. 30A and 30B). For example, the third magnet may have a second polarity (e.g., South) opposite the first polarity of the magnet 583. In some embodiments, the one or magnets 572 may include a magnetically attractive material (as opposed to a magnet), such as a metal, ferrous conduit, or the like.

In various embodiments, the first housing portion 530 and the second housing portion 550 may be connected, for example, in a slidable manner as previously described. The magnet 582 (and/or the magnetically attractive material) may be guided along the one or more magnets 572 as the first housing portion is moved in the first direction A. For example, the magnet 582 may move between the first magnet 574a and the second magnet 574b over the third magnet 576. In such embodiments, lateral misalignment of the first housing portion and the magnet 582 may be inhibited by the opposing one or more magnets 572 and/or by the attraction between the magnet 582 and the third magnet 576 (and/or the magnetically attractive material).

With reference to FIGS. 29A-30B, in some embodiments, the magnets (e.g., 582, 572) may be arranged in a manner described with respect to, for example (but not limited to), the rails 559 and dovetail structures described in FIGS. 25A-28C. For instance, returning to FIGS. 29A-30B, the first magnet 574a and the second magnet 574b may be arranged to be non-parallel to each other, as described in 27A-28C. As another example, the first magnet 574a and the second magnet 57b may be arranged to taper such that the spacing 573 narrows in the first direction A, for example, as described in FIGS. 25A-26B.

With reference to FIGS. 20A-30B, in some embodiments, at least one latch (not shown), or the like may be provided on one of the second housing portion 550 and the first housing portion 530. The latch may be configured to engage an aperture (not shown), an engagement member, and/or the like in the other of the second housing portion 550 and the first housing portion 550 upon the second housing portion 550 and the first housing portion 530 being operatively engaged (e.g., the first housing portion 530 moved to the position P).

In further embodiments, the latch may be configured to manually engage and/or disengage the aperture (or the like). For instance, the latch may be configured to be squeezable (e.g., pressed inward relative to the housing portions) to allow the first housing portion 530 to engage and/or disengage from the second housing portion 550. For example, a latch may be provided on each side of the first housing portion 530 such that a squeezing motion (e.g., inward) of the latches may allow each of the latches to be released from a corresponding aperture (or the like) to allow the first housing portion 530 to be removed from the second housing portion 550.

In yet further embodiments, the latch may be configured to force the first housing portion 530 and the second housing portion 550 apart in a case where the first housing portion 530 and the second housing portion 550 are not properly connected. For example, in a case where the first housing portion 530 is not slid sufficiently relative to the second housing portion 550 to reach the position P, the latch may force the first housing portion 530 in an opposite direction to allow the user-patient to repeat the connection process. In such embodiments, a bias member (not shown), such as a spring, resilient material, and/or the like, may be provided with the latch. The bias member may bias the first housing portion 530 in a direction opposite the first direction A. As such, in a case where the first housing portion 530 is moved sufficiently in the first direction A relative to the second housing portion 550 (e.g., position P), the latch may engage the aperture (or the like). Whereas in a case where the first housing portion 530 is not moved sufficiently in the first direction A relative to the second housing portion 550, the bias member may urge the first housing portion 530 in an opposite direction to the first direction A to allow the user-patient to repeat the connection process.

In some embodiments, a sensor (not shown) may be provided for sensing the latch and/or a relative position of the latch, for example a detectable feature of the latch or provided on the latch. As such, the sensor can determine whether the latch has properly engaged the aperture (or the like) to determine that the second housing portion 550 and the first housing portion 530 have been properly connected (e.g., the first housing portion 530 is in the position P). Examples of sensors, detectable features, and the like are described in, but are not limited to, U.S. patent application Ser. No. 12/649,619, filed Dec. 30, 2009, entitled "Alignment Systems and Methods," herein incorporated by reference in its entirety.

Suitable electronics may be connected to the sensor to provide a controlled power signal to selectively activate or otherwise control one or more of the sensor and/or other components as described throughout the disclosure. For example, the sensor may be controlled to activate upon a manual activation of a control button, switch, or other manual operator on one of the connectable components or on a remote-controller device (not shown) connected in wireless communication with the sensor through suitable control electronics. As another example, the sensor may be controlled to activate automatically after a certain action, such as activation of a button, and/or the like or after a certain amount of time. In some embodiments, the sensor may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in its entirety. Thus, in such examples, the sensor may be activated, for example, before or after, the first housing portion 530 and the second housing portion 550 are brought operatively engaged.

Further examples of connection and/or alignment structures are described with reference to FIGS. 31A-33B, wherein a medical device system 900 may incorporate two parts: a first housing portion 901 and a second housing portion 902. Other embodiments may include medical device systems with more than two parts.

The medical device system 900 may be similar to or employed as an embodiment of the medical device system 500 (e.g., FIGS. 20A-30B) and/or the other medical device systems discussed throughout the disclosure (e.g., FIGS. 1-19). Although the medical device system 900 may include features similar or used with the embodiments of FIGS. 20A-30B, it should be understood that the medical device system 900 may also include some or all of the same features and operate in a manner similar to that shown and described in the embodiments of FIGS. 1-19 and 34A-36. In addition, some or all of the features shown in FIGS. 1-30B and 34A-36 may be combined in various ways and included in the embodiments shown in FIGS. 31A-33B. Likewise, it should be understood that any of the features of the embodiments of FIGS. 31A-33B may be combined or otherwise incorporated into any of the other embodiments of FIGS. 31A-33B as well as any other embodiment herein discussed.

In various embodiments, the first housing portion 901 may be, but is not limited to, any of the housing portions described, such as the durable portion 30 (e.g., FIGS. 1-19) and the disposable portion 20 (e.g., FIGS. 1-19). In specific embodiments, the first housing portion 901 may be similar to the first housing portion 530 (e.g., FIGS. 20A-30B).

Moreover in various embodiments, the second housing portion 902 may be, but is not limited to, any of the housing portions described, such as the base 21 (or 21', 450, 456 in FIGS. 1-19), the durable housing portion 30, and the disposable housing portion. In specific embodiments, the second housing portion 902 may be similar to the second housing portion 550 (e.g., FIGS. 20A-30B). In such embodiments, for example, the second housing portion 902 may be secured to skin of a patient-user or otherwise carried by the patient-user (e.g., secured on a belt, clothing, or the like) during operation of the medical device system 900.

The first housing portion 901 may include a plurality of electrical contacts 910 including a first main electrical contact 912 and a second main electrical contact 916. The plurality of electrical contacts 910 may also include one or more other electrical contact 914. The electrical contacts 910 may me made of any suitable material such as metal, a rubber conductive pad, as well as any other electrical conductor.

In some embodiments, the other electrical contact 914 may be arranged between the first main electrical contact 912 and the second main electrical contact 916. However, the other electrical contact 914 may be arranged at any suitable location. The other electrical contact 914 may be made of the same material as the first main electrical contact 912 and/or the second main electrical contact 914. In other embodiments, the other electrical contact 914 may be made of a different material (e.g., a different conductive material, or a non-conductive material) from the first main electrical contact 912 and/or the second main electrical contact 914.

The second housing portion 902 may include a shorting mechanism 920 or the like configured to establish a short or electrical connection with at least some of the electrical contacts 910 upon connecting the first housing portion 901 and the second housing portion 902. In some embodiments, the shorting mechanism 920 may establish an electrical connection with at least some of the electrical contacts 910 in a case where the first housing portion 901 and the second housing portion 902 are connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 901 and the second housing portion 902 for operation. In other embodiments, the shorting mechanism 920 may be a known resistance or the like.

The shorting mechanism 920 may have a first end 922 and a second end 924 for contacting respective electrical contacts 910 on the first housing portion 901. In some embodiments, the first end 922 and the second end 924 may be arranged to contact the first main electrical contact 912 and the second main electrical contact 916 respectively when the first housing portion 901 and the second housing portion 902 are connected properly, for example, as shown in FIG. 31B. As such, the shorting mechanism 920 may contact the first main electrical contact 912 and the second main electrical contact 916, but not the other electrical contact 914. Suitable circuitry (not shown) connected to the electrical contacts 910 may be configured to detect an electrical connection or short between the first main electrical contact 912 and the second main electrical contact 916 (via the shorting mechanism 920) indicating a proper connection of the first housing portion 901 and the second housing portion 902.

Furthermore, the electrical contacts 910 and/or the shorting mechanism 920 may be arranged on their respective parts such that in a case where the first housing portion 901 and the second housing portion 902 are not properly connected, such as in FIG. 31C, an electrical connection between the first main electrical contact 912 and the second main electrical contact 916 is not be established. Accordingly, this may indicate that the first housing portion 901 and the second housing portion 902 have not been connected properly.

Returning to FIGS. 31A-31C, some embodiments in which at least one other electrical contact 914 is arranged between the first main electrical contact 912 and the second main electrical contact 916 may prevent a false detection of a proper connection of the first housing portion 901 and the second housing portion 902. For example, the circuitry may be able to distinguish between a case where a stray metal object (e.g., a metal key, paper clip, coin) or other electrical conductor contacts the first main electrical contact 912, the second main electrical contact 916, and the other contact 914 as opposed to a proper connection where only the first main electrical contact 912 and the second main electrical contact 912 are contacted (by the shorting mechanism).

In some embodiments, an electrical connection will only be established when the first end 922 contacts the first main electrical contact 912 and the second end 924 contacts the second main electrical contact 916. In other embodiments, an electrical connection may be established in a case where the first end 922 and the second end 924 contact the first main electrical contact 912 and the second main electrical contact 916 respectively or in a case where the first end 922 and the second end 924 contact the second main electrical contact 916 and the first main electrical contact 912 respectively. Such embodiments, may allow for a detection of a proper connection of the first housing portion 901 and the second housing portion 902 in more than one orientation.

In the embodiments shown in FIGS. 31A-31C, there are three electrical contacts: the first main electrical contact 912, the second main electrical contact 916, and the other electrical contact 914 arranged between the first main electrical contact 912 and the second main electrical contact 916. However, in various other embodiments, any suitable number of electrical contacts 910 may be provided on the first housing portion 901 as required. In some embodiments, the main electrical contacts (e.g., 912, 916) are arranged as the outermost electrical contacts; however, in other embodiments, the main electrical contacts may be arranged anywhere relative to the other electrical contact(s) 914.

Similarly, the other electrical contacts need not be limited to being arranged in between main electrical contacts, but may also be arranged to be the outermost electrical contact in some embodiments. As such, the electrical contacts 910 (e.g., main electrical contacts and other electrical contacts) may be arranged or otherwise provided on the first housing portion 901 in any suitable manner, for example linearly/non-linearly, equidistant/non-equidistant, similar/varying heights, arranged on similar/varying surfaces, same/different resistances, same/different materials, and/or the like. For instance, as shown in FIG. 32, seven electrical contacts 910 could be provided including two first main electrical contacts 912, a first other electrical contact 914, a second main electrical contact 916, a second other electrical contact 914, and two third main electrical contacts 918.

In the embodiments shown in FIGS. 31A-31C, the shorting mechanism 920 has two ends 922, 924 for contacting the first main electrical contact 912 and the second main electrical contact 916, respectively. However, in various other embodiments, the shorting mechanism 920 may be provided with any suitable number of ends or contact surfaces for contacting the electrical contacts 910 as required. Similarly, the ends (e.g., 922, 924) may be arranged on shorting mechanism 920 in any suitable manner.

In various embodiments, the electrical contacts 910 may be provided on the first housing portion 901 and the shorting mechanism 920 may be provided on the second housing portion 902. In other embodiments, the electrical contacts 910 may be provided on the second housing portion 902 and the shorting mechanism 920 may be provided on the first housing portion 901. In further embodiments, each of the first housing portion 901 and the second housing portion 902 may be provided with a shorting mechanism 920 and complementing electrical contacts 910.

In some embodiments, such as the embodiments shown in FIGS. 33A and 33B, a bias member 919, such as a spring, or the like, may be provided to bias the electrical contacts 910 either individually, partially (e.g., some, but not all), or collectively toward a first position (e.g., an extended position as shown in FIG. 33A). As such, the electrical contacts 910 may be moveable toward a second position (e.g., a retracted position as shown in FIG. 33B), for example, as the first housing portion 901 and the second housing portion 902 are brought together. Thus, while in the second position, an electrical connection may be established between the first main electrical contact 912 and the second main electrical contact 916 via the shorting mechanism 910 in a similar manner to that previously described. The bias member 919 may be located at least partially within a recess of the first housing portion 901. In some embodiments, the bias member 919 may be supported on the first housing portion 901, for example, between the electrical contacts 910 and the first housing portion 901.

In addition or in alternative to the above, in some embodiments, a bias member, such as a spring, or the like, may be provided to bias the shorting mechanism or portion thereof (e.g., ends 922, 924) toward a first position (e.g., an extended position). As such, shorting mechanism or portion thereof may be moveable toward a second position (e.g., a retracted position), for example, as the first housing portion 901 and the second housing portion 902 are brought together. Thus, while in the second position, an electrical connection may be established between the first main electrical contact 912 and the second main electrical contact 916 via the shorting mechanism 910 in a similar manner to that previously described.

In various embodiments, the electrical contacts 920 and/or the shorting mechanism 910 may be or otherwise comprise a bias member like that previously described. For example, the electrical contacts 920 may be metal springs or the like that may be moveable from the first position to the second position as the first housing portion 901 and the second housing portion 902 are brought together.

Further examples of connection and/or alignment structures are described with reference to FIGS. 34A-36, wherein a medical device system 1100 may incorporate two parts: a first housing portion 1101 and a second housing portion 1102. Other embodiments may include medical device systems with more than two parts.

The medical device system 1100 may be similar to or employed as an embodiment of the medical device system 500 (e.g., FIGS. 20A-30B) and/or the other medical device systems discussed in the disclosure (e.g., FIGS. 1-19). Although the medical device system 1100 may include features similar or used with the embodiments of FIGS. 20A-30B, it should be understood that the medical device system 1100 may also include some or all of the same features and operate in a manner similar to that shown and described in the embodiments of FIGS. 1-19 and 31A-33B. In addition, some or all of the features shown in FIGS. 1-33B may be combined in various ways and included in the embodiments shown in FIGS. 34A-36. Likewise, it should be understood that any of the features of the embodiments of FIGS. 34A-36 may be combined or otherwise incorporated into any of the other embodiments of FIGS. 34A-36 as well as any other embodiment herein discussed.

In various embodiments, the first housing portion 1101 may be, but is not limited, to any of the housing portions described, such as the durable portion 30 (e.g., FIGS. 1-19) and the disposable portion 20 (e.g., FIGS. 1-19). In specific embodiments, the first housing portion 1101 may be similar to the first housing portion 530 (e.g., FIGS. 20A-30B).

Moreover in various embodiments, the second housing portion 1102 may be, but is not limited, to any of the housing portions described, such as the base 21 (or 21', 450, 456 in FIGS. 1-19), the durable housing portion 30, and the disposable housing portion. In specific embodiments, the second housing portion 1102 may be similar to the second housing portion 550 (e.g., FIGS. 20A-30B). In such embodiments, the second housing portion 1102 may be secured to skin of a patient-user during operation of the medical device system 1100.

The first housing portion 1101 may include a sensor 1110 for sensing a magnetic field, and in specific embodiments, for sensing at least a direction (i.e., vector) of a magnetic field. Such sensors 1110 may allow for detecting a presence of a magnetic field or magnetic source independent of magnetic strength. Furthermore, sensing a direction of a magnetic field may increase the probability that the sensor 1110 is sensing the appropriate the magnetic source. The sensor 1110 may be similar to the sensors described in, but is not limited to, U.S. patent application Ser. No. 12/649,619, filed Dec. 30, 2009, entitled "Alignment Systems and Methods," herein incorporated by reference in its entirety. The sensor 1110 may be disposed in the first housing portion 1101 or be provided on the first housing portion 1101.

Suitable electronics may be connected to the sensor 1110 to provide a controlled power signal to selectively activate or otherwise control one or more of the sensor 1110 and/or other components as described throughout the disclosure. For example, the sensor 1110 may be controlled to activate upon a manual activation of a control button, switch, or other manual operator on one of the connectable components or on a remote-controller device (not shown) connected in wireless communication with the sensor 1110 through suitable control electronics. As another example, the sensor 1110 may be controlled to activate automatically after a certain action, such as activation of a button, and/or the like or after a certain amount of time. In some embodiments, the sensor 1110 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 1110 may be activated, for example, before or after, the first housing portion 1101 and the second housing portion 1102 are brought operatively engaged.

The second housing portion 1102 may include a magnetic source 1120 or the like for providing a magnetic field having a direction. The magnetic source 1120 may be arranged on or in the second housing portion 1102 at a location to allow the magnetic field and/or the direction of the magnetic field of the magnetic source 1120 to be detectable by the sensor 1110 in a case where the first housing portion and the second housing portion 1102 are connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 1101 and the second housing portion 1102 for operation. Detection of the magnetic field and/or the direction of the magnetic field of the magnetic source 1120 may indicate that the first housing portion 1101 and the second housing portion 1102 have been connected properly.

In some embodiments, the magnetic source 1120 may be in contact with the sensor 1110 to allow the sensor 1120 to detect the magnetic field and/or direction of the magnetic field of the magnetic source 1120. In other embodiments, the magnetic source 1120 need not be in contact with the sensor 1110 to allow the sensor 1110 to detect the magnetic field and/or direction of the magnetic field of the magnetic source 1120. For example, a portion of one or both of the first housing portion 1101 and the second housing portion 1102 may be arranged between the sensor 1110 and the magnetic source 1120.

Furthermore, the sensor 1110 and the magnetic source 1120 may be arranged such that in a case where the first housing portion 1101 and the second housing portion 1102 are not been properly connected, the sensor 1110 will not be able to detect the magnetic field and/or the direction of the magnetic field, for example, because the sensor 1110 and the magnetic source 1120 are too far apart. Accordingly, this may indicate that the first housing portion 1101 and the second housing portion 1102 have not been connected properly.

In some embodiments, the magnetic source 1120 may provide more than one magnetic fields and/or directions of magnetic fields. As shown for example in FIGS. 34A and 34B, a first field 1122, a second field 1124, and a third field 1126 are provided in which the first field 1122 and the third field 1126 have a direction different from a direction of the second field 1124. In such an example, the sensor 1110 may be configured to detect only the second field 1124 and/or the direction (e.g., North) of the second field 1124 in a manner previously described. Thus, detection of the second field 1124 and/or the direction of the second field 1124 may indicate that the first housing portion 1101 and the second housing portion 1102 have been connected properly.

In further embodiments, the sensor 1110 may be configured to detect other fields (e.g., first field 1122 and second field 1126) and/or directions of the other fields such that detection of the other fields and/or directions of the other fields may indicate an improper connection of the first housing portion 1101 and the second housing portion 1102. The electronics may employ an algorithm for processing information relating to the various fields and/or other related information (e.g., magnetic field strength, gauss level, and/or the like).

In some embodiments, such as the embodiments shown in FIGS. 35A-36, the first housing portion 1101 may have a sensor 1111 for sensing a gauss level or the like of a magnetic source. The sensor 1111 may be similar to the sensor 1110 previously described or any of the sensors described in, but is not limited to, U.S. patent application Ser. No. 12/649,619, filed Dec. 30, 2009, entitled "Alignment Systems and Methods," herein incorporated by reference in its entirety. The sensor 1111 may be disposed in the first housing portion 1101 or be provided on the first housing portion 1101.

Suitable electronics may be connected to the sensor 1111 to provide a controlled power signal to selectively activate or otherwise control one or more of the sensor 1111 and/or other components as described throughout the disclosure. For example, the sensor 1111 may be controlled to activate upon a manual activation of a control button, switch, or other manual operator on one of the connectable components or on a remote-controller device (not shown) connected in wireless communication with the sensor 1111 through suitable control electronics. As another example, the sensor 1111 may be controlled to activate automatically after a certain action, such as activation of a button, and/or the like or after a certain amount of time. In some embodiments, the sensor 1111 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 1111 may be activated, for example, before or after, the first housing portion 1101 and the second housing portion 1102 are brought operatively engaged.

The second housing portion 1102 may include a magnetic source 1121 or the like for providing a certain gauss level. The magnetic source 1121 may be similar to the magnetic source 1120 previously described or any of the magnetic sources described in, but is not limited to, U.S. patent application Ser. No. 12/649,619, filed Dec. 30, 2009, entitled "Alignment Systems and Methods," herein incorporated by reference in its entirety.

The magnetic source 1121 may be arranged on or in the second housing portion 1102 at a location to allow the gauss level of the magnetic source 1121 to be detectable and/or measurable by the sensor 1110 in a case where the first housing portion and the second housing portion 1102 are connected properly. Detection of gauss level of the magnetic source 1121 may indicate that the first housing portion 1101 and the second housing portion 1102 have been connected properly. In further embodiments, the sensor 1111 and/or associated electronics may be configured to detect a gauss level that is within a specified range. In such embodiments, a gauss level that is below or exceeds the specified range may indicate an improper connection.

In some embodiments, the magnetic source 1121 may be in contact with the sensor 1111 to allow the sensor 1111 to detect the gauss level of the magnetic source 1121. In other embodiments, the magnetic source 1121 need not be in contact with the sensor 1111 to allow the sensor 1111 to detect the gauss level of the magnetic source 1121. For example, a portion of one or both of the first housing portion 1101 and the second housing portion 1102 may be arranged between the sensor 1111 and the magnetic source 1121.

Furthermore, the sensor 1111 and the magnetic source 1121 may be arranged such that in a case where the first housing portion 1101 and the second housing portion 1102 are not been properly connected, the sensor 1111 will not be able to detect the gauss level (or the gauss level is not within a detectable range) of the magnetic source 1121, for example, because the sensor 1111 and the magnetic source 1121 are too far apart. Accordingly, this may indicate that the first housing portion 1101 and the second housing portion 1102 have not been connected properly.

In further embodiments, electronics (not shown), such as a magnetic threshold switch (e.g., hall switch, reed switch, and/or the like), or the like, associated with the sensor 1111 may be configured to provide a signal or the like upon the sensor 1111 (or other sensor) sensing a signal outside a second range, which in some embodiments may be the same the specified range. In other embodiments, the second range may be different from the specified range. For example, the electronics may provide a signal to the control electronics of the medical device system 1100 to disable the medical device system 1100 or certain portions thereof if a gauss level beyond the second range is detected. Such embodiments may protect the various electronics of the medical device system 1100 in a case where the medical device system 1100 is in operation and is exposed to a strong external magnetic influence, such as an MRI (magnetic resonance imaging) machine, or the like.

In some embodiments, the magnetic source 1121 may provide more than one gauss level. In such embodiments, the sensor 1111 may be configured to detect only a particular gauss level corresponding to a proper connection of the first housing portion 1101 and the second housing portion 1102 similar to a manner previously described. Thus, detection of the particular gauss level may indicate that the first housing portion 1101 and the second housing portion 1102 have been connected properly. In further embodiments, the sensor 1111 may be configured to detect other gauss levels such that detection of the other gauss levels may indicate an improper connection of the first housing portion 1101 and the second housing portion 1102. The electronics may employ an algorithm for processing information relating to the various gauss levels and/or other related information (e.g., magnetic field strength, direction of a field, and/or the like).

With reference to FIGS. 34A-36, in various embodiments, the sensor 1110 and the sensor 1111 may be the same sensor and thus may be configured to sense both a direction of magnetic field and a gauss level from a magnetic source. In some embodiments, the sensor 1110 and the sensor 1111 may both provided for sensing a magnetic source (e.g., 1120, 1121) as previously described. The sensor 1110 and the sensor 1111 may be arranged to sense the same magnetic source or respective magnetic sources. In further embodiments, the electronics may employ an algorithm for processing information relating to the various gauss levels, field directions, and/or other related information.

In various embodiments, the sensor 1110, 1111 may be provided on the first housing portion 1101 and the magnetic source 1120, 1121 may be provided on the second housing portion 1102. In other embodiments, the sensor 1110, 1111 may be provided on the second housing portion 1102 and the magnetic source 1120, 1121 may be provided on the first housing portion 1101. In further embodiments, each of the first housing portion 1101 and the second housing portion 1102 may be provided with a sensor (e.g., 1110, 1111) and complementing magnetic source (e.g., 1120, 1121).

With reference to FIGS. 31A-36, the sensors and/or the electrical contacts may be in electrical communication with electronics (not shown). The electronics may be incorporated within control electronics for controlling a drive device 44 (e.g., FIG. 4) such as, but not limited to, control electronics 52 (e.g., FIG. 4) for controlling the drive device 44. Alternatively, the electronics may be separate from and in addition to the control electronics 52, but connected in electrical communication with the control electronics 52 and/or the drive device 44 to provide a drive control signal to the drive device 44. More specifically, the electronics may be configured to inhibit operation of the drive device 44, unless a signal or a change in state is received by the control electronics 52.

For instance, as previously discussed, a signal or a change in state may be provided upon the first end 922 and the second end 924 interacting with the first main contact 912 and the second main contact 916, for example, in a case where the first housing portion 901 and the second housing portion 902 are in proper alignment and sufficiently close in proximity to connect for operation. In other words, the drive device 44 may be inoperable unless the first housing portion 901 and the second housing portion 902 are operatively engaged properly (i.e., aligned and/or connected properly).

The electronics and/or the control electronics 52 (e.g., FIG. 4) may be configured to control the drive device 44 (e.g., FIG. 4) in various manners in accordance with various embodiments of the invention. Examples are discussed in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

For example, the drive device 44 may be controlled to stop pumping (delivery) operation upon a detection of an interruption of a fluid-flow path or a disconnection of a critical component in the medical device system (e.g., 900, 1100). These may include, but are not limited to, a disconnection of a housing portion from another housing portion or from a base portion, a disconnection of a conduit from another conduit or from a reservoir, a disconnection of a reservoir from a housing portion or a base, and/or the like.

In yet further embodiments, additional sensors may be provided within the medical device system and connected for electrical communication with the electronics 414. Such additional sensors may comprise magnetically and/or electronically actuating switches, magnetic and/or electric field magnitude and direction sensors, inductive sensors, other proximity sensors, contact sensors, and/or the like for providing a detectable signal or change in a state upon proper connection of other components in the medical device system. Such proper connection of other components may comprise, for example, one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the medical device system.

In alternative or in addition, the electronics and/or the control electronics 52 (e.g., FIG. 4) may be configured to detect a first-time connection of a first housing portion (e.g., 901) and a second housing portion (e.g., 902) or a first-time connection of other components, as compared to a re-connection after previous or partial usage. In this manner, the drive device 44 may be controlled to provide a priming operation or other suitable first-time operation(s) upon detection of a first-time connection of the first part 401 and the second part 402.

In various embodiments, the sensors, electrical contacts, and/or associated circuitry may allow for, but is not limited to, tracking a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may allow for verification between two (or more) distinct and separate components, verification of correct positioning between the two (or more) distinct and separate components, verification that the two (or more) distinct and separate components have been connected in the correct order, a safety mechanism to provide notification of separation (intentional or accidental) of any individual component in a multi-component system, and/or the like.

In alternative or in addition, the electronics and/or the control electronics 52 (e.g., FIG. 4) may be configured to provide a user-perceptible indication of a proper alignment and/or connection of the first housing portion and the second housing portion or of other components. For example, upon detection of a proper alignment and/or connection of the first housing portion and the second housing portion 402, the electronics 414 and/or the control electronics 52 may provide a suitable control signal to activate an indicator device 420, as shown in FIG. 36.

The indicator device 420 may operated by a processor 422. The processor 422 may be configured to execute various programs and/or to process various information, such as data received from one or more sensors, responsive devices, and/or other interactive elements. The processor 422, for example, may be configured to compare detected signals with thresholds and/or pre-stored values in memory 424.

With reference to FIGS. 31A-36, the indicator device 420 may include, but is not limited to, an audible indicator, an optical indicator, a tactile indicator, combinations of one or more those indicators, and/or the like. For example, upon a proper alignment or connection of components as described above, an audible beeping sound or other suitable sound may be generated by a sound generating device in or associated with one or both of the first housing portion and the second housing portion. For example, upon a proper alignment or connection of components as described above, a flashing light or other suitable visual indicator may be generated by an LED or other light source or a display device on or associated with one or both of the first housing portion and the second housing portion. For example, upon a proper alignment or connection of components as described above, a vibration and/or the like may be generated by a vibration device and/or the like in or associated with one or both of the first housing portion and the second housing portion. Examples of indicator devices are discussed in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A medical device for treating a user, the medical device comprising:

a first housing portion adapted to be carried by a user;

a second housing portion configured to be selectively operatively engaged with and disengaged from the first housing portion;

a magnetic source having at least one of a certain magnetic field and a certain magnetic strength provided on at least one of the first housing portion and the second housing portion;

a sensor for detecting at least one of the certain magnetic field and the certain magnetic strength provided on the other of the first housing portion and the second housing portion; and circuitry electrically connected to the sensor and configured to provide a first signal in a case where the first housing portion and the second housing portion are brought together and the sensor detects at least one of the certain magnetic field and the certain magnetic strength of the magnetic source;

the circuitry further configured to provide a second signal in a case where the first housing portion and the second housing portion are brought together and the sensor detects at least one of a magnetic field different from the certain magnetic field and a magnetic strength different from the certain magnetic strength of the magnetic source.

2. The medical device of claim 1, the sensor configured to provide a signal for activating control circuitry in a case where the sensor detects a gauss level exceeding a first pre-defined threshold value.

3. The medical device of claim 2, wherein the sensor comprises a magnetic threshold switch.

4. The medical device of claim 1, wherein the certain magnetic field includes a direction, the sensor configured for detecting the direction.

5. The medical device of claim 1, wherein the circuitry is configured to provide a first signal in a case where the first housing portion and the second housing portion are brought together and the sensor detects a gauss level of the magnetic source that is above a first pre-defined threshold and below a second pre-defined threshold, and provides a second signal in a case where the first housing portion and the second housing portion are brought together and the sensor detects a gauss level of the magnetic source that is above the second pre-defined threshold.

6. The medical device of claim 1, wherein the circuitry is configured to provide a first signal in a case where the first housing portion and the second housing portion are brought together and the sensor detects a first magnetic field direction of the magnetic source, and provides a second signal in a case where the first housing portion and the second housing portion are brought together and the sensor detects a second magnetic field direction of the magnetic source, where the second magnetic field direction is different from the first magnetic field direction.

7. The medical device of claim 1, wherein the sensor is configured to provide a first signal having information corresponding to a detected gauss level to the circuitry when the sensor detects a gauss level of the magnetic source, the circuitry including electronics configured to process information relating to the gauss level.

8. The medical device of claim 1, wherein the sensor is configured to provide a first signal having information corresponding to a direction of the certain magnetic field to the circuitry when the sensor detects the certain magnetic field of the magnetic source, the circuitry including electronics configured to process information relating to the direction of the certain magnetic field.

9. A medical device for treating a user, the medical device comprising:

a first housing portion adapted to be carried by a user;

a second housing portion configured to be selectively operatively engaged with and disengaged from the first housing portion;

a magnetic source having at least one of a certain magnetic field and a certain magnetic strength provided on at least one of the first housing portion and the second housing portion;

a sensor for detecting at least one of the certain magnetic field and the certain magnetic strength provided on the other of the first housing portion and the second housing portion, the sensor comprising a first magnetic threshold switch configured to provide a signal for activating control circuitry in a case where the sensor detects a gauss level exceeding a first pre-defined threshold value; and circuitry configured to provide a first signal in a case where the first housing portion and the second housing portion are brought together and the sensor detects at least one of the certain magnetic field and the certain magnetic strength of the magnetic source;

the circuitry further configured to provide a second signal in a case where the first housing portion and the second housing portion are brought together and the sensor detects at least one of a magnetic field different from the certain magnetic field and a magnetic strength different from the certain magnetic strength of the magnetic source;

wherein the sensor further comprises a second magnetic threshold switch configured to provide a signal for deactivating at least one of the control circuitry and the sensor in a case where the sensor detects a gauss level exceeding a second pre-defined threshold value, wherein the second pre-defined threshold value is greater than the first pre-defined threshold value.

10. The medical device of claim 1, the magnetic source having a certain magnetic field direction;

the sensor for detecting the certain magnetic field direction;

the circuitry configured to provide the first signal in a case where the first housing portion and the second housing portion are brought together and the sensor detects the certain magnetic field direction.

11. A medical device for treating a user, the medical device comprising:

a first housing portion adapted to be carried by a user;

a second housing portion configured to be selectively operatively engaged with and disengaged from the first housing portion;

a magnetic source having at least one of a certain magnetic field and a certain magnetic strength provided on at least one of the first housing portion and the second housing portion;

a sensor for detecting at least one of the certain magnetic field and the certain magnetic strength provided on the other of the first housing portion and the second housing portion; and circuitry configured to provide a first signal in a case where the first housing portion and the second housing portion are brought together and the sensor detects at least one of the certain magnetic field and the certain magnetic strength of the magnetic source;

the circuitry further configured to provide a second signal in a case where the first housing portion and the second housing portion are brought together and the sensor detects at least one of a magnetic field different from the certain magnetic field and a magnetic strength different from the certain magnetic strength of the magnetic source;

the magnetic source having a certain magnetic field direction;

the sensor for detecting the certain magnetic field direction;

the circuitry configured to provide the first signal in a case where the first housing portion and the second housing portion are brought together and the sensor detects the certain magnetic field direction;

the circuitry further configured to provide the second signal in a case where the first housing portion and the second housing portion are brought together and the sensor detects a magnetic field direction different from the certain magnetic field direction.

12. A method of making a medical device, the method comprising adapting a first housing portion to be carried by a user;

configuring a second housing portion to be selectively operatively engaged with and disengaged from the first housing portion;

providing a magnetic source having at least one of a certain magnetic field and a certain magnetic strength on at least one of the first housing portion and the second housing portion;

providing a sensor for detecting at least one of the certain magnetic field and the certain magnetic strength on the other of the first housing portion and the second housing portion;

electrically coupling circuitry to the sensor and configuring the circuitry to provide a first signal in a case where the first housing portion and the second housing portion are brought together and the sensor detects at least one of the certain magnetic field and the certain magnetic strength of the magnetic source; and configuring the circuitry to provide a second signal in a case where the first housing portion and the second housing portion are brought together and the sensor detects at least one of a magnetic field different from the certain magnetic field and a magnetic strength different from the certain magnetic strength of the magnetic source.

13. The method of claim 12, wherein providing the sensor comprises providing a sensor configured to provide a signal for activating control circuitry in a case where the sensor detects a gauss level exceeding a first pre-defined threshold value.

14. The method of claim 13, wherein the sensor comprises a magnetic threshold switch.

15. The method of claim 14, further comprising providing a second magnetic threshold switch configured to provide a signal for deactivating at least one of the control circuitry and the sensor in a case where the sensor detects a gauss level exceeding a second pre-defined threshold value, wherein the second pre-defined threshold value is greater than the first pre-defined threshold value.

16. The method of claim 12, wherein
providing the magnetic source comprises providing a magnetic source having a certain magnetic field direction;
providing the sensor comprises providing a sensor for detecting the certain magnetic field direction; and
configuring the circuitry comprises configuring the circuitry to provide the first signal in a case where the first housing portion and the second housing portion are brought together and the sensor detects the certain magnetic field direction.

17. The method of claim 16, wherein configuring the circuitry further comprises configuring the circuitry to provide the second signal in a case where the first housing portion and the second housing portion are brought together and the sensor detects a magnetic field direction different from the certain magnetic field direction.

18. The method of claim 12, wherein the certain magnetic field includes a direction, and wherein providing the sensor comprises providing a sensor configured for detecting the direction.

19. The method of claim 12, wherein configuring the circuitry further comprises configuring the circuitry to provide a first signal in a case where the first housing portion and the second housing portion are brought together and the sensor detects a gauss level of the magnetic source that is above a first pre-defined threshold and below a second pre-defined threshold, and to provide a second signal in a case where the first housing portion and the second housing portion are brought together and the sensor detects a gauss level of the magnetic source that is above the second pre-defined threshold.

20. The method of claim 12, wherein configuring the circuitry further comprises configuring the circuitry to provide a first signal in a case where the first housing portion and the second housing portion are brought together and the sensor detects a first magnetic field direction of the magnetic source, and to provide a second signal in a case where the first housing portion and the second housing portion are brought together and the sensor detects a second magnetic field direction of the magnetic source, where the second magnetic field direction is different from the first magnetic field direction.

\* \* \* \* \*